(12) United States Patent
Meyer et al.

(10) Patent No.: US 8,906,911 B2
(45) Date of Patent: Dec. 9, 2014

(54) CHEMOKINE RECEPTOR ANTAGONISTS

(71) Applicant: AbbVie Inc., North Chicago, IL (US)

(72) Inventors: Michael D. Meyer, Lake Bluff, IL (US); Xueqing Wang, Northbrook, IL (US); Tao Guo, Dayton, NJ (US); Robert Guo Ping Wei, San Ramon, CA (US); Lijuan Jane Wang, Wildwood, MO (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/853,394

(22) Filed: Mar. 29, 2013

(65) Prior Publication Data

US 2013/0261129 A1    Oct. 3, 2013

(30) Foreign Application Priority Data

Apr. 2, 2012   (CN) ................. PCT/CN2012/073499

(51) Int. Cl.

| | |
|---|---|
| *C07D 487/04* | (2006.01) |
| *C07D 487/08* | (2006.01) |
| *A61K 31/427* | (2006.01) |
| *A61K 31/407* | (2006.01) |
| *A61K 31/4439* | (2006.01) |
| *A61K 31/501* | (2006.01) |
| *A61K 31/506* | (2006.01) |
| *A61K 31/4995* | (2006.01) |
| *A61K 31/5377* | (2006.01) |
| *C07D 451/02* | (2006.01) |

(52) U.S. Cl.
CPC ............ *C07D 487/08* (2013.01); *C07D 451/02* (2013.01)
USPC ................... 514/234.5; 514/249; 514/252.06; 514/275; 514/300; 514/338; 514/370; 514/412; 514/414; 544/143; 544/238; 544/297; 544/349; 546/122; 546/276.7; 548/181; 548/453

(58) Field of Classification Search
None
See application file for complete search history.

(56) References Cited

U.S. PATENT DOCUMENTS

| | | | |
|---|---|---|---|
| 6,090,382 | A  | 7/2000  | Salfeld et al. |
| 6,906,072 | B1 | 6/2005  | Yamamoto et al. |
| 7,511,013 | B2 | 3/2009  | Molino et al. |
| 7,514,068 | B2 | 4/2009  | Tung |
| 7,521,421 | B2 | 4/2009  | Naicker et al. |
| 7,528,131 | B2 | 5/2009  | Persichetti et al. |
| 7,531,685 | B2 | 5/2009  | Czarnik |
| 7,534,814 | B2 | 5/2009  | Ascher et al. |
| 7,538,189 | B2 | 5/2009  | Naicker et al. |
| 2005/0019302 | A1 | 1/2005  | Murray |
| 2005/0267146 | A1 | 12/2005 | Xue et al. |
| 2007/0032526 | A1 | 2/2007  | Carter et al. |
| 2007/0037785 | A1 | 2/2007  | Ansorge et al. |
| 2008/0176883 | A1 | 7/2008  | George et al. |
| 2009/0082471 | A1 | 3/2009  | Czarnk |
| 2009/0088416 | A1 | 4/2009  | Czarnik |
| 2009/0093422 | A1 | 4/2009  | Tung et al. |
| 2009/0105147 | A1 | 4/2009  | Masse |
| 2009/0105307 | A1 | 4/2009  | Galley et al. |
| 2009/0105338 | A1 | 4/2009  | Czarnik |
| 2009/0111840 | A1 | 4/2009  | Herold et al. |
| 2009/0118238 | A1 | 5/2009  | Czarnik |
| 2009/0118298 | A1 | 5/2009  | George et al. |
| 2009/0131363 | A1 | 5/2009  | Harbeson |
| 2009/0131485 | A1 | 5/2009  | Liu et al. |
| 2009/0137457 | A1 | 5/2009  | Harbeson |

FOREIGN PATENT DOCUMENTS

| | | |
|---|---|---|
| WO | 8910961 A1 | 11/1989 |
| WO | 9507271 A1 | 3/1995 |
| WO | 9710223 A1 | 3/1997 |
| WO | 0244181 A1 | 6/2002 |
| WO | 2004050024 A2 | 6/2004 |
| WO | 2005037779 A2 | 4/2005 |
| WO | 2005044264 A1 | 5/2005 |
| WO | 2005099353 A2 | 10/2005 |
| WO | 2005115392 A2 | 12/2005 |
| WO | 2006008754 A1 | 1/2006 |
| WO | 2009042193 A1 | 4/2009 |
| WO | 2013010453 A1 | 1/2013 |

OTHER PUBLICATIONS

Abbadie, C., et al. "Impaired neuropathic pain responses in mice lacking the chemokine receptor $CCR_2$," PNAS 2003, 100(13): 7947-4952.
Banker, G. S., et al., Editor, "Modern Pharmaceutics," $3^{rd}$ Ed, 1996, Marcel Dekker, NY. pp. 451, 596.
Bazan, J. F., et al., "A new class of membrane-bound chemokine with a CX3C motif," Nature 1997, 385: 640-644.

(Continued)

*Primary Examiner* — Emily Bernhardt

(57) ABSTRACT

Disclosed herein are chemokine receptor antagonists of formula (I)

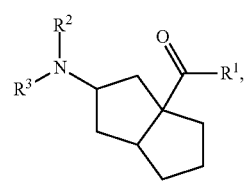

(I)

wherein $R^1$, $R^2$, and $R^3$ are as defined in the specification. Compositions comprising such compounds; and methods for treating conditions and disorders using such compounds and compositions are also described.

21 Claims, No Drawings

(56) References Cited

OTHER PUBLICATIONS

Ben-Baruch, A., et al., "Monocyte chemotactic protein-3 (Mcp3) interacts with multiple leukocyte receptors. C-C CKR1, a receptor for macrophage inflammatory protein-1α/Rantes, is also a functional receptor for MCP3," J Biol Chem 1995, 270(38): 22123-22128.

Beylot, M., et al., "In vivo Studies of Intrahepatic Metabolic Pathways," Diabetes & Metabolism 1997, 23: 251-257.

Blagojevic, N., et al., "Role of Heavy Water in Boron Neutron Capture Therapy," Dosimetry & Treatment Planning for Neutron Capture Therapy 1994, R. Zamenhof et al., Editors, Advanced Medical Publishing, Madison, WI. pp. 125-134.

Blake, M. I., et al., "Studies with Deuterated Drugs," J Pharm Sci 1975, 64(3): 367-391.

Brickner, S. J., et al., "Synthesis and Antibacterial Activity of U-100592 and U-100766, Two Oxazolidinone Antibacterial Agents for the Potential Treatment of Multidrug-Resistant Gram-Positive Bacterial Infections," J Med Chem 1996, 39(3): 673-679.

Campbell, J. J., et al., "6-C-kine (SLC), a lymphocyte adhesion-triggering chemokine expressed by high endothelium, is an agonist for the MIP3β receptor CCR7," J Cell Biol 1998, 141(4): 1053-1059.

Chaudhuri, A., et al., "Expression of the Duffy antigen in K562 cells," J Biol Chem 1994, 269(11): 7835-7838.

Czajka, D. M., et al., "Effect of Deuterium Oxide on the Reproductive Potential of Mice," Ann N Y Acad Sci 1960, 84: 770-779.

Czajka, D. M., et al., "Physiological Effects of Deuterium on Dogs," Am J Physiol 1961, 201(2): 357-362.

Dairaghi, D. J., et al., "HHV8-encoded vMIP-1 selectively engages chemokine receptor CCR8," J Biol Chem 1999, 274(31): 21569-21574.

Dansereau, M-A., et al. "Spinal CCL2 pronociceptive action is no longer effective in CCR2 receptor antagonist-treated rats," J Neurochem 2008, 106: 757-769.

Deng, H-K., et al., "Identification of major co-receptor for primary isolates of HIV-1," Nature 1996, 381: 661-666.

Fingl, E., et al. Chapter 1, The Pharmacological Basis of Therapeutics (5th edition), 1975, Editor Goodman et al., MacMillan Publishing Co., Inc., New York. pp. 1-46.

Foster, A. B., et al., "Deuterium Isotope Effects in the Metabolism of Drugs and Xenobiotics: Implications for Drug Design," Advances in Drug Research, vol. 14, 1985, Editor Bernard Testa, Academic Press. pp. 1-36.

Gennaro, A., Editor "Remington's Pharmaceutical Sciences" 18th Ed., 1990, Mack Publishing Company, (Table of Contents, 5 pages).

Greaves, D. R., et al., "CCR6, a CC chemokine receptor that interacts with macrophage inflammatory protein 3α and is highly expressed in dendritic cells," J Exp Med 1997, 186(6): 837-844.

Greene, T. W., et al., Editor, Protective Groups in Organic Synthesis, 1999, 3rd ed., John Wiley & Sons, NY (20 pages, Table of Contents).

Horuk, R., "Molecular Properties of the chemokine receptor family," Trends Pharmacol Sci 1994, 15(5): 159-165.

Imai, T., et al., "Macrophage-derived chemokine is a functional ligand for the CC chemokine receptor 4," J Biol Chem 1998, 273(3): 1764-1768.

International Search Report for International Application No. PCT/CN2012/073499 dated Jan. 17, 2013 (6 pages).

Kato, S., et al., "Synthesis of Deuterated Mosapride Citrate," J. Labelled Comp Rad 1995, 36(10): 927-932.

Kelner, G. S., et al., "Lymphotactin: A cytokine that represents a new class of chemokine," Science 1994, 266(5189): 1395-1399.

Kushner, D.J., et al., "Pharmacological uses and perspectives of heavy water and deuterated compounds," Can J Physiol Pharm 1999, 77: 79-88.

Lizondo, J., et al., "Linezolid" Drug Future 1996, 21(11): 1116-1123.

Mallesham, B., et al., Highly Efficient CuI-Catalyzed Coupling of Aryl Bromides with Oxazolidinones Using Buchwald's Protocol: A Short Route to Linezolid and Toloxatone, Org Lett 2003, 5(7): 963-965.

Murphy, P. M., et al., "The molecular biology of leukocyte chemoattractant receptors," Annu Rev Immunol 1994, 12: 593-633.

Neote, K., et al., "Molecular cloning, functional expression, and signalling characteristics of a C-C-chemokine receptor," Cell 1993, 72(3): 415-425.

Nibbs, R.J.B., et al., "Cloning and characterization of a novel promiscuous human β chemokine receptor D6," J Biol Chem 1997, 272(51): 32078-32083.

O'Malley, R. F., et al., "Anodic fluorination of benz[a]anthracene," J Org Chem 1981, 46(13): 2816-2818.

Ponath, P. D., et al., "Molecular cloning and characterization of human eotaxin receptor expressed selectively on eosinophils," J Exp Med 1996, 183(6): 2437-2448.

Samson, M., et al., "Molecular cloning and functional expression of new human CC-chemokine receptor gene," Biochem 1996, 35(11): 3362-3367.

Schall, T. J., "Biology of the Rantes/Sis cytokine family," Cytokine 1991, 3(3): 165-183.

Schall, T. J., et al., "Hemokines, leukocyte trafficking, and inflammation," Curr Opin Immunol 1994, 6(6): 865-873.

Serrano, A., et al., "Blocking spinal CCR2 with AZ889 reversed hyperalgesia in a model of neuropathic pain," Mol Pain 2010, 6: 90 (14 pages).

Sun, J.H., et al., "MCP-1 Enhances Excitability of Nociceptive Neurons in Chronically Compressed Dorsal Root Ganglia," J Neurophysiol 2006, 96(5): 2189-2199.

Thomson, J. F., "Physiological Effects of $D_2O$ in Mammals," Ann N Y Acad Sci 1960, 84: 736-744.

Wang, H., et al., "Microinjection of MCP-1 into the rostral ventromedial medulla induces microglial activation and behavioral hyperalgesia in rats," Poster, Soc Neurosci 2009 (Presentation Abstract, 2 pages).

White, F.A., et al., "Chemokines and the pathophysiology of neuropathic pain," PNAS USA 2007, 104(51): 20151-20158.

Wolff, M. E., Editor, "Burger's Medicinal Chemistry and Drug Discovery, $5^{th}$ Edition, vol. 1: Principles and Practice," John Wiley & Sons 1995. pp. 975-977.

Zaballos, A., et al., "Cutting edge: identification of the orphan chemokine receptor GPR-9-6 as CCR9, the receptor for the chemokine TECK," J Immunol 1999, 162(10): 5671-5675.

CHEMOKINE RECEPTOR ANTAGONISTS

CROSS-REFERENCE TO RELATED PATENT APPLICATION

This patent application claims the benefit of International Patent Application No. PCT/CN2012/073499 (filed Apr. 2, 2012). The entire text of that International Patent Application is incorporated by reference into this application.

BACKGROUND

Chemokines are chemotactic cytokines that are released by a wide variety of cells to attract leukocytes, as illustrated by macrophages, T cells, B cells, eosinophils, basophils, and neutrophils to and from sites of inflammation or within specific compartments, as illustrated by lymph nodes (reviewed in Schall, Cytokine 1991; 3:165-183; Schall, et al., Curr. Opin. Immunol. 1994; 6:865-873; and Murphy, Rev. Immun. 1994; 12:593-633). In addition to stimulating chemotaxis, other changes can be selectively induced by chemokines in responsive cells, including changes in cell shape, transient rises in the concentration of intracellular free calcium ions ($[Ca^{2+}]$), granule exocytosis, integrin upregulation, formation of bioactive lipids (e.g., leukotrienes), and respiratory burst, associated with leukocyte activation. Thus, the chemokines are early modulators of inflammatory response, effecting inflammatory mediator release, chemotaxis and extravasation to sites of infection or inflammation.

There are four classes of chemokines, CXC ($\alpha$), CC ($\beta$), C ($\gamma$), and $CX_3C$ ($\delta$), depending on whether the first two cysteines are separated by a single amino acid (C—X—C), are adjacent (C—C), have a missing cysteine pair (C), or are separated by three amino acids ($CX_3C$). The $\alpha$-chemokines, such as interleukin-8 (IL-8), melanoma growth stimulatory activity protein (MGSA), and stromal cell derived factor 1 (SDF-1) are chemotactic primarily for neutrophils and lymphocytes, whereas 1-chemokines, such as RANTES, MIP-1$\alpha$, MIP-10, monocyte chemotactic protein-1 (MCP-1), MCP-2, MCP-3, and eotaxin are chemotactic for macrophages, T-cells, eosinophils and basophils (Deng, et al., Nature 1996; 381:661-666). The C chemokine lymphotactin shows specificity for lymphocytes (Kelner, et al., Science 1994; 266:1395-1399) while the $CX_3C$ chemokine fractalkine shows specificity for lymphocytes and monocytes (Bazan, et al., Nature 1997; 385:640-644).

Chemokines bind specific cell-surface receptors belonging to the family of G-protein-coupled seven-transmembrane-domain proteins (reviewed in Horuk, Trends Pharm. Sci. 1994; 15:159-165) termed "chemokine receptors." On binding their cognate ligands, chemokine receptors transduce an intracellular signal through the associated heterotrimeric G protein, resulting in a rapid increase in intracellular calcium concentration. There are at least twelve human chemokine receptors that bind or respond to $\beta$-chemokines with the following characteristic pattern: CCR1 (or "CKR-1" or "CC-CKR-1") MIP-1$\alpha$, MIP-13, MCP-3, RANTES (Ben-Barruch, et al., J. Biol. Chem. 1995; 270:22123-22128; Neote, et al., Cell 1993; 72:415425); CCR2A and CCR2B (or "CKR-2A"/"CKR-2A" or "CC-CKR-2A"/"CC-CKR2A") MCP-1, MCP-2, MCP-3, MCP-4; CCR3 (or "CKR-3" or "CC-CKR-3") eotaxin, RANTES, MCP; (Ponath, et al., J. Exp. Med. 1996; 183:2437-2448); CCR4 (or "CKR-4" or "CC-CKR-4") TARC, MDC (Imai, et al., J. Biol. Chem. 1998; 273:1764-1768); CCR5 (or "CKR-5" or "CC-CKR-5") MIP-1$\alpha$, RANTES, MIP-1$\beta$; (Sanson, et al., Biochemistry 1996; 35:3362-3367); CCR6MIP-3$\alpha$ (Greaves, et al., J. Exp. Med. 1997; 186:837-844); CCR7 MIP-3$\beta$ and 6Ckine (Campbell, et al., J. Cell. Biol. 1998; 141:1053-1059); CCR8 I-309, HHV8 vMIP-I, HHV-8 vMIP-II, MCV vMCC-I (Dairaghi, et al., J. Biol. Chem. 1999; 274:21569-21574); CCR9TECK (Zaballos, et al., J. Immunol. 1999; 162:5671-5675), D6 MIP-1 beta, RANTES, and MCP-3 (Nibbs, et al., J. Biol. Chem. 1997; 272:32078-32083), and the Duffy blood-group antigen RANTES, MCP-1 (Chaudhun, et al., J. Biol. Chem. 1994; 269:7835-7838).

Chemokine receptors, such as CCR1, CCR2, CCR3, CCR4, CCR5, CCR6, CCR7, CCR8, CCR9, CXCR1, CXCR2, CXCR3, CXCR4, CXCR5, $CX_3CR1$, and XCR1 have been implicated as being important mediators of inflammatory and immunoregulatory disorders and diseases, including asthma and allergic diseases, as well as autoimmune pathologies such as rheumatoid arthritis and atherosclerosis.

The CCR2 chemokine receptor is expressed primarily in monocytes and activated T lymphocytes, and its functional activity can be measured by cytosolic calcium elevation or chemotaxis. CCR2 exists in two isoforms, CCR2A and CCR2B. These two isoforms are alternatively spliced variants of a single MCP-1 receptor gene and differ only in the carboxyl-terminal tails. The chromosomal location of the CCR2 gene is localized to 3p21. The CC chemokines, MCP-1, MCP-2, MCP-3, and MCP-4, have been identified as the ligands that are selective and of high affinity to the CCR2 receptor.

The highly selective expression of CCR2 makes it an ideal target for intervention to interrupt inappropriate monocyte and T cell trafficking. The clinical indications for such intervention are in inflammatory diseases and T-cell mediated autoimmune diseases such as multiple sclerosis, rheumatoid arthritis, asthma, allergy, chronic obstructive pulmonary disease, atherosclerosis, restinosis, type I and type II diabetes, metabolic syndrome, and pain. Ectopic expression of MCP-1 and CCR2 in certain tumors indicates that selective modulation (such as antagonism or inhibition) of CCR2 can have value in tumor immunotherapy, particularly attenuation of metastasis.

The native peptide ligand of CCR2 is monocyte chemoattractant protein-1 (MCP-1 or CCL2) containing two adjacent disulfide bonds. Ample evidence exists for the role of the CCR2/MCP-1 system in preclinical animal models of pain (White F. A., Jung F., and Miller R. J., Proc. Natl. Acad. Sci. USA 2007; 51:20151). Although CCR2 and MCP-1 have limited expression levels in the CNS tissues under normal conditions, significant upregulation of CCR2 and MCP-1 has been observed following a neuropathic injury in tissue relevant to pain, including neurons and glia in the spinal cord, rostroventromedial medulla (RVM) and DRG (Wang H., Zou S., Wei F., Dubner R., and Ren K., Soc for Neurosci Poster 2009; 72.3). MCP-1 has been shown to increase the excitability of neurons acutely dissociated from the DRG tissue (Sun J. H., Yang B., Donnelly D. F., Ma C., and LaMotte R. H., J Neurophysiol. 2006; 96:2189). In addition, direct injection of MCP-1 in the spinal cord induces thermal hyperalgesia and mechanical allodynia (Dansereau et al. Neurochem. 2008; 106:7), and the MCP-1 induced pronociception can be blocked by a CCR2 antagonist, INCB3344. Similarly, the hyperalgesia induced by MCP-1 injection in the RVM is reversed by another CCR2 antagonist, RS102895 (Wang H., Zou S., Wei F., Dubner R. and Ren K., Soc for Neurosci Poster 2009; 72.3). In addition, CCR2 knock out mice exhibit significantly reduced mechanical allydonia following nerve injury and reduced nocifensive behavior in the second phase of the formalin model, whereas they exhibit normal sensitivity to acute pain stimulation in the hot plate model (Abbadie C., Lindia J. A., Cumiskey A. M., Peterson L. B., Mudgett J. S., Bayne E. K., DeMartino J. A., MacIntyre D. E., and Forrest M. J., Proc Natl Aca Sci USA 2003; 100:7947). Treatment with AZ889 (Serrano A., Pare M., McIntosh F., Elmes S. J. R. Martino G., Jomphe C., Lessard E., Lembo P. M. C., Vaillancourt F., Perkins M. N., and Cao C. Q., Mol. Pain. 2010; 6:90), a CCR2 antagonist, abolished CCL2-evoked neuronal excitation, confirming that this activity is CCR2-mediated. Neuronal and non-neuronal cells in the spinal cord were also excited by CCL2 applications indicating an important role of spinal CCR2 in neuropathic pain. In vivo spinal intrathecal injection of AZ889 produced dose-dependent analgesia in chronic constriction injury rats (Serrano A., Paré M., McIntosh F., Elmes S. J. R., Martino G., Jomphe C., Lessard E., Lembo P. M. C., Vaillancourt F., Perkins M. N., and Cao C. Q., Mol. Pain. 2010; 6:90). Additionally, application of AZ889 to the exposed spinal cord inhibited evoked neuronal activity and confirmed that CCR2-mediated analgesia involved predominantly the spinal cord.

In view of the clinical importance of CCR2, the identification of compounds that modulate CCR2 function represents an attractive avenue into the development of new therapeutic agents that can be used to treat diseases that are associated with chemokine receptor expression or activity such as inflammatory, autoimmune disease, cancer, and pain. Such compounds are provided herein.

SUMMARY

Disclosed herein are compounds of formula (I):

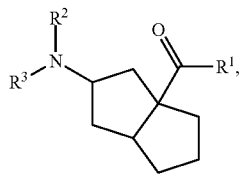

(I)

wherein:
$R^1$ is formula (a), (b), or (c):

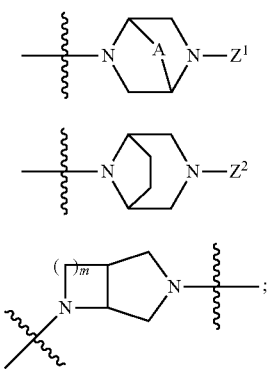

A is $CH_2$ or $CH_2CH_2$;
$Z^1$ and $Z^2$, are each independently —C(O)O(alkyl), aryl, or heteroaryl, each of which is independently unsubstituted or substituted with 1, 2, 3, or 4 substituents independently selected from the group consisting of $C_1$-$C_6$ alkyl, $C_2$-$C_4$ alkenyl, $C_2$-$C_4$ alkynyl, halogen, $C_1$-$C_6$ haloalkyl, CN, $OR^a$, $NR^bR^c$, —C(O)$NR^bR^c$, and —S(O)$_2NR^bR^c$; wherein $R^a$, $R^b$, and $R^c$, at each occurrence, are each independently hydrogen, $C_1$-$C_6$ alkyl, or $C_1$-$C_6$ haloalkyl;

m is 1 or 2;

$R^2$ is hydrogen or $C_1$-$C_6$ alkyl wherein the $C_1$-$C_6$ alkyl is optionally substituted with $C_1$-$C_6$ haloalkyl, alkoxy, or haloalkoxy, and $R^3$ is:

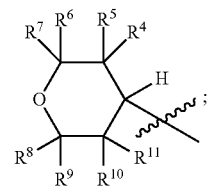

wherein:
$R^4$ is $C_1$-$C_6$ alkyl, O($C_1$-$C_6$ alkyl), or O($C_1$-$C_6$ haloalkyl);
$R^5$, $R^6$, $R^7$, $R^8$, $R^9$, $R^{10}$, and $R^{11}$, are each independently hydrogen, $C_1$-$C_6$ alkyl, or halogen;

or $R^2$ and $R^3$, together with the nitrogen atom to which they are attached, form a ring of formula (i), (ii), or (iii):

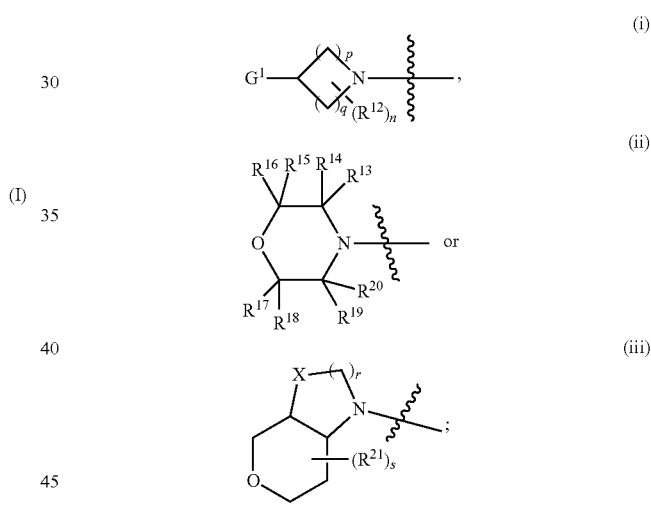

wherein:
$R^{12}$, at each occurrence, represents an optional substituent on any substitutable carbon atom, and is independently $C_1$-$C_6$ alkyl, $C_1$-$C_6$ haloalkyl, CN, OH, or halogen;
n is 0, 1, or 2;
p is 1 or 2;
q is 1 or 2;
$G^1$ is aryl or heteroaryl, each of which is optionally substituted with 1, 2, or 3 substituents independently selected from the group consisting of $C_1$-$C_6$ alkyl, halogen, $C_1$-$C_6$ haloalkyl, OH, alkoxy, haloalkoxy, CN, —C(O)OH, —C(O)O(alkyl), —($C_1$-$C_6$ alkylenyl)-OH, —($C_1$-$C_6$ alkylenyl)-C(O)OH, or tetrazolyl;
$R^{13}$ is hydrogen, $C_1$-$C_6$ alkyl, or —($C_1$-$C_6$ alkylenyl)-O(alkyl);
$R^{14}$, $R^{15}$, $R^{16}$, $R^{17}$, $R^{18}$, $R^{19}$, and $R^{20}$, are each independently hydrogen or $C_1$-$C_6$ alkyl;
X is $CH_2$, O, N($R^w$) wherein $R^w$ is hydrogen, $C_1$-$C_6$ alkyl, or $C_1$-$C_6$ haloalkyl;
r is 1 or 2;

s is 0, 1, 2, 3, or 4; and $R^{21}$, at each occurrence, represents an optional substituent on any substitutable carbon atom of the bicyclic ring, and is independently halogen, $C_1$-$C_6$ alkyl, or $C_1$-$C_6$ haloalkyl.

Provided also is a pharmaceutical composition comprising therapeutically effective amount of a compound of formula (I) or a pharmaceutically acceptable salt, solvate, or salt of a solvate thereof, in combination with a pharmaceutically acceptable carrier, with or without an additional therapeutic agent. The present compounds or compositions described herein can be administered in accordance with methods described herein, typically as part of a therapeutic regimen for treatment or prevention of conditions and disorders associated to the expression or acitivity of CCR2. More particularly, the methods are useful for treating conditions such as, but not limited to, rheumatoid arthritis, osteoarthritis, asthma, chronic obstructive pulmonary disease, sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy, systemic lupus erythematosus, an ocular condition, a cancer, a solid tumor, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), abetalipoprotemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, alpha-1 antitrypsin deficiency, amyotrophic lateral sclerosis, anemia, angina pectoris, anterior horn cell degeneration, anti cd3 therapy, antiphospholipid syndrome, anti-receptor hypersensitivity reactions, hypersensitivity reactions, hyperkinetic movement disorders, hypersensitivity pneumonitis, hypertension, hypokinetic movement disorders, aortic and peripheral aneurysms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, atrial fibrillation (sustained or paroxysmal), atrial flutter, atrioventricular block, B cell lymphoma, bone graft rejection, bone marrow transplant (BMT) rejection, small bowel transplant rejection, spinal ataxia, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia, chronic alcoholism, chronic inflammatory pathologies, chronic lymphocytic leukemia, chronic salicylate intoxication, colorectal carcinoma, congestive heart failure, conjunctivitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetic ateriosclerotic disease, Diffuses Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, gram negative sepsis, gram positive sepsis, granulomas due to intracellular organisms, hairy cell leukemia, Hallerrorden-Spatz disease, hay fever, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile rheumatoid arthritis, juvenile spinal muscular atrophy, kidney transplant rejection, legionella, leishmaniasis, lipedema, liver transplant rejection, lymphederma, malaria, malignant Lymphoma, malignant histiocytosis, malignant melanoma, meningococcemia, metabolic/idiopathic, migraine headache, mitochondrial multi-system disorder, monoclonal gammopathy, multiple myeloma, multiple systems degenerations (Mencel Dejerine-Thomas Shi-Drager and Machado-Joseph), myasthenia gravis, *mycobacterium avium* intracellulare, *mycobacterium tuberculosis*, myelodyplastic syndrome, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, Kaposi's sarcoma, Hodgkin's disease, lymphoma, myeloma, leukaemia, malignant ascites, hematopoietic cancers, Crow-Fukase (POEMS) syndrome (polyneuropathy, organomegaly, endocrinopathy, monoclonal gammopathy, and skin changes syndrome), a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, Progressive supranucleo Palsy, primary pulmonary hypertension, radiation therapy, Raynaud's phenomenon and disease, Refsum's disease, regular narrow QRS tachycardia, renovascular hypertension, restrictive cardiomyopathy, sarcoma, senile chorea, Senile Dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, lung disease, systemic sclerosis associated interstitial lung disease, rheumatoid arthritis associated interstitial lung disease, systemic lupus erythematosus associated lung disease, dermatomyositis/polymyositis associated lung disease, Sjigren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, pain, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome, proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, age-related macular degeneration, acute idiopathic polyneuritis, acuter or chronic immune disease associated with organ transplantation, acute inflammatory demyelinating polyradiculoneuropathy, acute ischemia, adult Still's disease, allergy, anaphylaxis, anti-phospholipid antibody syndrome, aplastic anemia, atopic eczema, atopic dermatitis, autoimmune dermatitis, autoimmune diabetes, autoimmune disorder associated with *streptococcus* infection, autoimmune enteropathy, autoimmune hepatitis, autoimmune hearing loss, autoimmune lymphoproliferative syndrome, autoimmune myocarditis, autoimmune neutropenia, autoimmune premature ovarian failure, autoimmune thrombocytopenia, autoimmune uveitis, Behcet's disease, blepharitis, bronchiectasis, bullous pemphigoid, catastrophic antiphospholipid syndrome, celiac disease, cervical spondylosis, chronic ischemia, cicatricial pemphigoid, clinical isolated syndrome with risk for multiple sclerosis, childhood onset psychiatric disorder, dacrocystitis, dermatomyositis, disc herniation, disc prolapse, drug induced immune hemolytic anemia, endophthalmitis, episcleritis, erythema multiforme, erythema multiforme major, gestational pemphigoid, Guillain-Barre syndrome, heart failure, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell hisiocytosis, livedo reticularis, microscopic polyangiitis, morbus bechterev, motor neuron disorders, mucous membrane pemphigoid, primary progressive multiple sclerosis, secondary progressive multiple sclerosis, relapsing remitting multiple sclerosis, multiple organ failure, myelodysplastic syndrome, nerve root disorder, neuropathy, Non-A Non-B hepatitis, osteolysis, ovarian cancer, pauciarticular JRA, peripheral artery occlusive disease (PAOD), peripheral vascular disease (PVD), peripheral artery disease, phlebitis, polychondritis, polymyalgia rheumatica, poliosis, polyarticular JRA, polyendocrine deficiency syndrome, polymyositis, post-pump syndrome, primary parkinsonism, prostatitis, psoratic arthropathy, pure red cell aplasia, primary adrenal insufficiency, Reiter's disease, recurrent neuromyelitis optica, rheumatic heart disease, SAPHO (synovitis, acne, pustulosis, hyperostosis, and osteitis), scleroderma, secondary amyloidosis, shock lung, sciatica, secondary adrenal insufficiency, septic arthritis, seronegative arthopathy, silicone associated connective tissue disease, Sneddon-Wilkinson Dermatosis, spondilitis ankylosans, Stevens-Johnson Syndrome, systemic inflammatory response syndrome, temporal arteritis, toxoplasmic retinitis, toxic epidermal necrolysis, TRAPS (Tumor Necrosis factor receptor), type 1 allergic reaction, type II diabetes, urticaria, usual interstitial pneumonia, vernal conjunctivitis, viral retinitis, Vogt-Koyanagi-Harada syndrome (VKH syndrome) and wet macular degeneration. More particularly, the methods are useful for treating conditions related to pain such as, but not limited to, neuropathic pain, nociceptive pain, inflammatory pain (e.g. osteoarthritic pain, rheumatoid arthritic pain), fibromyalgia, neuralgia such as postherpatic neuralgia and trigeminal neuralgia, diabatic neuropathic pain, HIV-related neuropathic pain, migraine, post-stroke pain, post-operative pain, multiple sclerosis pain, pain related to spinal cord injury, cancer pain, lower back pain, and eye pain; and inflammatory disorders (e.g rheumatoid arthritis, osteoarthritis).

Further provided herein is the use of present compounds or pharmaceutically acceptable salts, solvates, or salts of solvates thereof, in the manufacture of medicaments for the treatment of the diseases or conditions described above, alone or in combination with a pharmaceutically acceptable carrier, particularly for the treatment of pain such as, but not limited to, neuropathic pain, nociceptive pain, inflammatory pain (e.g. osteoarthritic pain, rheumatoid arthritic pain), fibromyalgia, neuralgia such as postherpatic neuralgia and trigeminal neuralgia, diabatic neuropathic pain, HIV-related neuropathic pain, migraine, post-stroke pain, post-operative pain, multiple sclerosis pain, pain related to spinal cord injury, cancer pain, lower back pain, and eye pain.

The compounds, compositions comprising the compounds, and methods for treating or preventing conditions and disorders by administering the compounds are further described herein.

These and other objectives of the invention are described in the following paragraphs. These objectives should not be deemed to narrow the scope of the invention.

DETAILED DESCRIPTION

Compounds of formula (I):

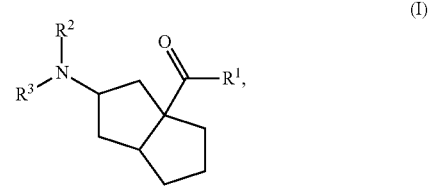

wherein $R^1$, $R^2$, and $R^3$ are as defined above in the Summary and below in the Detailed Description are disclosed. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a straight or branched, saturated hydrocarbon chain, for example, of 1 to 10 carbon atoms or of 1 to 6 carbon atoms ($C_1$-$C_6$ alkylenyl). Examples of alkylene and alkylenyl include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group, as defined herein, of 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The bicyclic aryl is attached to the parent molecular moiety through any carbon atom contained within the bicyclic ring system and can be unsubstituted or substituted.

The term "monocyclic cycloalkyl" as used herein, means a monocyclic carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic cycloalkyl can be unsubstituted or substituted.

The term "monocyclic cycloalkenyl" as used herein, means a monocyclic carbocyclic ring system of four-, five-, six-, seven- or eight carbon atoms, zero heteroatoms, and at least one carbon-carbon double bond. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The monocyclic cycloalkenyl can be unsubstituted or substituted.

The term "halo" or "halogen" as used herein, means Cl, Br, I, and F.

The term "haloalkyl" as used herein, means an alkyl group, as defined herein, in which one, two, three, four, five or six hydrogen atoms are replaced by halogen. The term "$C_1$-$C_6$ haloalkyl" means a $C_1$-$C_6$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl, and trifluoropropyl.

The term "haloalkoxy" as used herein, means an alkoxy group, as defined herein, in which one, two, three, four, five or six hydrogen atoms are replaced by halogen. Representative examples of haloalkoxy include, but are not limited to, 2-fluoroethoxy, 2,2,2-trifluoroethoxy, trifluoromethoxy, and difluoromethoxy.

The term "monocyclic heterocycle" as used herein, means a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, thiopyranyl, and trithianyl. The monocyclic heterocycle can be unsubstituted or substituted. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl (including 1,2,4-oxadiazolyl), 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl (e.g. 1,2,4-triazolyl), and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, phthalazinyl, 2,6-dihydropyrrolo[3,4-c]pyrazol-5(4H)-yl, 6,7-dihydro-pyrazolo[1,5-a]pyrazin-5(4H)-yl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, 2,4,6,7-tetrahydro-5H-pyrazolo[4,3-c]pyridin-5-yl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, and sulfur.

If a moiety is described as "substituted", a non-hydrogen radical is in the place of hydrogen radical any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "modulate" refers to the ability of a compound to increase or decrease the function, or activity, of CCR. "Modulation", as used herein in its various forms, is intended to encompass antagonism, inhibition, agonism, partial antagonism and/or partial agonism of the activity associated with chemokine receptor, CCR. In certain embodiments, the chemokine receptor is CCR2.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

Compounds of formula (I) are as described above.

Particular values of variable groups in compounds of formula (I) are as follows. Such values may be used where appropriate with any of the other values, definitions, claims or embodiments defined hereinbefore or hereinafter.

$R^1$ has values as disclosed in the Summary. In certain embodiments of compounds of formula (I), $R^1$ is formula (a) or formula (b). In certain embodiments, $R^1$ is formula (a) wherein A is $CH_2$. In other embodiments, $R^1$ is formula (b).

$Z^1$ of formula (a) is as disclosed in the Summary and embodiments herein. In certain embodiments, $Z^1$ is —C(O)O(alkyl) (e.g. —C(O)O(tert-butyl)). In other embodiments, $Z^1$ is aryl or heteroaryl. In yet other embodiments, $Z^1$ is aryl (e.g. phenyl). In yet other embodiments, $Z^1$ is heteroaryl (e.g. monocyclic heteroaryl). Examples of the monocyclic heteroaryl of $Z^1$ include, but are not limited to, pyridinyl, pyrimidinyl, pyridazinyl, and thiazolyl.

$Z^2$ of formula (b) is as disclosed in the Summary and embodiments herein. In certain embodiments, $Z^2$ is aryl or heteroaryl. In yet other embodiments, $Z^2$ is heteroaryl (e.g. monocyclic heteroaryl). Examples of the monocyclic heteroaryl of $Z^2$ include, but are not limited to, pyridinyl, pyrimidinyl, pyridazinyl, and thiazolyl. In certain embodiments, $Z^2$ is pyridinyl.

The aryl and heteroaryl rings (including the exemplary rings) of $Z^1$ and $Z^2$ are each independently unsubstituted or substituted. In certain embodiments, the aryl and heteroaryl rings described for $Z^1$ and $Z^2$ are substituted. In yet other embodiments, the aryl and heteroaryl rings described for $Z^1$ and $Z^2$ are substituted with 1 or 2 substituents.

The optional substituents of $Z^1$ and $Z^2$ are as described in the Summary and embodiments herein. For example, the optional substituents of $Z^1$ and $Z^2$ are independently $C_1$-$C_6$ alkyl (e.g. methyl), halogen (e.g. F, Cl), $C_1$-$C_6$ haloalkyl (e.g. trifluoromethyl), CN, or $OR^a$ wherein $R^a$ is $C_1$-$C_6$ alkyl (e.g. methyl) or $C_1$-$C_6$ haloalkyl (e.g. trifluoromethyl).

$R^2$ and $R^3$ are as disclosed in the Summary and embodiments herein. For example, $R^2$ is hydrogen or unsubstituted $C_1$-$C_6$ alkyl (e.g. methyl, ethyl, isopropyl). In certain embodiments, $R^2$ is hydrogen or methyl. In certain embodiments, $R^2$ is hydrogen.

$R^3$ is

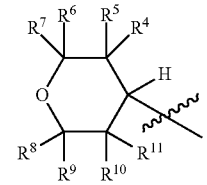

wherein $R^4$, $R^5$, $R^6$, $R^7$, $R^8$, $R^9$, $R^{10}$, and $R^{11}$ are as described in the Summary and embodments herein. For example, in certain embodiments, $R^5$, $R^6$, $R^7$, $R^8$, $R^9$, $R^{10}$, and $R^{11}$ are independently hydrogen or methyl. In yet other embodiments, $R^5$, $R^6$, $R^7$, $R^8$, $R^9$, $R^{10}$, and $R^{11}$ are hydrogen. $R^4$, for example, is $C_1$-$C_6$ alkyl (e.g. methyl, ethyl) or $O(C_1$-$C_6$ alkyl) (e.g. $O(CH_3)$).

In certain embodiments, $R^2$ and $R^3$, together with the nitrogen atom to which they are attached, form a ring of formula (i), (ii), or (iii). In other embodiments, $R^2$ and $R^3$, together with the nitrogen atom to which they are attached, form a ring of formula (i) or (ii). In the embodiments that $R^2$ and $R^3$, together with the nitrogen atom form a ring as represented by formula (i), p, q, and n are as described in the Summary, for example, p and q are 2, and n is 0.

In the embodiments that $R^2$ and $R^3$, together with the nitrogen atom form a ring as represented by formula (i), $G^1$ is as disclosed in the Summary. For example, $G^1$ is optionally substituted aryl such as, but not limited to, optionally substituted phenyl. When $G^1$ is phenyl, it is, for example, optionally substituted with one —C(O)OH group.

In the embodiments that $R^2$ and $R^3$, together with the nitrogen atom form a ring as represented by formula (ii), $R^{13}$, $R^{14}$, $R^{15}$, $R^{16}$, $R^{17}$, $R^{18}$, $R^{19}$, and $R^{20}$, are as disclosed in the Summary. For example, $R^{13}$, $R^{14}$, $R^{15}$, $R^{16}$, $R^{17}$, $R^{18}$, $R^{19}$, and $R^{20}$ are hydrogen.

It is appreciated that compounds of formula (I) with combinations of the above embodiments, including particular, more particular and preferred embodiments are contemplated.

Accordingly, one aspect relates to a group of compounds of formula (I) wherein $R^1$ is formula (a), A is $CH_2$, and $R^3$ is

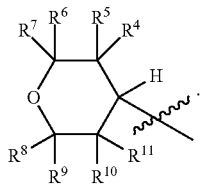

Another aspect relates to a group of compounds of formula (I) wherein $R^1$ is formula (a), A is $CH_2$, $R^3$ is

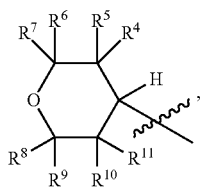

$R^4$ is $C_1$-$C_6$ alkyl (e.g. methyl, ethyl) or $O(C_1$-$C_6$ alkyl) (e.g. $O(CH_3)$), and $R^5$, $R^6$, $R^7$, $R^8$, $R^9$, $R^{10}$, and $R^{11}$ are as described in the Summary and embodiments herein. In certain embodiments, $R^5$, $R^6$, $R^7$, $R^8$, $R^9$, $R^{10}$, and $R^{11}$ are each independently hydrogen or methyl. In other embodiments, $R^5$, $R^6$, $R^7$, $R^8$, $R^9$, $R^{10}$, and $R^{11}$ are hydrogen.

Another aspect is related to a group of compounds of formula (I) wherein $R^1$ is formula (b) and $R^3$ is

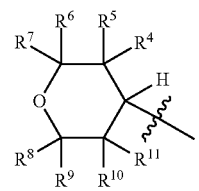

Another aspect is related to a group of compounds of formula (I) wherein $R^1$ is formula (b), $R^3$ is

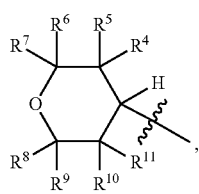

$R^4$ is $C_1$-$C_6$ alkyl (e.g. methyl, ethyl) or $O(C_1$-$C_6$ alkyl) (e.g. $O(CH_3)$), and $R^5$, $R^6$, $R^7$, $R^8$, $R^9$, $R^{10}$, and $R^{11}$ are as described in the Summary and embodiments herein. In certain embodiments, $R^5$, $R^6$, $R^7$, $R^8$, $R^9$, $R^{10}$, and $R^{11}$ are each independently hydrogen or methyl. In other embodiments, $R^5$, $R^6$, $R^7$, $R^8$, $R^9$, $R^{10}$, and $R^{11}$ are hydrogen.

Another aspect relates to a group of compounds of formula (I) wherein $R^1$ is formula (a), A is $CH_2$, and $R^2$ and $R^3$, together with the nitrogen atom to which they are attached, form a ring of formula (i) or (ii).

Another aspect relates to a group of compounds of formula (I) wherein $R^1$ is formula (a), A is $CH_2$, and $R^2$ and $R^3$, together with the nitrogen atom to which they are attached, form a ring of formula (i).

Another aspect relates to a group of compounds of formula (I) wherein $R^1$ is formula (a), A is $CH_2$, $R^2$ and $R^3$, together with the nitrogen atom to which they are attached, form a ring of formula (i), p and q are 2, and n is 0.

Another aspect relates to a group of compounds of formula (I) wherein $R^1$ is formula (a), A is $CH_2$, $R^2$ and $R^3$, together with the nitrogen atom to which they are attached, form a ring of formula (i), p and q are 2, n is 0, and $G^1$ is optionally substituted aryl (e.g. optionally substituted phenyl). In certain embodiments, $G^1$ is phenyl optionally substituted with one —C(O)OH group.

Another aspect relates to a group of compounds of formula (I) wherein $R^1$ is formula (a), A is $CH_2$, and $R^2$ and $R^3$, together with the nitrogen atom to which they are attached, form a ring of formula (ii).

Another aspect relates to a group of compounds of formula (I) wherein $R^1$ is formula (a), A is $CH_2$, $R^2$ and $R^3$, together with the nitrogen atom to which they are attached, form a ring of formula (ii), and $R^{13}$, $R^{14}$, $R^{15}$, $R^{16}$, $R^{17}$, $R^{18}$, $R^{19}$, and $R^{20}$ are hydrogen.

Within each group of compounds of formula (I) as described above, $Z^1$ and $Z^2$ are as described in the Summary and embodiments herein above. Thus, within each group of compounds of formula (I), examples of a subgroup of compounds of formula (I) include, but are not limited to, those wherein $Z^1$ is —C(O)O(alkyl) (e.g. —C(O)O(tert-butyl)).

Other examples of a subgroup include, but are not limited to, those wherein $Z^1$ is aryl or heteroaryl.

Yet other examples of a subgroup include, but are not limited to, those wherein $Z^1$ is an aryl.

Yet other examples of a subgroup include, but are not limited to, those wherein $Z^1$ is a phenyl.

Yet other examples of a subgroup include, but are not limited to, those wherein $Z^1$ is a heteroaryl. In certain embodiments, $Z^1$ is a monocyclic heteroaryl.

Yet other examples of a subgroup include, but are not limited to, those wherein $Z^1$ is pyridinyl, pyrimidinyl, pyridazinyl, or thiazolyl.

Yet other examples of a subgroup include, but are not limited to, those wherein $Z^1$ is pyridinyl.

Yet other examples of a subgroup include, but are not limited to, those wherein $Z^2$ is aryl or heteroaryl.

Yet other examples of a subgroup include, but are not limited to, those wherein $Z^2$ is a heteroaryl. In certain embodiments, $Z^2$ is a monocyclic heteroaryl.

Yet other examples of a subgroup include, but are not limited to, those wherein $Z^2$ is pyridinyl, pyrimidinyl, pyridazinyl, or thiazolyl.

Yet other examples of a subgroup include, but are not limited to, those wherein $Z^2$ is pyridinyl.

Within each of the aforementioned groups and subgroups of compounds of formula (I), $Z^1$ and $Z^2$ are each independently unsubstituted or substituted as described in the Summary and embodiments herein above. For example, $Z^1$ and $Z^2$ are substituted with 1 or 2 substituents described in the Summary and embodiments herein above.

Exemplary compounds of formula (I) include, but are not limited to:

1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{methyl[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-erythro-pentitol;

3-{1-[(2S,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid;

3-{1-[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid;

1,5-anhydro-2,3-dideoxy-4-O-methyl-3-{[(2R,3aR,6aR)-3a-({(1S,4S)-5-[6-methyl-4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-(trifluoromethyl)pyrimidin-2-yl]-2,5-diazabicyclo[2.2.1]hept-2-yl)}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[6-(trifluoromethyl)pyrimidin-4-yl]-2,5-diazabicyclo[2.2.1]hept-2-yl)}carbonyl)octahydropentalen-2-yl]amino}-D-erythro-pentitol;

1,5-anhydro-2,3-dideoxy-3-{[(2R,3aR,6aR)-3a-({(1S,4S)-5-[2-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-3-{[(2R,3aR,6aR)-3a-({(1S,4S)-5-[4-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[2-methyl-5-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[2-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[3-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-methyl-3-(trifluoromethyl)phenyl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-{[(1S,4S)-5-(3-chloro-4-fluorophenyl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-2,3-dideoxy-3-{[(2R,3aR,6aR)-3a-({(1S,4S)-5-[3-fluoro-4-(trifluoromethyl)pyridin-2-yl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[6-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[2-methyl-3-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[3-methyl-5-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[3-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[2-(trifluoromethyl)pyridin-4-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[2-(trifluoromethyl)pyrimidin-4-yl]-2,5-diazabicyclo[2.2.1]hept-2-yl)}carbonyl)octahydropentalen-2-yl]amino}-D-erythro-pentitol;

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-(trifluoromethoxy)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-(trifluoromethyl)-1,3-thiazol-2-yl]-2,5-diazabicyclo[2.2.1]hept-2-yl)}carbonyl)octahydropentalen-2-yl]amino}-D-erythro-pentitol;

1,5-anhydro-2,3-dideoxy-3-{[(2R,3aR,6aR)-3a-({(1S,4S)-5-[4-methoxy-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-3-{[(2R,3aR,6aR)-3a-({(1S,4S)-5-[3-chloro-5-(trifluoromethyl)pyridin-2-yl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[5-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-{[(1S,4S)-5-(2-chloropyridin-4-yl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-3-{[(2R,3aR,6aR)-3a-({(1S,4S)-5-[5-cyano-2-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-cyano-2-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-methyl-4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-({(1S,4S)-5-[4-cyano-3-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-2,3-dideoxy-3-{[(2R,3aR,6aR)-3a-{[(1S,4S)-5-(3,4-dichlorophenyl)-2,5-diazabicyclo[2.2.1]hept-2-yl]carbonyl}octahydropentalen-2-yl]amino}-4-O-methyl-D-erythro-pentitol;

1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-threo-pentitol;

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl)}carbonyl)octahydropentalen-2-yl]amino}-2,3-dideoxy-4-O-methyl-D-erythro-pentitol;

1,5-anhydro-3-{[(2R,3aR,6aR)-3a-{[(1S,4S)-5-(4-chloro-3-cyanophenyl)-2,5-diazabicyclo[2.2.1]hept-2-yl]carbonyl}octahydropentalen-2-yl]amino}-2,3-dideoxy-4-O-methyl-D-erythro-pentitol;

2-[(1S,4S)-5-{[(2R,3aR,6aR)-2-(4-phenylpiperidin-1-yl)hexahydropentalen-3a(1H)-yl]carbonyl}-2,5-diazabicyclo[2.2.1]hept-2-yl]-4-(trifluoromethyl)benzonitrile;

[(2R,3aR,6aR)-2-(4-phenylpiperidin-1-yl)hexahydropentalen-3a(1H)-yl]{(1S,4S)-5-[4-(trifluoromethyl)pyridin-2-yl]-2,5-diazabicyclo[2.2.1]hept-2-yl}methanone;

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl)}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl)}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl)}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[4-cyano-3-(trifluoromethyl)phenyl]-2,5-diazabicyclo[2.2.1]hept-2-yl)}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl)}carbonyl)octahydropentalen-2-yl](methyl)amino}-2,3-dideoxy-4-O-methyl-D-erythro-pentitol;

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl](methyl)amino}-2,3-dideoxy-4-O-methyl-D-erythro-pentitol;

[(2R,3aR,6aR)-2-(morpholin-4-yl)hexahydropentalen-3a(1H)-yl]{(1S,4S)-5-[4-(trifluoromethyl)pyridin-2-yl]-2,5-diazabicyclo[2.2.1]hept-2-yl}methanone;

1,5-anhydro-3-{[(2R,3aR,6aR)-3a-{[(1S,4S)-5-(tert-butoxycarbonyl)-2,5-diazabicyclo[2.2.1]hept-2-yl]carbonyl}octahydropentalen-2-yl]amino}-2,3-dideoxy-4-O-methyl-D-erythro-pentitol;

[(2R,3aR,6aR)-2-{[(3R,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3R,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4S)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone; and

[(2R,3aR,6aR)-2-{[(3S,4R)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone.

Compounds of formula (I) contain one or more chiral centers, and can exist in different optically active forms. When compounds of formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support (for example silica with a bound chiral ligand) or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula (I) contains more than one chiral center, it may exist in diastereoisomeric forms. The diastereoisomeric compounds may be separated by methods known to those skilled in the art, for example chromatography or crystallization. The present invention includes each diastereoisomer of compounds of formula (I) and mixtures of various ratios thereof.

Certain compounds of formula (I) may exist in different tautomeric forms or as different geometric isomers, and the present invention includes all tautomers and/or geometric isomers of compounds of formula (I) and mixtures thereof.

Though structural representations within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within drawings or the naming of the compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CCR2 modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

In addition, non-radioactive isotope-containing drugs, such as deuterated drugs called "heavy drugs," can be used for the treatment of diseases and conditions related to the modulation of CCR2 function. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physico-chemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions, potentially altering the pharmacokinetic profile or efficacy relative to the non-isotopic compound.

c. Biological Data (i) In Vitro Assay:

The in vitro potency of compounds in antagonizing CCR2 discussed herein or described in the art may be determined by the procedures detailed below.

CHO cells expressing human CCR2B were generated as follows. cDNA for human CCR2B (cloned from human blood) was cloned into plasmid pcDNA3.1 (from Invitrogen). The resulting plasmids were separately transfected into CHO cells expressing human Gα16 (from Molecular Devices). Sequences of the transfected CCR2 open reading frames in the resulting cell lines were identical to human CCR2B (NM_00648). CHO cells expressing rat CCR2 were generated as follows. cDNA for rat CCR2 (cloned from rat macrophage) was cloned into plasmid pEF-flag (from Chinese Academy of Science). The resulting plasmids were transfected into CHO cells expressing human Gα16 (from Abbott). Sequences of the transfected CCR2 open reading frames in the resulting cell lines were identical to rat CCR2 (NM_021866.1).

Inhibition of [$^{125}$I]-Labeled MCP-1 Binding to hCCR2B

Radioligand binding assays were performed in CHO cells expressing human CCR2B and Gα16 coupling protein. All compounds were dissolved in DMSO and assays run at a final DMSO concentration of 0.5% (v/v). [$^{125}$I]-labeled human MCP-1 was purchased from PerkinElmer. Unlabelled human MCP-1 was purchased from PeproTech.

Compounds were serially diluted in DMSO before diluting into assay buffer (25 mM HEPES, pH 7.4, 5 mM MgCl$_2$, 1 mM CaCl$_2$, 0.5% BSA) with cryo preserved CHO cells expressing human CCR2B and the Gα16 coupling protein (30×10$^3$/well) and [$^{125}$I]-MCP-1 (50 pM). The reaction was incubated at room temperature for 90 minutes before transferring to GF/C filter membrane (PerkinElmer) pre-treated with 0.3% polyethyleneimine for 2 hours at 4° C. The filter membrane was washed six times with ice cold wash buffer (25 mM HEPES, pH 7.4, 5 mM MgCl$_2$, 1 mM CaCl$_2$, 500 mM NaCl, 0.01% (m/v) azide), dried, and sealed in a RLB sample bag (Agilent Technologies) before adding 5.0 mL Microscint 20 to each bag. Membrane was counted on Microbeta counter where background binding was determined by the presence of 100 nM MCP-1 and control total binding was determined by addition of DMSO in place of the test compound. The radioactivity values (cpm) were used to calculate the percent inhibition at a given compound concentration and the data fit to a sigmoidal curve in a semi-log plot to determine IC$_{50}$ values. The corresponding K$_i$ value is calculated as follows: K$_i$=IC$_{50}$/(1+[radioligand]/K$_d$), where [radioligand] is the concentration of the label and K$_d$ (dissociation constant) is determined in saturation experiment with different concentrations of labeled MCP-1. The mean values of K$_i$ of compounds tested are presented in Table 1.

TABLE 1

| Example # | hCCR2B K$_i$ (μM) |
|---|---|
| 1 | 0.032 |
| 2 | 0.060 |
| 5 | 0.104 |
| 6 | 0.028 |
| 7 | 0.030 |
| 12 | 0.261 |
| 13 | 0.593 |
| 14 | 0.031 |
| 15 | 0.029 |
| 16 | 0.199 |
| 18 | 0.207 |
| 19 | 0.306 |
| 20 | 0.112 |
| 22 | 0.120 |
| 25 | 0.271 |
| 26 | 0.792 |
| 27 | 0.444 |
| 28 | 0.032 |
| 29 | 0.473 |
| 30 | 0.831 |
| 32 | 1.060 |
| 36 | 1.060 |
| 39 | 0.066 |
| 40 | 0.038 |
| 46 | 0.017 |
| 47 | 0.077 |
| 48 | 0.008 |
| 49 | 0.015 |
| 50 | 0.078 |
| 51 | 0.021 |
| 52 | 0.049 |
| 53 | 0.016 |
| 56 | 0.032 |
| 60 | 0.552 |
| 61 | 0.069 |
| 63 | 0.010 |
| 64 | 0.012 |
| 65 | 0.006 |
| 66 | 0.013 |

Inhibition of Native Agonist-Induced Intracellular Calcium Release in Cells Expressing hCCR2B or rCCR2

Calcium flux assays were performed in CHO cells expressing human CCR2B and Gα16 coupling protein, or rat CCR2 and Gα16 coupling protein. All compounds were dissolved in DMSO and assays run at a final DMSO concentration of 0.25% (v/v). Human MCP-1 was purchased from PeproTech and used at a final assay concentration of 2 nM, while rat MCP-1 was purchased from R&D and used at a final assay concentration of 4 nM. Assays with cells expressing human CCR2B were performed with human MCP-1, while assays with cells expressing rat CCR2 were performed with rat MCP-1.

Briefly, cells were cultured overnight in a microtiter plate at 8000 per well. The next day, the resultant adherent cells were incubated in assay buffer (20 mM HEPES, pH 7.4, 0.1% bovine serum albumin, and 2.5 mM probenocid in Hank's Buffered Saline Solution) containing Calcium 4 dye (Molecular Probes) at 37° C. for 60 minutes. Calcium flux assays were performed on a FLIPR$^{Tetra}$ instrument (Molecular Devices) by adding compound to the cells followed by addition of native agonist and measuring the change in fluorescence as a function of time. Maximal and minimal values for fluorescence were determined using native agonist (2 nM MCP-1) for human or rat CCR2, or buffer addition, respectively. Fluorescence values were used to calculate the percent inhibition at a given compound concentration and the data fit to a sigmoidal curve in a semi-log plot to determine IC$_{50}$ values. The K$_b$ value is calculated as K$_b$=IC$_{50}$/(1+[agonist]/EC$_{50}$), where [agonist] is the concentration of agonist used and EC$_{50}$ is the agonist potency determined in the previous experiments. Mean K$_b$ values and IC$_{50}$ of the compounds assayed are reported in Table 2 and Table 3 respectively.

TABLE 2

| Example# | rCCR2 K$_b$ (μM) | hCCR2B K$_b$ (μM) |
|---|---|---|
| 1 | 0.023 | 0.014 |
| 2 | 0.012 | 0.019 |
| 3 | 0.694 | 0.614 |
| 4 | >6.94 | >6.14 |
| 5 | 0.007 | 0.034 |
| 6 | 0.029 | 0.008 |
| 7 | 0.010 | 0.016 |

TABLE 2-continued
| Example# | rCCR2 $K_b$ (μM) | hCCR2B $K_b$ (μM) |
|---|---|---|
| 8 | >6.94 | >3.55 |
| 9 | 0.022 | 0.116 |
| 10 | 0.038 | 0.394 |
| 11 | 0.074 | 0.359 |
| 12 | 0.011 | 0.048 |
| 13 | 0.024 | 0.129 |
| 14 | 0.004 | 0.011 |
| 15 | 0.003 | 0.009 |
| 16 | 0.007 | 0.026 |
| 17 | 0.160 | 0.316 |
| 18 | 0.006 | 0.019 |
| 19 | 0.012 | 0.057 |
| 20 | 0.018 | 0.045 |
| 21 | 0.091 | 0.201 |
| 22 | 0.012 | 0.038 |
| 23 | 0.158 | 0.272 |
| 24 | 0.116 | 0.341 |
| 25 | 0.005 | 0.023 |
| 26 | 0.022 | 0.147 |
| 27 | 0.019 | 0.096 |
| 28 | 0.005 | 0.005 |
| 29 | 0.008 | 0.036 |
| 30 | 0.004 | 0.023 |
| 31 | 0.022 | 0.250 |
| 32 | 0.044 | 0.077 |
| 33 | >1.33 | >6.14 |
| 34 | 0.342 | 0.682 |
| 35 | 0.240 | 0.682 |
| 36 | 0.024 | 0.075 |
| 37 | 0.248 | 0.393 |
| 38 | 0.317 | 0.394 |
| 39 | 0.003 | 0.014 |
| 40 | 0.003 | 0.010 |
| 41 | >4 | >6.14 |
| 42 | 0.026 | 0.199 |
| 43 | 0.053 | 0.373 |
| 44 | 0.486 | 0.394 |
| 45 | 0.532 | 0.542 |
| 46 | 0.003 | 0.004 |
| 47 | 0.004 | 0.012 |
| 48 | 0.017 | 0.013 |
| 49 | 0.023 | 0.009 |
| 50 | 0.006 | 0.006 |
| 51 | 0.029 | 0.011 |
| 52 | 0.038 | 0.021 |
| 53 | 0.026 | 0.012 |
| 54 | 2.310 | 0.682 |
| 55 | 0.175 | 0.346 |
| 56 | 0.009 | 0.011 |
| 57 | 0.055 | 0.128 |
| 58 | 0.515 | 0.684 |
| 59 | 0.533 | 0.204 |
| 60 | 0.019 | 0.081 |
| 61 | 0.030 | 0.025 |
| 62 | 0.055 | 0.109 |
| 63 | 0.006 | 0.004 |
| 64 | 0.009 | 0.004 |
| 65 | 0.008 | 0.007 |
| 66 | 0.008 | 0.011 |
TABLE 3
| Example # | hCCR2B $IC_{50}$ (μM) |
|---|---|
| 1 | 0.0549 |
| 2 | 0.0767 |
| 3 | 2.5 |
| 4 | 25.0 |
| 5 | 0.14 |
| 6 | 0.0328 |
| 7 | 0.0657 |
| 8 | 14.43 |
| 9 | 0.47 |
| 10 | 1.6 |
| 11 | 1.47 |
| 12 | 0.194 |
| 13 | 0.525 |
| 14 | 0.043 |
| 15 | 0.0347 |
| 16 | 0.106 |
| 17 | 1.29 |
| 18 | 0.0764 |
| 19 | 0.233 |
| 20 | 0.182 |
| 21 | 0.821 |
| 22 | 0.153 |
| 23 | 1.11 |
| 24 | 1.39 |
| 25 | 0.0922 |
| 26 | 0.598 |
| 27 | 0.391 |
| 28 | 0.0198 |
| 29 | 0.148 |
| 30 | 0.0955 |
| 31 | 1.02 |
| 32 | 0.314 |
| 33 | 25.0 |
| 34 | 2.78 |
| 35 | 2.78 |
| 36 | 0.305 |
| 37 | 1.6 |
| 38 | 1.6 |
| 39 | 0.0553 |
| 40 | 0.0415 |
| 41 | 25.0 |
| 42 | 0.812 |
| 43 | 1.52 |
| 44 | 1.6 |
| 45 | 2.2 |
| 46 | 0.0176 |
| 47 | 0.0498 |
| 48 | 0.0518 |
| 49 | 0.037 |
| 50 | 0.0259 |
| 51 | 0.0433 |
| 52 | 0.0839 |
| 53 | 0.0479 |
| 54 | 2.78 |
| 55 | 1.41 |
| 56 | 0.046 |
| 57 | 0.521 |
| 58 | 2.78 |
| 59 | 0.83 |
| 60 | 0.328 |
| 61 | 0.100 |
| 62 | 0.445 |
| 63 | 0.0179 |
| 64 | 0.0165 |
| 65 | 0.028 |
| 66 | 0.0458 |
| Compound A | >50 |
| Compound B | 28 |
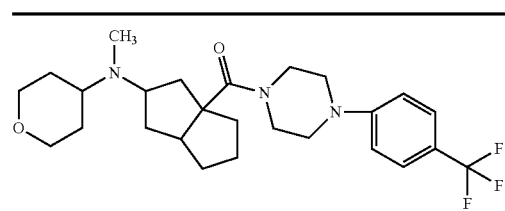
Compound A TABLE 3-continued

| Example # | hCCR2B IC$_{50}$ (µM) |
|---|---|

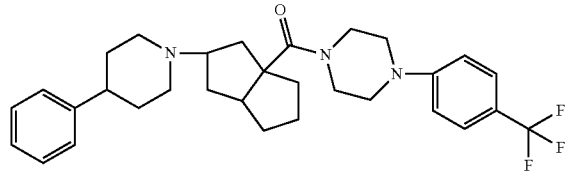

Compound B

The data in the above tables demonstrate that present compounds when tested with the aforementioned assays, have activity in binding to the CCR2 receptor, indicating the intrinsic activity of the compounds in use as modulators of chemokine receptor activity.

d. Methods of Using the Compounds

In one aspect, the invention provides a method for antagonizing CCR2 in a subject (e.g. human) suffering from a disorder in which CCR2 activity is detrimental, comprising administering to the subject a compound of formula (I) or a pharmaceutical composition comprising the same, such that CCR2 activity in the human subject is inhibited and treatment is achieved.

Many autoimmune diseases and disease associated with chronic inflammation, as well as acute responses, have been linked to activation of CCR2. The present compounds are useful in the treatment of inflammatory disorders including, but not limited to rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus.

The present compounds and the pharmaceutical compositions comprising the same are also useful in the treatment of cardiovascular disorders, such as acute myocardial infarction, acute coronary syndrome, chronic heart failure, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

Compounds described herein and pharmaceutical compositions comprising a therapeutically effective amount thereof are useful in the treatment of a disorder selected from the group comprising CNS system disorders, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjigren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2

Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), H is bundle arrythmias, HIV infection/HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis,* myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as edema, ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as glomerulonephritis, diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, age-related macular degeneration or a central nervous system disorder. In addition, these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Another aspect relates to a method for the treatment of pain such as, but not limited to, neuropathic pain, nociceptive pain, inflammatory pain, osteoarthritic pain, fibromyalgia, neuralgia such as post herpetic neuralgia and trigeminal neuralgia, diabatic neuropathic pain, HIV-related neuropathic pain, migraine, post-stroke pain, post-operative pain, multiple sclerosis pain, pain related to spinal cord injury, cancer pain, lower back pain, and eye pain, comprising administering to a subject in need of such treatment compounds or pharmaceutical compositions described herein.

Present compounds can be used alone or in combination with an additional therapeutic agent to treat such diseases, said additional agent being selected by the skilled artisan for its intended purpose. For example, the additional agent can be a therapeutic agent recognized as being useful to treat the disease or condition being treated by the compounds described herein.

It should further be understood that the combinations which are to be included within this invention are those combinations useful for their intended purpose. The agents set forth below are for illustrative purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

For example, in the treatment or prevention of inflammation or pain, the present compounds may be used in conjunction or combination with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextromethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the present compounds is preferred. Accordingly, the pharmaceutical compositions include those that also contain one or more other active ingredients, in addition to a compound of formula (I). Examples of other active ingredients that may be combined with a present compound, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta.2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib (Celebrex) and rofecoxib (Vioxx®); (h) inhibitors of phosphodiesterase type IV (PDE-IV); (i) gold compounds such as auranofin and aurothioglucose, (j) inhibitors of phosphodiesterase type IV (PDE-IV); (k) other antagonists of the chemokine receptors, especially CCR1, CCR2, CCR3, CCR5, CCR6, CCR8 and CCR10; (l) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (m) anti-diabetic agents such as insulin, sulfonylureas, biguanides (metformin), α-glucosidase inhibitors (acarbose) and glitazones (troglitazone and pioglitazone); (n) preparations of interferon beta (interferon β-1α; interferon β-1b); (o) etanercept (Enbrel®), (p) antibody therapies such as orthoclone (OKT3), daclizumab (Zenapax®), infliximab (Remicade®), basiliximab (Simulect®) and anti-CD40 ligand antibodies (e.g., MRP-1); and (q) other compounds such as 5-aminosalicylic acid and pro-drugs thereof, hydroxychloroquine, D-penicillamine, antimetabolites such as azathioprene and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Immunosuppressants within the scope of the present invention further include, but are not limited to, leflunomide, RAD001, ERL080, FTY720, CTLA-4, antibody therapies such as orthoclone (OKT3), daclizumab (Zenapax®) and basiliximab (Simulect®), and antithymocyte globulins such as thymoglobulins.

The present methods are also directed to the treatment or prevention of multiple sclerosis using a compound of the invention either alone or in combination with a second therapeutic agent selected from betaseron, avonex, azathioprene (Imurek®, Imuran®), capoxone, prednisolone and cyclophosphamide. When used in combination, the practitioner can administer a combination of the therapeutic agents, or administration can be sequential.

In still other embodiments, the present methods are directed to the treatment or prevention of rheumatoid arthritis, wherein the compound of the invention is administered either alone or in combination with an additional therapeutic agent selected from the group consisting of methotrexate, sulfasalazine, hydroxychloroquine, cyclosporine A, D-penicillamine, infliximab (Remicade®), etanercept (Enbrel®), adalimumab (Humira®), auranofin and aurothioglucose.

In yet other embodiments, the present methods are directed to the treatment or prevention of an organ transplant condition wherein the compound of the invention is used alone or in combination with an additional therapeutic agent selected from the group consisting of cyclosporine A, FK-506, rapamycin, mycophenolate, prednisolone, azathioprene, cyclophosphamide and an antilymphocyte globulin.

Present compounds can also be combined with a nonsteroidal anti-inflammatory drug(s) also referred to as NSAIDS which include drugs like ibuprofen. Other combinations are corticosteroids including prednisolone; the well known side-effects of steroid use may be reduced or even eliminated by tapering the steroid dose required when treating patients in combination with the CCR2 antagonists. Non-limiting examples of an additional therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA®), (U.S. Pat. No. 6,090,382), CA2 (REMICADE™), CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

Present compounds may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors;

mesalamine; olsalazine; balsalazide; antioxidants; thromboxane inhibitors; IL-receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK, IKK, or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (I) can be combined include the following: TNF antagonists, for example, anti-TNF antibodies, D2E7 (U.S. Pat. No. 6,090,382; HUMIRA®), CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water, hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which present compounds can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen Idec); anti-α4 antibody (Tysabri®; Biogen Idec); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®); Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-10 converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-RI, sIL-1RII, sIL-6R) and antiinflammatory cytokines (e.g. IL-4, IL-10, IL-13 and TGFβ).

Preferred examples of therapeutic agents for multiple sclerosis in which a compound of Formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

Present compounds may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of formula (I) can be combined include the following: D2E7 (U.S. Pat. No. 6,090, 382; HUMIRA®), ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of formula (I) can be combined include the following: Letairs™ (ambrisentan), albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (RR)-formoterol, TgAAT, cilomilast and roflumilast.

Non-limiting examples of therapeutic agents for HCV with which a compound of formula (I) can be combined include the following: Interferon-alpha-2a, Interferon-alpha-2b, Interferon-alpha con1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of formula (I) can be combined include the following: D2E7 (U.S. Pat. No. 6,090,382; HUMIRA®), methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of formula (I) can be combined include the following: sirolimus, paclitaxel, everolimus, tacrolimus, ABT-578, and acetaminophen.

Non-limiting examples of therapeutic agents for sciatica with which a compound of formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA®), CA2 (REMICADE™), CDP 571, TNFR-Ig constructs, (p75TNFRIgG (ENBREL™) and p55TNFRIgG (LENERCEPT™)).

e. Pharmaceutical Compositions

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions may be manufactured in a manner that is itself known, e.g., by means of conventional mixing, dissolving, granulating, dragee-making, levigating, emulsifying, encapsulating, entrapping or lyophilizing processes. Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds may be delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given CCR2 activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit CCR2 signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the CCR2 modulating effects, or minimal effective concentration (MEC). The MEC will vary for each compound but can be estimated from in vitro data; e.g. the concentration necessary to achieve 50-90% inhibition of CCR2 using the assays described herein. Dosages necessary to achieve the MEC will depend on individual characteristics and route of administration. However, HPLC assays or bioassays can be used to determine plasma concentrations.

Dosage intervals may also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the compounds listed in the Examples section.

i) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

ii) Tablets

Tablets can be prepared, for example, from the following ingredients.

Parts by Weight

| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

iii) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

iv) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional therapeutic agents the treatment of pain. The compounds of the invention can be administered prior to, subsequent to or simultaneously with the additional therapeutic agent, whichever course of administration is appropriate. The compounds of the invention and the additional therapeutic agents act either additively or synergistically. Thus, the administration of such a combination of substances for the treatment of pain can provide greater relief from the deleterious effects of pain than the administration of either substance alone.

A "therapeutically effective amount" is an amount of a compound of formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds and their salts may exist in more than one crystal form and the present invention includes each crystal form and mixtures thereof.

Certain compounds and their salts may also exist in the form of solvates, for example hydrates, and the present invention includes each solvate and mixtures thereof.

Certain compounds may exist in zwitterionic form and the present invention includes each zwitterionic form and mixtures thereof.

As used herein the term "pro-drug" refers to an agent which is converted into the parent drug in vivo by some physiological chemical process (e.g., a pro-drug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the pro-drug is enzymatically or chemically cleaved to deliver the ultimate drug in the blood or tissue.

f. General Synthesis

Compounds described herein when prepared by synthetic processes or by metabolic processes are encompassed in this application. Preparation of the compounds by metabolic processes includes those occurring in the human or animal body (in vivo) or processes occurring in vitro.

Compounds described herein can be prepared using readily available starting materials or known intermediates. The compounds and the intermediates can be prepared by a variety of processes well known for the preparation of compounds of this class. For example, the compounds of formula (I) wherein the groups $X^1$, $X^2$, $X^3$, $R^4$, $R^5$, and formulae (a), (b), and (c) have the meanings as set forth in the Summary and Detailed Description sections unless otherwise noted, can be synthesized, for example, as provided in Schemes 1 and 2.

Abbreviations which have been used in the descriptions of the Schemes and the Examples that follow are: $(Boc)_2O$ for di-tert-butyl dicarbonate, $DMSO-d_6$ for deuterated dimethyl sulfoxide, DMAP for 4-(dimethylamino)pyridine, DMF for N,N-dimethylformamide, EDCI or EDC for 1-ethyl-3-[3-(dimethylamino)propyl]-carbodiimide hydrochloride, EtOAc for ethyl acetate, $Et_3N$ for triethylamine, EtOH for ethanol, HPLC for high-performance liquid chromatography, MeOH for methanol, OMs for methane sulfonate, $Pd_2(dba)_3$ for tris(dibenzylideneacetone)dipalladium(0), TFA for trifluoroacetic acid, THF for tetrahydrofuran, and TLC for thick layer chromatography.

Compounds of formula (5) wherein ring A is as defined as $R^1$, can be prepared, for example, using the general method outlined in Scheme 1.

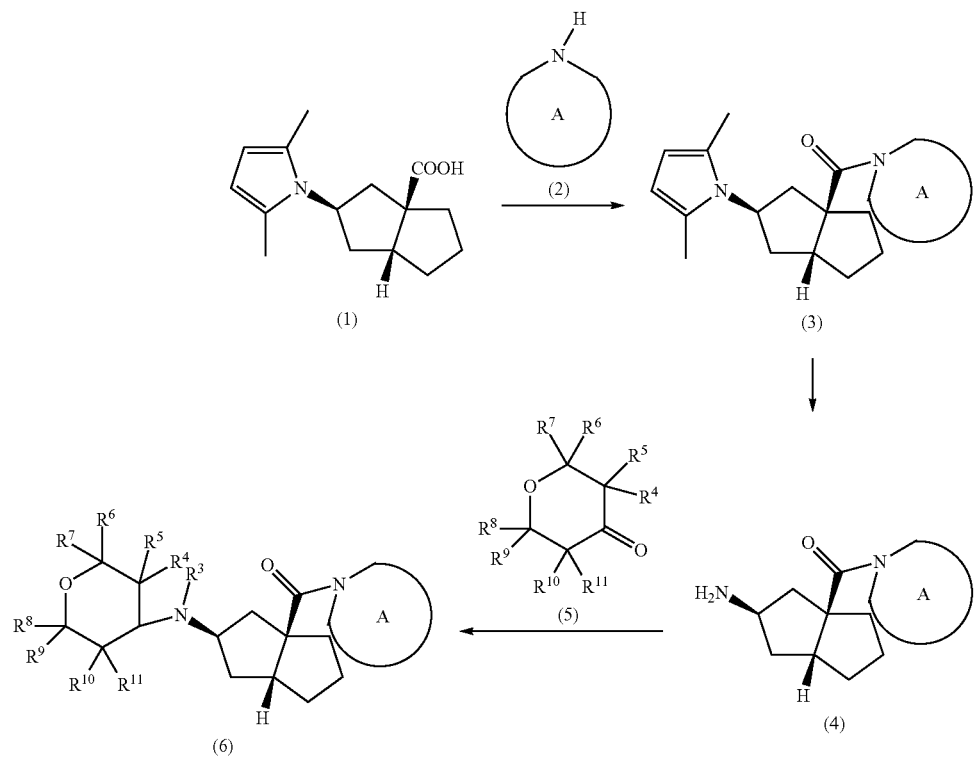

Acid of formula (1) can be treated with amines of formula (2) under coupling conditions known to one skilled in the art, to provide compounds of formula (3). Typical conditions for the coupling reaction include stirring about equimolar mixture of the compounds in a solvent such as, but not limited to, THF, N,N-dimethylacetamide, N,N-dimethylformamide, pyridine, chloroform, or mixture thereof, with a coupling reagent, optionally along with a coupling auxiliary, and in the presence or absence of a base. Typical reactions can be carried out at temperature ranging from about 0° C. to about 65° C. or may be carried out in a microwave reactor to facilitate the coupling. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non-limiting examples of coupling auxiliary include 1-hydroxy-7-azabenzotriazole (HOAT) and 1-hydroxybenzotriazole hydrate (HOBT). Suitable examples of bases include, but are not limited to, N-methyl morpholine and diisopropylethylamine.

Conversion of (3) to the amines of formula (4) can be achieved by treatment with hydroxylamine at elevated temperature. Reductive amination of (4) with cyclic ketones of formula (5) affords compounds of formula (6) wherein $R^2$ is hydrogen. The amines of formula (5) wherein $R^2$ is hydrogen can be alkylated to those wherein $R^2$ is $C_1$-$C_6$ alkyl, alkoxyalkyl, or haloalkoxyalky in the presence of an appropriate base (e.g. diisopropylethyl amine) and $R^2$OMs at about room temperature.

Compounds of general formula (8) wherein ring B is the cyclic amines of formula (a), (b), or (c), can be synthesized using general procedure as illustrated in Scheme 2.

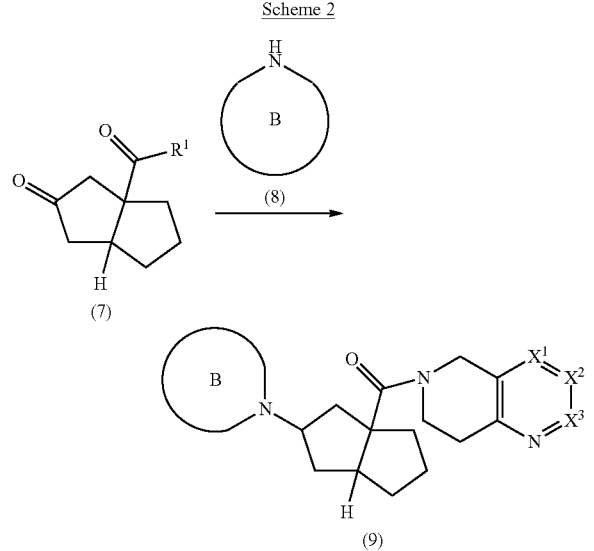

Scheme 2

Transformation of ketones (7) to amines of formula (9) can be achieved by treatment with amines (8) via reductive amination conditions known to one skilled in the art.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

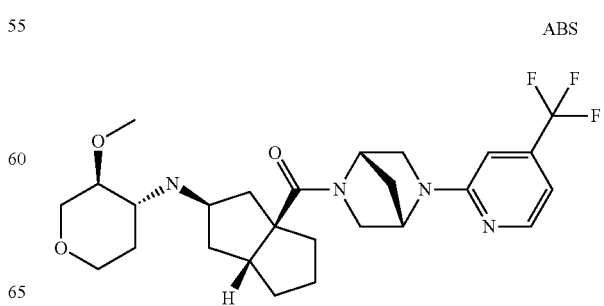

ABS

Example 1

1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-threo-pentitol

Example 1A (1R,4S)-methyl 4-aminocyclopent-2-enecarboxylate

To a cooled mixture of (1R,4S)-2-azabicyclo[2.2.1]hept-5-en-3-one (13 g, 119 mmol) in methanol (150 mL) at 0° C. was added thionyl chloride (20 mL, mmol) dropwise, keeping the reaction temperature under 15° C. Upon completion of the addition, the reaction mixture was stirred at 5° C. for 3 hours. The solvent was removed under reduced pressure, and the product was dried in vacuo to give Example 1A as a hydrochloride salt.

Example 1B (1R,4S)-methyl 4-(2,5-dimethyl-1H-pyrrol-1-yl)cyclopent-2-enecarboxylate To a mixture of Example 1A (23 g, 163 mmol) in methanol (100 ml) was added N-ethyldiisopropylamine (23 g, 179 mmol) and acetyl acetone (20 g, 170 mmol). The mixture was stirred at room temperature for 16 hours. The solvent was removed under reduced pressure, and the crude product was purified by column chromatography (SiO$_2$, petroleum ether:ethyl acetate=20:1) to give Example 1B.

Example 1C (1R,4S)-methyl 1-(3-bromopropyl)-4-(2,5-dimethyl-1H-pyrrol-1-yl)cyclopent-2-enecarboxylate To a solution of Example 1B (16.5 g, 74.4 mmol) in tetrahydrofuran (200 ml) was added dropwise lithium hexamethyl bis(trimethylsilyl)amide (1 M in tetrahydrofuran, 119 mL) at −50° C. The reaction mixture was stirred for 1 hour at the same temperature. 1,3-Dibromopropane (150 g, 744 mmol) was added dropwise over 1 hour. The reaction mixture was allowed to warm to −20° C. and stirred at the same temperature for 1 hour. LCMS showed that the reaction was complete. The reaction mixture was quenched with an aqueous ammonium chloride solution (6%, 600 mL), and extracted with ethyl acetate. The organic fraction was washed with aqueous ammonium chloride (6%), brine, dried with sodium sulfate, filtered, and concentrated in vacuo. The residue was purified by silica gel column chromatography (petroleum ether:ethyl acetate=80:1) to give Example 1C.

Example 1D (2R,3aR,6aR)-methyl 2-(2,5-dimethyl-1H-pyrrol-1-yl)octahydropentalene-3a-carboxylate To a solution of compound 1C (16 g, 47 mmol) and azobisisobutyronitrile (1.6 g, 10 mmol) in toluene (1.8 L) at 110° C. was added a solution of tributyltinhydride (32 mL, 119 mmol) in toluene (200 mL) over 1 hour. After refluxing for 3 hours, the reaction mixture was quenched with a saturated aqueous potassium fluoride solution (200 mL), and extracted with ethyl acetate. The organic fraction was washed with brine, dried with sodium sulfate, filtered, and concentrated in vacuo. The residue was purified by column chromatography (SiO$_2$, petroleum ether:ethyl acetate=50:1) to give Example 1D.

Example 1E (2R,3aR,6aR)-2-(2,5-dimethyl-1H-pyrrol-1-yl)octahydropentalene-3a-carboxylic acid To a solution of Example 1D (5.3 g, 20.3 mmol) in methanol (33 mL) and water (15 mL) was added a aqueous solution of sodium hydroxide (3.2 g, 80 mmol in 4 mL of water) and the mixture was heated at 65° C. for 16 hours. The mixture was cooled to room temperature, acidified to pH=4 with 4N hydrochloric acid. The solid was filtered to afford Example 1E which was used in next step without further purification.

Example 1F (1S,4S)-2-(4-(trifluoromethyl)pyridin-2-yl)-2,5-diazabicyclo[2.2.1]heptane To a mixture of (1S,4S)-tert-butyl 2,5-diazabicyclo[2.2.1]heptane-2-carboxylate (0.6 g, 3.03 mmol) in DMF (5 mL) was added 2-chloro-4-trifluoromethylpyridine (0.2 g, 1.1 mmol) and triethylamine (0.22 g, 2.2 mmol). The reaction mixture was heated at reflux for 1 hour in a microwave reactor at 80° C. Then the solvent was evaporated in vacuo. The crude product was purified by column chromatography on silica gel with eluent (petroleum ether:ethyl acetate from 50:1 to 10:1) to afford the intermediate (1S,4S)-tert-butyl 5-(4-(trifluoromethyl)pyridin-2-yl)-2,5-diazabicyclo[2.2.1]heptane-2-carboxylate (0.1 g).

A mixture of the above intermediate (0.1 g, 0.29 mmol) and a HCl solution (4N, 10 mL) in 1,4-dioxane was stirred at room temperature overnight. The solvents were evaporated in vacuo. The crude product as hydrochloride salt was used in the next step without purification.

Example 1G ((2R,3aR,6aR)-2-(2,5-dimethyl-1H-pyrrol-1-yl)octahydropentalen-3a-yl)((1S,4S)-5-(4-(trifluoromethyl)pyridin-2-yl)-2,5-diazabicyclo[2.2.1]heptan-2-yl)methanone To a solution of compound Example 1E (3.0 g, 12.1 mmol) in dichloromethane (50 mL) was added Example 1F, hydroxybenzotriazole (2.5 g, 18.2 mmol), 1-ethyl-3-(3-dimethylaminopropyl)carbodiimide hydrochloride (3.5 g, 18.2 mmol), and triethyl amine (5.5 g, 54.6 mmol). The reaction mixture was stirred at room temperature for 15 hours. The reaction mixture was suspended in water and extracted with dichloromethane (3×300 mL). The combined organic fractions were washed with brine, dried with sodium sulfate, filtered, and concentrated in vacuo to afford Example 1F, which was used in the next step without further purification.

Example 1H ((2R,3aR,6aR)-2-aminooctahydropentalen-3a-yl)((1S,4S)-5-(4-(trifluoromethyl)pyridin-2-yl)-2,5-diazabicyclo[2.2.1]heptan-2-yl)methanone To a solution of Example 1F (7.0 g, 14.8 mmol) in methanol (100 mL) was added hydroxylamine hydrochloride (6.1 g, 88.4 mmol), 50% hydroxylamine hydrate (6 mL, 97.8 mmol) and water (50 mL). The mixture was heated at reflux for 13 hours. After cooling to room temperature the reaction mixture was treated with 10N aqueous sodium hydroxide to adjust the pH to about 11. The reaction mixture was extracted with dichloromethane (3×200 mL). The combined organic fractions were washed with brine, dried with magnesium sulfate, filtered, and concentrated in vacuo. A solution of hydrochloric acid (4N, 30 mL) in ethyl acetate (30 mL) was added to the residue and the solution was stirred at room temperature for 1 hour. The solvent was removed in vacuo to afford Example 1H as a hydrochloride salt.

Example 1I (R)-3-methoxydihydro-2H-pyran-4(3H)-one

Step 1
To a mixture of tetrahydro-4H-pyran-4-one (38.9 g, 0.38 mol) and Et$_3$N (76.8 g, 0.76 mol) in dichloromethane (800 mL) was added tert-butyl dimethyl silyl trifluoromethane sulfonate (105.5 g, 0.399 mol) dropwise over 3 hours. After addition, the reaction was allowed to warm to room temperature and stirred overnight. Water was added and the resulting solution was extracted with dichloromethane (2×500 mL). The combined organic phase was washed with water (2×500 mL) and brine (2×200 mL), dried over Na$_2$SO$_4$, filtered, and concentrated to an oil (78 g, 85%).
Step 2
To a solution of (DHQD)$_2$PHAL (hydroquinidein 1,4-phthalazinediyl diether) (3.06 g, 3.93 mol), K$_2$OsO$_4$ (723 mg, 1.96 mol) and N-methylmorpholine-N-oxide (58.4 g, 0.432 mol) in acetone/H$_2$O (700 mL, 10/1) at 0° C. was added slowly a solution of the product from step 1 (84 g, 0.393 mol) in acetone (100 mL) for 5 hours. The resulting solution was stirred at 10-20° C. overnight. A freshly prepared solution of Na$_2$S$_2$O$_5$ (44.8 g, 0.236 mol) in water (315 mL) was added followed by acetic acid (67.3 mL). After stirring for 16 hours at room temperature, the solid was filtered, washed with isopropanol (400 mL), and dried to a white solid (60 g, 73%).
Step 3
To a solution of the product from step 2 (60 g, 0.294 mol) and HC(OCH$_3$)$_3$ (69.3 g, 0.647 mol) in MeOH (500 mL) at 50° C. was added HCl/MeOH (68 mL, 5-6 N) slowly over 30 minutes. Then the slurry was cooled to 5° C. and aqueous NaOH (50% in water, 100 mL) was added over 1 hour. The solid was filtered and the filtrate was concentrated. The resulting solution was washed with toluene for several times and then concentrated to an oil (38 g, yield: 88%).
Step 4
To a solution of the product from step 3 (9.5 g, 64.68 mol) in tetrahydrofuran (300 mL) was added sodium tert-butoxide (9.3 g, 97.02 mmol) at ice bath. Then dimethyl sulfate (13.4 g, 106 mmol) was added over 20 minutes, maintaining an internal temp below 36° C. After addition, the reaction mixture was stirred for 4 hours at room temperature. Water (200 mL) was added followed by addition of 2N HCl (100 mL). The apparent pH was below 1. After 16 hours of reaction, NaHCO$_3$ (20 g) was added and the mixture was extracted with ethyl acetate (4×300 mL), dried over Na$_2$SO$_4$, filtered, and concentrated to an oil (6 g, yield: 71%).

Example 1J 1,5-anhydro-2,3-dideoxy-4-O-methyl-3-{[(2R,3aR, 6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-threo-pentitol To a cooled (ice bath) solution of Example 1H (0.2 g, 0.506 mmol) in isopropyl acetate (10 mL) was added tributylamine (0.2 g, 1.08 mmol), followed by the addition of isopropanol (0.2 mL, mmol) and sodium triacetoxyborohydride (0.3 g, 1.4 mmol). After 1 hour, a solution of Example 11 (0.2 g, 1.5 mmol) in isopropyl acetate (2 mL) was added to the reaction mixture at about 1° C. Then the reaction mixture was stirred at room temperature for 15 hours. The mixture was partitioned between saturated aqueous sodium bicarbonate (15 mL) and water (20 mL) sequentially. The aqueous layer was extracted with ethyl acetate (three times). The combine organic fractions were washed with saturated aqueous sodium bicarbonate, dried over sodium sulfate, filtered, and concentrated. The residue was purified by silica gel chromatography (dichloromethane:methanol=20:1) to provide a mixture of two diastereoisomers, which was then further purified by chiral SFC (Supercritical fluid chromatography) with a preparative ChiralCel AD column (250 mm*30 mm, 5 μm) eluting with mobile phase:A, supercritical CO$_2$; B, ethanol (0.05% diethylamine), A:B=75:25 with a flow rate of 80 mL/min to yield title compound (peak 2, retention time: 18.42 minutes) as white solid, as well as Example 2. $^1$H NMR (400 MHz, CDCl$_3$) δ (ppm): 8.08 (s, 1H), 6.90-7.10 (m, 2H), 4.80-5.26 (m, 2H), 4.20 (d, J=13.2 Hz, 1H), 4.05 (m, 2H), 3.65-3.90 (m, 4H), 3.29-3.47 (m, 8H), 2.50-2.70 (m, 1H), 1.90-2.40 (m, 6H), 1.65-1.85 (m, 6H), 1.30-1.60 (m, 2H); MS (ESI) m/z 509 (M+H)$^+$.

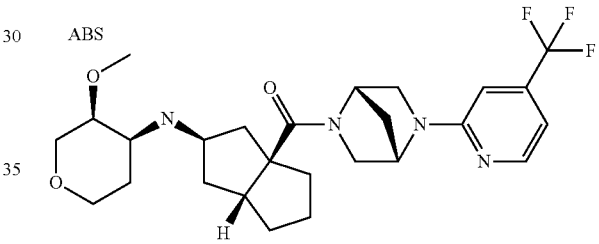

Example 2

1,5-anhydro-2,3-dideoxy-4-O-methyl-3-{[(2R,3aR, 6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol Method A:

The title compound was obtained from SFC purification of the diastereomeric mixture of Example 1J (first peak, retention time: 16.27 minutes). $^1$H NMR (400 MHz, CD$_3$OD) δ (ppm): 8.23 (d, J=5.6 Hz, 1H), 6.76-6.81 (m, 2H), 4.95 (m, 2H), 4.10-4.23 (m, 1H), 3.87-4.00 (m, 1H), 3.20-3.76 (m, 12H), 2.60-2.82 (m, 1H), 1.45-2.25 (m, 12H), 1.32 (m, 2H); MS (ESI) m/z 509 (M+H)$^+$.

The succinic acid salt of the title compound was prepared by stirring the free base (1.0 mg, 1.97 mmol) in methanol (40 mL) with succinic acid (230 mg, 1.97 mmol) at 80° C. for 4 hours, followed by concentration under reduced pressure. $^1$H NMR (400 MHz, CD$_3$OD) δ (ppm) 8.23-8.24 (d, J=5.2 Hz, 1H), 6.80 (d, J=5.2 Hz, 1H), 6.77 (d, J=12.4 Hz, 1H), 5.03 (m, 2H), 4.22 (t, J=14.4 Hz, 1H), 3.95 (m, 1H), 3.30-3.85 (m, 12H), 2.50 (s, 4H), 2.20-2.45 (m, 1H), 1.60-2.15 (m, 13H), 1.40 (m, 1H); MS (ESI) m/z 509 (M+H)$^+$.

Method B:

Example 2B1

(2R,3aR,6aR)-methyl 2-aminooctahydropentalene-3a-carboxylate

To an aqueous solution of hydroxylamine hydrochloride (458 g, 6.59 mol) and sodium hydroxide (120 g, 3 mol) in water (350 mL) was added a solution of Example 1D (119 g, 0.454 mol) in methanol (2 L) and the mixture was stirred at 65° C. for 8 hours. The mixture was cooled to room temperature, sufficient water was added and the methanol was removed under reduced pressure. The resulting slurry was adjusted to pH 10 with an aqueous sodium hydroxide solution (2.5 N) and the reaction mixture was extracted with dichloromethane. The combined organic fractions were washed with brine, dried over sodium sulfate, filtered, and concentrated to afford the title compound, which was used in the next step without further purification.

Example 2B2

(2R,3aR,6aR)-methyl 2-((3S)-3-methoxytetrahydro-2H-pyran-4-ylamino)octahydropentalene-3a-carboxylate To a solution of Example 2B1 (50 g, 0.168 mol) in dichloromethane (100 mL) was added Example 1I (24 g, 0.185 mol) at room temperature over 1 hour. The solution was cooled to 0° C. Sodium triacetoxyborohydride (78 g, 0.37 mol) was added and the mixture was stirred at 0° C. for 2 hours. The reaction mixture was diluted with water. The resulting slurry was adjusted to pH=10 with saturated sodium bicarbonate solution and the crude product was extracted with ethyl acetate. The combined organic fractions were washed with brine, dried with sodium sulfate, filtered, and concentrated to afford the title compound, which was used in the next step without further purification.

Example 2B3

(2R,3aR,6aR)-2-((3S)-3-methoxytetrahydro-2H-pyran-4-ylamino)octahydropentalene-3a-carboxylic acid To a solution of Example 2B2 (30 g, 0.101 mol) in methanol (120 mL) was added a aqueous solution of sodium hydroxide (81 mL, 2.5 N) and the reaction mixture was stirred at room temperature for 4 hours. Methanol was removed under reduced pressure. The resulting slurry was adjusted to pH 5 with a citric acid solution (1 N aqueous) and the reaction mixture was extracted with ethyl acetate. The combined organic fractions were washed with brine, dried over sodium sulfate, filtered, and concentrated to afford the title compound.

Example 2B4

(2R,3aR,6aR)-benzyl 2-((3S,4S)-3-methoxytetrahydro-2H-pyran-4-ylamino)octahydropentalene-3a-carboxylate To a solution of Example 2B3 (25 g, 88.3 mmol) in dichloromethane (100 mL) was added benzyl alcohol (18.1 g, 168 mmol), 4-dimethylaminopyridine (3.3 g, 27 mmol), triethylamine (12.4 g, 123 mmol) and 1-ethyl-3-[3-(dimethylamino)propyl]-carbodiimide hydrochloride (24 g, 123 mmol). The reaction mixture was stirred at room temperature for 16 hours. The solution was concentrated and the residue was partitioned between MTBE and water. The organic layer was collected and washed with brine, dried over sodium sulfate, filtered, and concentrated. The residue was purified by column chromatography ($SiO_2$, petroleum ether:ethyl acetate=4:1) then further purified by SFC(SFC condition: column: IC 250 mm*30 mm, 5 μm; mobile phase: A, supercritical $CO_2$; B, ethanol (0.05% diethylamine), A:B=75:25 with a flow rate of 80 mL/min) to give the title compound (peak 1, retention time: 5.39 minutes).

Example 2B5

(2R,3aR,6aR)-benzyl 2-(2,2,2-trifluoro-N-((3S,4S)-3-methoxytetrahydro-2H-pyran-4-yl)acetamido)octahydropentalene-3a-carboxylate To a solution of Example 2B4 (8.1 g, 21.7 mmol) in dichloromethane (50 mL) at 0° C. was added diisopropylethylamine (7 g, 54.3 mmol) and trifluoroacetic anhydride (10 g, 47.8 mmol). The mixture was then stirred at room temperature for 2 hours. The reaction mixture was diluted with water and extracted with dichloromethane (2×50 mL). The combined organic fractions were washed with brine, dried over sodium sulfate, filtered, and concentrated to afford the title compound.

Example 2B6

(2R,3aR,6aR)-2-(2,2,2-trifluoro-N-((3S,4S)-3-methoxytetrahydro-2H-pyran-4-yl)acetamido)octahydropentalene-3a-carboxylic acid To a suspension of Pd/C (1.2 g, 50%, mmol) in methanol (5 mL) was added a solution of Example 2B5 (10.8 g, 23.2 mmol) in methanol (30 mL). The mixture was stirred under $H_2$ atmosphere (50 psi) at room temperature for 2 hours. The solid was filtered and the filtrate was concentrated to give the title compound.

Example 2B7

2,2,2-trifluoro-N-((3S,4S)-3-methoxytetrahydro-2H-pyran-4-yl)-N-((2R,3aR,6aR)-3a-((1S,4S)-5-(4-(trifluoromethyl)pyridin-2-yl)-2,5-diazabicyclo[2.2.1]heptane-2-carbonyl)octahydropentalen-2-yl)acetamide To a solution of Example 2B6 (8.8 g, 23.2 mmol) in dichloromethane (50 mL) at 0° C. was added oxalyl chloride (12.2 g, 95.8 mmol) and 2 drops of N,N-dimethylformamide. After 30 minutes, the solution was concentrated to dryness. The residue was dissolved in dichloromethane (50 mL). To this solution at 0° C. was added diisopropylethylamine (18 g, 139.2 mmol) and Example 1F (8.2 g, 25.5 mmol). Then the mixture was stirred at room temperature for 3 hours. The mixture was diluted with water and extracted with ethyl acetate (2×100 mL). The combined organic fractions were washed with brine, dried with sodium sulfate, and concentrated. The residue was purified by column chromatography ($SiO_2$, petroleum ether:ethyl acetate=3:1) to afford the title compound.

A solution of Example 2B7 (10.3 g, 17.1 mmol) and sodium borohydride (2.6 g, 68 mmol) in dichloromethane/ethanol (5 mL/30 mL) was stirred at room temperature for 2 hours. Water was added and the resulting solution was adjusted to pH 10 with saturated aqueous sodium carbonate. The reaction mixture was extracted with ethyl acetate. The combined organic fractions were washed with brine, dried over sodium sulfate, filtered, and concentrated to provide 1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol.

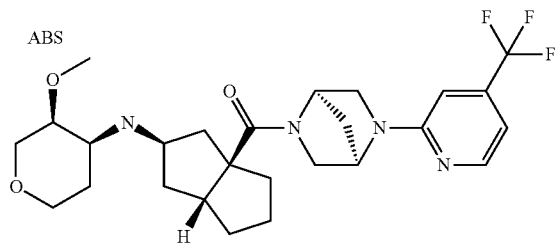 [SMILES: "ABS" ; CO[C@@H]1COCC[C@@H]1N[C@@H]1C[C@H]2CCC[C@@]2(C(=O)N2C[C@H]3C[C@@H]2CN3c2cc(C(F)(F)F)ccn2)C1]

Example 3

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-erythro-pentitol

Example 3A (1R,4R)-2-(4-(trifluoromethyl)pyridin-2-yl)-2,5-diazabicyclo[2.2.1]heptane The title compound was prepared and purified using procedures analogous to those described in Example 1F, substituting (1R,4R)-tert-butyl 2,5-diazabicyclo[2.2.1]heptane-2-carboxylate for (1S,4S)-tert-butyl 2,5-diazabicyclo[2.2.1]heptane-2-carboxylate to obtain the title compound.

Example 3B 1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-erythro-pentitol The title compound was prepared and purified using procedures analogous to that described in Examples 1G, 1H, and 1J (SFC condition: AD column (250 mm*30 mm, 5 μm) eluting with mobile phase:A, Supercritical $CO_2$; B, isopropyl alcohol (0.05% diethylamine), A:B=65:35 with a flow rate of 60 mL/min) to afford Example 3 (peak 1, retention time: 3.88 minutes, 23 mg), Example 4 (peak 2, retention time: 5.54 minutes), substituting Example 3A for Example 1F. $^1$H NMR (400 MHz, CDCl$_3$) δ (ppm): 8.24 (s, 1H), 6.75 (m, 1H), 6.50 (m, 1H), 4.75-5.05 (m, 2H), 4.14 (m, 1H), 3.95 (m, 1H), 3.30-3.70 (m, 12H), 2.92 (m, 1H), 1.45-2.10 (m, 13H), 1.28 (m, 2H); MS (ESI) m/z 509 (M+H)$^+$.

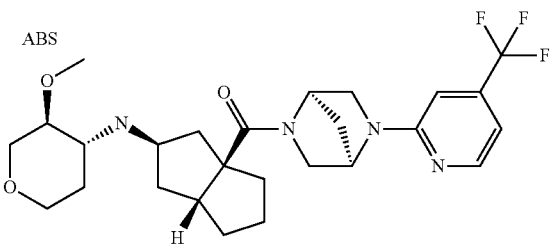 [SMILES: "ABS" ; CO[C@@H]1COCC[C@H]1N[C@@H]1C[C@H]2CCC[C@@]2(C(=O)N2C[C@H]3C[C@@H]2CN3c2cc(C(F)(F)F)ccn2)C1]

Example 4

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-threo-pentitol The title compound was isolated as the second peak from the SFC purification of Example 3B. $^1$H NMR (400 MHz, CDCl$_3$) δ (ppm): 8.17 (s, 1H), 6.39-6.70 (m, 2H), 4.68-4.94 (m, 2H), 4.05 (m, 1H), 3.90 (m, 1H), 3.26-3.65 (m, 12H), 2.86 (m, 1H), 1.45-2.05 (m, 13H), 1.23 (m, 2H); MS (ESI) m/z 509 (M+H)$^+$.

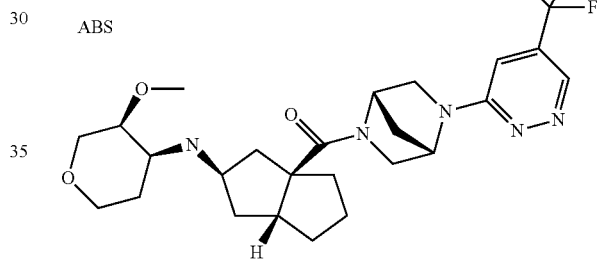

Example 5

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-erythro-pentitol

Example 5A (1S,4S)-2-(5-(trifluoromethyl)pyridazin-3-yl)-2,5-diazabicyclo[2.2.1]heptane The title compound was prepared and purified using procedures analogous to those described in Example 1F, substituting 3-chloro-5-(trifluoromethyl)pyridazine for 2-chloro-4-trifluoromethylpyridine.

Example 5B 1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-erythro-pentitol The title compound (retention time: 4.31 minutes) was prepared and purified using procedures similar to that described in Examples 1G, 1H, and 1J, substituting Example 5A for Example 1F. $^1$H NMR (400 MHz, CDCl$_3$) δ (ppm): 8.69 (s, 1H), 6.68 (m, 2H), 4.75-5.26 (m, 2H), 4.05 (m, 1H), 3.86 (m, 1H), 3.52-3.75 (m, 3H), 3.10-3.45 (m, 9H), 2.57-2.75 (m, 1H), 1.38-2.10 (m, 12H), 1.22 (m, 2H); MS (ESI) m/z 510 (M+H)$^+$.

dient:18-48 with a flow rate of 25 mL/min) to afford Example 7 (retention time: 12 minutes) as the trifluoroacetic acid salt. $^1$H NMR (400 MHz, CD$_3$OD) δ (ppm): 8.23 (d, J=5.6 Hz, 1H), 6.96-7.14 (m, 2H), 5.07-5.09 (m, 2H), 4.18-4.38 (m, 1H), 4.05 (m, 1H), 3.30-3.90 (m, 1H), 2.60-2.90 (m, 4H), 1.60-2.35 (m, 13H), 1.45 (m, 1H); MS (ESI) m/z 523 (M+H)$^+$.

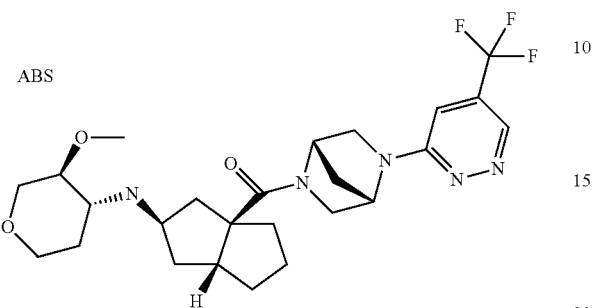

Example 6

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino})-D-threo-pentitol The title compound (retention time: 6.53 minutes) was isolated as the other product from the preparation of Example 5B. $^1$H NMR (400 MHz, CDCl$_3$) δ (ppm): 8.72 (s, 1H), 6.69 (s, 2H), 4.75-5.26 (m, 2H), 4.05 (m, 1H), 3.86 (m, 1H), 3.52-3.75 (m, 3H), 3.10-3.45 (m, 9H), 2.57-2.75 (m, 1H), 1.38-2.10 (m, 12H), 1.22 (m, 2H); MS (ESI) m/z 510 (M+H)$^+$.

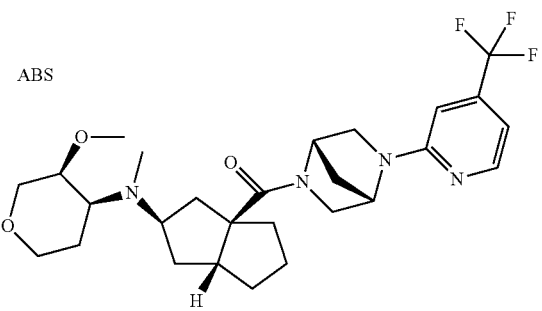 [SMILES: "ABS" ; CO[C@@H]1COCC[C@@H]1N(C)[C@@H]1C[C@H]2CCC[C@@]2(C(=O)N2C[C@@H]3C[C@H]2CN3c2cc(C(F)(F)F)ccn2)C1]

Example 7

1,5-anhydro-2,3-dideoxy-4-O-methyl-3-{methyl [(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol To a solution of Example 2 (10 mg, 0.04 mmol) in dioxane (1 mL) was added an aqueous formic acid solution (0.6 mL, 20%, 0.2 mmol) and an aqueous formalin solution (37%, 0.6 mL, 0.2 mmol). The mixture was heated at 80° C. overnight under nitrogen. Concentration and purification by HPLC (condition: Column, Phenomentix 250 mm*21 mm*2 μm, mobile phase:A, acetonitrile; B, water (V/V, 0.1% TFA), Gra-

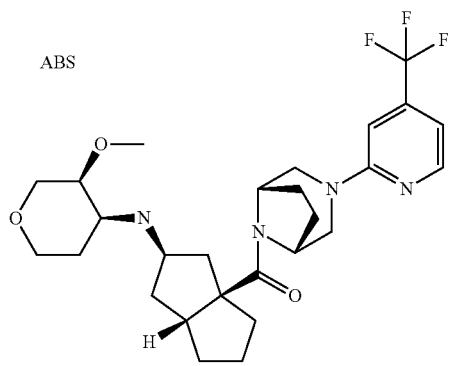 [SMILES: "ABS" ; CO[C@@H]1COCC[C@@H]1N[C@@H]1C[C@H]2CCC[C@@]2(C(=O)N2[C@@H]3CC[C@H]2CN(c2cc(C(F)(F)F)ccn2)C3)C1]

Example 8

1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-erythro-pentitol Example 8A (1S)-3-(4-(trifluoromethyl)pyridin-2-yl)-3,8-diazabicyclo[3.2.1]octane The title compound was prepared and purified using procedures analogous to those described in Example 1F, substituting 3-(4-trifluoromethyl-pyridin-2-yl)-3,8-diazabicyclo [3.2.1]octane-8-carboxylic acid tert-butyl ester for (1S,4S)-tert-butyl 2,5-diazabicyclo[2.2.1]heptane-2-carboxylate.

Example 8B (2-(2,5-dimethyl-1H-pyrrol-1-yl)octahydropentalen-3a-yl)((1S)-3-(4-(trifluoromethyl)pyridin-2-yl)-3,8-diazabicyclo[3.2.1]octan-8-yl)methanone To a solution of Example 1E (77 mg, 0.31 mmol) and Example 8A (80 mg, 0.31 mmol) in N,N-dimethylformamide (5 mL) was added 4-dimethylaminopyridine (76 mg, 0.62 mmol) and diisopropylethylamine (119 mg, 0.93 mmol). Bromo-tris-pyrrolidino phosphoniumhexafluorophosphate (288 mg, 0.62 mmol) was added and the mixture was stirred at room temperature overnight. The reaction mixture was quenched with water and extracted with ethyl acetate. The combined organic fractions were washed with brine, dried (MgSO$_4$), and concentrated. The residue was purified by column chromatography (20% to 100% ethyl acetate in petroleum ether) on silica gel to afford the title compound.

Example 8C (2-aminooctahydropentalen-3a-yl)((1S,5S)-3-(4-(trifluoromethyl)pyridin-2-yl)-3,8-diazabicyclo [3.2.1]octan-8-yl)methanone To a solution of hydroxylamine hydrochloride (103.5 mg, 1.49 mmol) in water (2 mL) was added sodium hydroxide (27 mg, 0.68 mmol). Example 8B (50 mg, 0.103 mmol) in methanol (10 mL) was added into the solution. The mixture was heated at reflux for 10 hours. The solvent was removed in vacuum and to the residue was added 2.5 M aqueous sodium hydroxide to adjust pH to 9-10. The reaction mixture was extracted with dichloromethane. The organic fractions were washed with brine, dried, (MgSO$_4$), and concentrated to afford the title compound.

Example 8D 1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-erythro-pentitol A solution of Example 8C (50 mg, 0.12 mmol) in isopropyl acetate (5 mL) was cooled with an ice bath. Tributyl amine (11 mg, 0.06 mmol) followed by addition of isopropyl alcohol (16.8 mg, 0.28 mmol) was added to the solution. Sodium triacetoxyborohydride (59 mg, 0.28 mmol) was added at 5° C. After stirring for 1 hour, a solution of Example 1I (23.4 mg, 0.18 mmol) in dichloromethane was added to the reaction mixture. Then the mixture was stirred at room temperature overnight. The reaction mixture was quenched with saturated sodium bicarbonate and extracted with ethyl acetate. The combined organic fractions were washed with brine, dried in vacuo and concentrated to provide a diastereomeric mixture. The diastereomeric mixture was separated by chiral SFC (Column: AD 250 mm*30 mm, 5 μm; Mobile phase:A, supercritical CO$_2$; B, isopropyl alcohol with 0.1% diethylamine, A:B=80:20 with a flow rate of 70 mL/min) to afford the title compound (peak 1, retention time: 7.11 minutes) and Example 41 (peak 2, retention time: 7.94 minutes); MS (ESI) m/z 523 (M+H)$^+$.

ABS

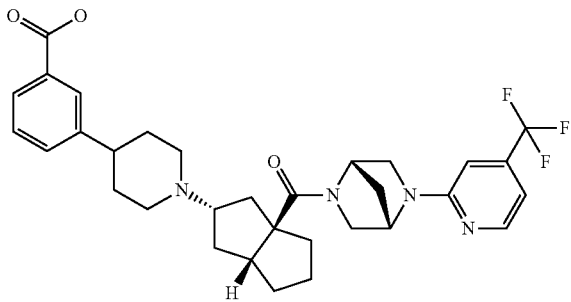

Example 9

3-{1-[(2S,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid Example 9A Ethyl 2-oxo-1-(2-oxopropyl)cyclopentanecarboxylate To a solution of ethyl 2-oxocyclopentanecarboxylate (150 g, 0.96 mol) in DMF (2000 mL) was added NaH (50 g, 0.88 mol) portion wise at 0° C., followed by 1-chloropropan-2-one (117.7 g, 1.24 mol). The mixture was stirred at room temperature for 24 hours under N$_2$. TLC (petroleum ether:ethyl acetate=5:1) indicated the reaction was completed. The mixture was filtered and the filtrate was concentrated in vacuum. The residue was poured into water at 0° C. The resulting aqueous layer was extracted with ethyl acetate (3×500 mL). Then the combined organic layers were dried over Na$_2$SO$_4$, filtered, and the solvent was evaporated in vacuum. The residue was purified by column chromatography (SiO$_2$, petroleum ether:ethyl acetate=80:1) to give Example 9A (125 g, 61.35%) as oil.

Example 9B

Ethyl 5-oxo-1,2,3,3a,4,5-hexahydropentalene-3a-carboxylate

To a refluxing mixture of NaH (28.27 g, 0.706 mol) in toluene (2000 mL) was added a solution of Example 9A in toluene (250 mL) dropwise over 2 hours. After the addition, the mixture was refluxed for 0.5 hour. TLC (petroleum ether: ethyl acetate=4:1) indicated that the reaction was complete. The mixture was cooled to room temperature and poured into aqueous HCl (1 N, 1500 mL), extracted with ethyl acetate (3×500 mL). The combined organic layers was dried over Na$_2$SO$_4$, filtered, concentrated, and the residue was purified by chromatography (SiO$_2$, 0% to 10% ethyl acetate in petroleum ether) to give Example 9B (27.75 g, 48.5%) as oil.

Example 9C

Ethyl 2-oxooctahydropentalene-3a-carboxylate

A mixture of Example 9B (50 g, 0.257 mol), Pd/C (8 g) in EtOH (500 mL) was stirred under hydrogen at 40 psi for 4 hours at room temperature. TLC (petroleum ether:ethyl acetate=4:1) indicated the reaction was complete. The mixture was filtered and concentrated in vacuum. The residue was purified by column chromatography (SiO$_2$, 0% to 10% ethyl acetate in petroleum ether) to give Example 9C (30 g, 58.8%) as light yellow oil.

Example 9D 2-oxooctahydropentalene-3a-carboxylic acid

A solution of Example 9C (10 g, 0.051 mol) in HCl (12 N, 150 mL) was heated at reflux for 4 hours. TLC (petroleum ether ethyl acetate=5:1) indicated that the reaction was complete. The mixture was cooled to room temperature and extracted with dichloromethane (3×30 mL). The organic layer was dried over Na$_2$SO$_4$, filtered, and concentrated in vacuum to give Example 9D (7.05 g, 80.4%) as grey oil, which was used in the next step directly.

Example 9E (3aR,6aR)-3a-((1S,4S)-5-(4-(trifluoromethyl)pyridin-2-yl)-2,5-diazabicyclo[2.2.1]heptane-2-carbonyl)hexahydropentalen-2(1H)-one A mixture of Example 9D (0.8 g, 4.75 mmol), Example 1F (1.33 g, 4.75 mmol), 1-ethyl-3-(3-dimethylaminopropyl)carbodiimide (1.37 g, 7.13 mmol), hydroxybenzotriazole (0.647 g, 4.75 mmol), triethylamine (2.74 mL, 19.03 mmol) in dichloromethane (50 mL) was stirred for 12 hours at room temperature under a nitrogen atmosphere. The mixture was washed with water (50 mL) and extracted with dichloromethane (50 mL×3). The dichloromethane was dried with sodium sulfate and concentrated. Purification by chromatography on silica (50% ethyl acetate in petroleum ether) and the resulting isomers were separated by SFC (SFC condition: Column: AD-250 mm*30 mm, 5 μm; Mobile phase:A, supercritical CO$_2$; B, ethanol, A:B=60:40 with a flow rate of 45 mL/min), peak 2, retention time: 14.17 minutes) to give the title compound.

Example 9F ethyl 3-(1-((2S,3aR,6aR)-3a-((S,4S)-5-(4-(trifluoromethyl)pyridin-2-yl)-2,5-diazabicyclo[2.2.1]heptane-2-carbonyl)octahydropentalen-2-yl)piperidin-4-yl)benzoate A mixture of Example 9E (200 mg, 0.5 mmol), ethyl 3-(piperidin-4-yl)benzoate (125 mg, 0.56 mmol) in dichloroethane (20 mL) was added titanium(IV) isopropoxide (0.6 ml, 2.03 mmol) at room temperature. The mixture was stirred at room temperature for 12 hours. Sodium borohydride (96.7 mg, 2.54 mmol) and methanol (1 mL) were added to the reaction mixture and stirred for another 2 hours. LC-MS indicated that the reaction was complete. Aqueous Sodium bicarbonate (20 mL) was added to the reaction mixture. The reaction mixture was extracted with dichloromethane (3×30 mL). The organic fractions were dried with sodium sulfate, filtered, and concentrated. The residue was purified by chromatography (eluent: 20 to 80% ethylacetate in petroleum ether) on silica to give a mixture of the title compound and isopropyl benzoate.

Example 9G

3-{1-[(2S,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid The mixture from Example 9F (280 mg, 0.45 mmol), sodium methoxide (49.5 mg, 0.91 mmol) in methanol (10 mL) was refluxed for 12 hours. The mixture was acidified with 0.1 N aqueous hydrochloric acid to a pH around 5. The reaction mixture was partitioned with the addition of dichloromethane. The dichloromethane was collected and the aqueous solution was washed with dichloromethane (three times). The dichloromethane fractions were combined, dried and concentrated. The crude product was purified by preparative HPLC (Column: Phenomenex 150*30 mm; mobile phase: from 30% acetonitrile in H$_2$O (0.01% TFA) to 70% acetonitrile in H$_2$O (0.01% TFA) followed by chiral SFC purification (SFC condition: Column: AD-5 μm; Mobile phase:A, supercritical CO$_2$; B, ethanol with 0.05% diethylamine, A:B=70: 30 with a flow rate of 50 mL/min)) to give the title compound (peak 1 retention time: 5.58 minutes) and Example 10. $^1$H NMR (400 MHz, CD$_3$OD) δ (ppm): 8.24 (d, J=5.2 Hz, 1H), 7.80 (m, 2H), 7.28 (m, 2H), 6.78 (m, 2H), 5.10 (m, 2H) 3.30-3.79 (m, 6H), 3.20 (m, 1H), 2.70-2.96 (m, 3H), 2.25-2.65 (m, 1H), 1.50-2.15 (m, 15H), 1.38 (m, 1H); MS (ESI$^+$) m/z 583 (M+H)$^+$.

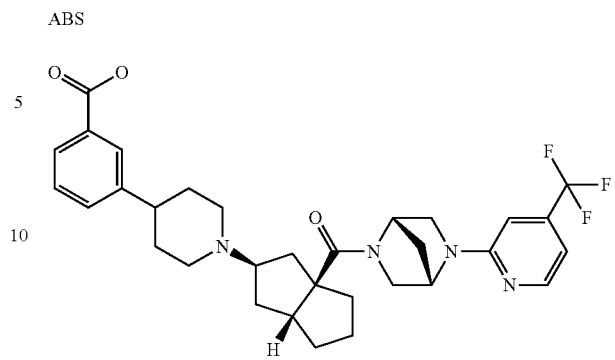

Example 10

3-{1-[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid The title compound was obtained from the chiral SFC separation of the isomers obtained from Example 9G (peak 2, retention time: 7.61 minutes). $^1$H NMR (400 MHz, CD$_3$OD) δ (ppm): 8.24 (s 1H), 7.75-7.90 (m, 2H), 7.30 (m, 2H), 6.78 (m, 2H), 4.95 (m, 2H) 3.70 (s 1H), 3.62 (m, 2H), 3.45 (m, 2H), 3.10-3.25 (m, 1H), 2.60-2.96 (m, 4H), 2.30-2.50 (m, 1H), 1.50-2.15 (m, 15H), 1.40 (m, 1H). MS (ESI) m/z 583 (M+H)$^+$.

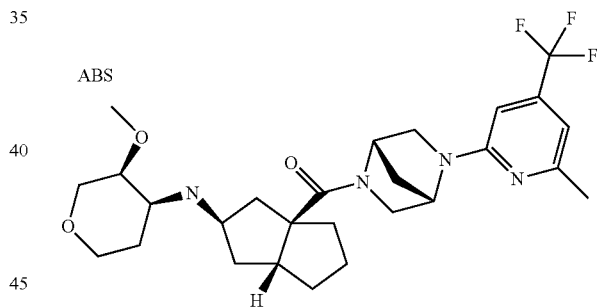

Example 11

1,5-anhydro-2,3-dideoxy-4-O-methyl-3-{[(2R,3aR, 6aR)-3a-({(1S,4S)-5-[6-methyl-4-(trifluoromethyl)pyridin-2-yl]-2,5-diazabicyclo[2.2.1]hept-2-yl}carbonyl)octahydropentalen-2-yl]amino}-D-erythro-pentitol Example 11A 1,5-anhydro-3-{[(2R,3aR,6aR)-3a-{[(1S,4S)-5-(tert-butoxycarbonyl)-2,5-diazabicyclo[2.2.1]hept-2-yl]carbonyl}octahydropentalen-2-yl](trifluoroacetyl)amino}-2,3-dideoxy-4-O-methyl-D-erythro-pentitol To a solution of Example 2B6 (4.8 g, 12.8 mmol) in dichloromethane (35 mL) at 0° C. was added oxalyl chloride (6.7 g, 52.9 mmol) and 2 drops of N,N-dimethylformamide. After 30 minutes the solution was concentrated to dryness. The intermediate was dissolved in dichloromethane (50 mL). To this solution at 0° C. was added diisopropylethylamine (9.9 g, 76.8 mmol) and (1S,4S)-tert-butyl 2,5-diazabicyclo[2.2.1]heptane-2-carboxylate (2.8 g, 14.1 mmol). The reaction mixture was stirred at room temperature for 3 hours. The mixture was diluted with water and extracted with ethyl acetate (2×100 mL). The combined organic fractions were washed with brine, dried with sodium sulfate, filtered, and concentrated. Purification by column chromatography (SiO₂, petroleum ether, ethyl acetate=3:1) to give the title compound.

Example 11A-1

1,5-anhydro-3-{[(2R,3aR,6aR)-3a-{[(1S,4S)-5-carboxy-2,5-diazabicyclo[2.2.1]hept-2-yl]carbonyl}octahydropentalen-2-yl]amino}-2,3-dideoxy-4-O-methyl-D-erythro-pentitol A solution of Example 11A (5.5 g, 9.8 mmol) and NaBH₄ (1.1 g, 29.4 mmol) in dichloromethane/ethanol (20 mL/20 mL) was stirred at room temperature for 2 hours. Water was added and the resulting solution was adjusted to pH=10 with saturated Na₂CO₃ solution and extracted with ethyl acetate. The combined organic layer was washed with brine, dried over Na₂SO₄, filtered, and concentrated to result in the title compound (4.3 g, 95%).

Example 11B 1,5-anhydro-2,3-dideoxy-3-({(2R,3aR,6aR)-3a-[(1S,4S)-2,5-diazabicyclo[2.2.1]hept-2-ylcarbonyl]octahydropentalen-2-yl}amino)-4-O-methyl-D-erythro-pentitol A solution of Example 11A-1 (5.5 g, 12.8 mmol) in methanol (5 mL) and a solution of hydrochloric acid in methanol (50 mL, 4 M) was stirred at room temperature for 2 hours. The solution was concentrated to dryness to give the title compound as the hydrochloric acid salt.

Example 11C 1,5-anhydro-2,3-dideoxy-4-O-methyl-3-{[(2R,3aR,6aR)-3a-({(1S,4S)-5-[6-methyl-4-(trifluoromethyl)pyridin-2-yl]-2,5-diazabicyclo[2.2.1]hept-2-yl}carbonyl)octahydropentalen-2-yl]amino}-D-erythro-pentitol A mixture of Example 11B (90 mg, 0.177 mmol), 2-chloro-6-methyl-4-(trifluoromethyl)pyridine, (108 mg, 0.443 mmol) and diisopropylethylamine (92 mg, 0.707 mmol) in dimethylsulfoxide (1 mL) was stirred at 90° C. for 12 hours. The mixture was purified by preparative HPLC (Column: Phenomenex Synergi C18 150*30 mm*4 μm; Mobile phase: from 17% acetonitrile in water (0.1% TFA) to 37% acetonitrile in water (0.1% TFA); Wavelength: 220 nm) to give the title compound as the trifluoroacetic acid salt. MS (ESI) m/z 523 (M+H)⁺.

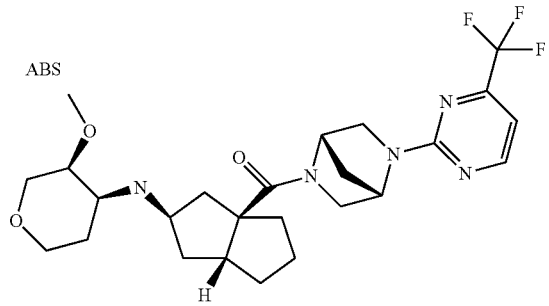 [SMILES: "ABS" ; CO[C@@H]1COCC[C@@H]1N[C@@H]1C[C@H]2CCC[C@@]2(C(=O)N2C[C@@H]3C[C@H]2CN3c2nccc(C(F)(F)F)n2)C1]

Example 12

1,5-anhydro-2,3-dideoxy-4-O-methyl-3-{[(2R,3aR,6aR)-3a-({(1S,4S)-5-[4-(trifluoromethyl)pyrimidin-2-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 1° C., substituting 2-chloro-4-(trifluoromethyl)pyrimidine for 2-chloro-6-methyl-4-(trifluoromethyl)pyridine. ¹H NMR (400 MHz, CD₃OD) δ (ppm): 8.57-8.58 (d, J=4.8 Hz, 1H), 6.93-6.94 (d, J=4.8 Hz, 1H), 5.12-5.19 (m, 1H), 4.91-4.97 (m, 2H), 4.25 (m, 1H), 3.30-4.01 (m, 12H), 2.23-2.55 (m, 1H), 1.60-2.15 (m, 13H), 1.39 (m, 1H); MS (ESI) m/z 510 (M+H)⁺.

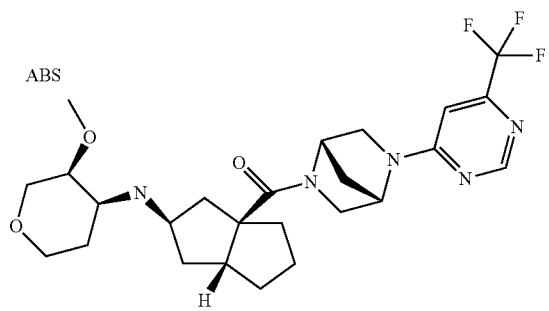 [SMILES: "ABS" ; CO[C@@H]1COCC[C@@H]1N[C@@H]1C[C@H]2CCC[C@@]2(C(=O)N2C[C@@H]3C[C@H]2CN3c2cc(C(F)(F)F)ncn2)C1]

Example 13

1,5-anhydro-2,3-dideoxy-4-O-methyl-3-{[(2R,3aR,6aR)-3a-({(1S,4S)-5-[6-(trifluoromethyl)pyrimidin-4-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 4-chloro-6-(trifluoromethyl)pyrimidine for 2-chloro-6-methyl-4-(trifluoromethyl)pyridine. ¹H NMR (400 MHz, CD₃OD) δ (ppm): 8.46 (s, 1H), 7.08 (s, 0.5H), 6.70 (s, 0.5H), 4.85-5.26 (m, 3H), 4.15 (m, 1H), 3.20-3.92 (m, 12H), 2.15-2.45 (m, 1H), 1.49-2.05 (m, 13H), 1.30 (m, 1H); MS (ESI) m/z 510 (M+H)⁺.

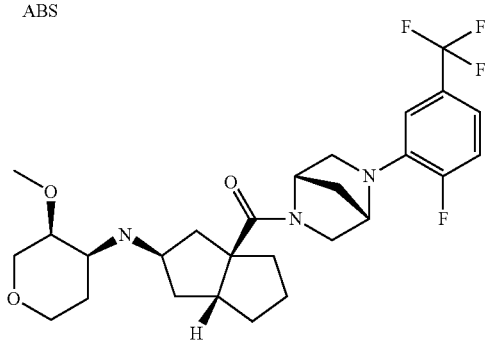 [SMILES: "ABS" ; CO[C@@H]1COCC[C@@H]1N[C@@H]1C[C@H]2CCC[C@@]2(C(=O)N2C[C@@H]3C[C@H]2CN3c2cc(C(F)(F)F)ccc2F)C1]

Example 14

1,5-anhydro-2,3-dideoxy-3-{[(2R,3aR,6aR)-3a-({(1S,4S)-5-[2-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol To a solution of Example 11B (70 mg, 0.193 mmol), 2-bromo-1-fluoro-4-(trifluoromethyl)benzene (117 mg, 0.483 mmol) in toluene (1 mL) was added 2-dicyclohexylphosphino-2',4',6'-triisopropylbiphenyl (9 mg, 0.02 mmol), Pd$_2$(dba)$_3$ (18 mg, 0.02 mmol) and sodium t-butoxide (26 mg, 0.27 mmol) was then stirred at 120° C. for 12 hours. The reaction was cooled and water was added. The reaction mixture was extracted with ethyl acetate. The organic fractions were concentrated and the residue was purified by preparative HPLC (Column: Phenomenex Synergi C18 150*30 mm*4 μm; Mobile phase: from 25% acetonitrile in water (0.225% TFA) to 45% acetonitrile in water (0.1% TFA)) to give the title compound as a trifluoroacetic acid salt. $^1$H NMR (400 MHz, CD$_3$OD) δ (ppm): 7.20 (m, 1H), 7.01 (m, 2H), 4.55-4.85 (m, 3H), 4.29 (m, 1H), 3.47-4.04 (m, 12H), 1.60-2.50 (m, 13H), 1.42 (m, 2H); MS (ESI) m/z 526 (M+H)$^+$.

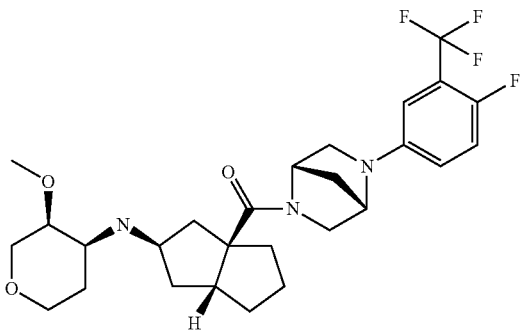

Example 15

1,5-anhydro-2,3-dideoxy-3-{[(2R,3aR,6aR)-3a-({(1S,4S)-5-[4-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol The trifluoroacetic acid salt of the title compound was prepared and purified using procedure similar to that described in Example 14, substituting 4-bromo-1-fluoro-2-(trifluoromethyl)benzene for 2-bromo-1-fluoro-4-(trifluoromethyl)benzene. $^1$H NMR (400 MHz, CD$_3$OD) δ (ppm): 7.12-7.17 (t, J=14.0 Hz, 1H), 6.79-6.88 (m, 2H), 4.52-4.75 (m, 3H), 4.25 (t, J=14.4 Hz, 1H), 3.90-4.00 (m, 1H), 3.05-3.82 (m, 11H), 1.53-2.20 (m, 13H), 1.35 (m, 2H); MS (ESI) m/z 526 (M+H)$^+$.

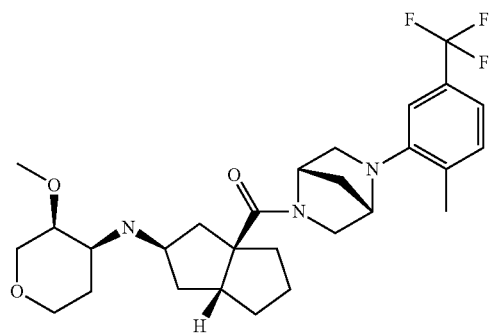

Example 16

1,5-anhydro-2,3-dideoxy-4-O-methyl-3-{[(2R,3aR,6aR)-3a-({(1S,4S)-5-[2-methyl-5-(trifluoromethyl)phenyl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 14, substituting 2-bromo-1-methyl-4-(trifluoromethyl)benzene for 2-bromo-1-fluoro-4-(trifluoromethyl)benzene. $^1$H NMR (400 MHz, CD$_3$OD) δ (ppm): 7.26 (d, J=8.0 Hz, 1H), 7.07 (s, 2H), 4.20-4.45 (m, 2H), 3.95 (m, 1H), 3.24-3.85 (m, 13H), 2.35 (s, 3H), 1.65-2.45 (m, 13H), 1.42 (m, 2H); MS (ESI) m/z 522 (M+H)$^+$.

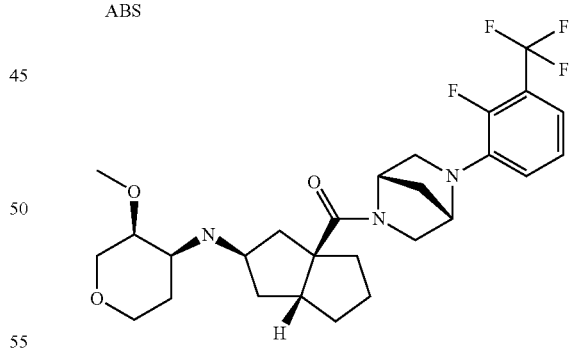

Example 17

1,5-anhydro-2,3-dideoxy-3-{[(2R,3aR,6aR)-3a-({(1S,4S)-5-[2-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol The trifluoroacetic acid salt of the title compound was prepared and purified using procedure similar to that described in Example 14, substituting 1-bromo-2-fluoro-3-

(trifluoromethyl)benzene for 2-bromo-1-fluoro-4-(trifluoromethyl)benzene. MS (ESI) m/z 526 (M+H)+.

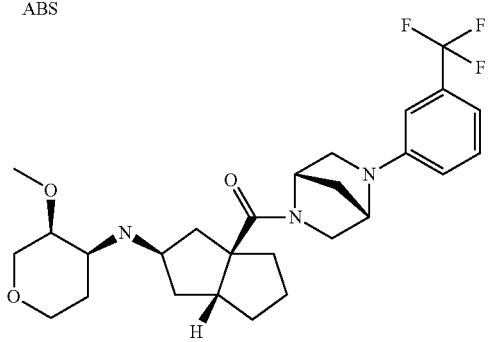 [SMILES: "ABS" ; CO[C@@H]1COCC[C@@H]1N[C@@H]1C[C@H]2CCC[C@@]2(C(=O)N2C[C@@H]3C[C@H]2CN3c2cccc(C(F)(F)F)c2)C1]

Example 18

1,5-anhydro-2,3-dideoxy-4-O-methyl-3-{[(2R,3aR, 6aR)-3a-({(1S,4S)-5-[3-(trifluoromethyl)phenyl]-2, 5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 14, substituting 1-bromo-3-(trifluoromethyl)benzene for 2-bromo-1-fluoro-4-(trifluoromethyl) benzene. ¹H NMR (400 MHz, CD₃OD) δ (ppm): 7.35 (m, 1H), 6.80-6.95 (m, 3H), 4.88-4.93 (m, 1H), 4.65 (m, 2H), 4.12 (m, 1H), 3.89 (m, 1H), 3.65-3.75 (m, 2H), 2.75-3.55 (m, 9H), 1.52-2.30 (m, 13H), 1.35 (m, 2H); MS (ESI) m/z 508 (M+H)+.

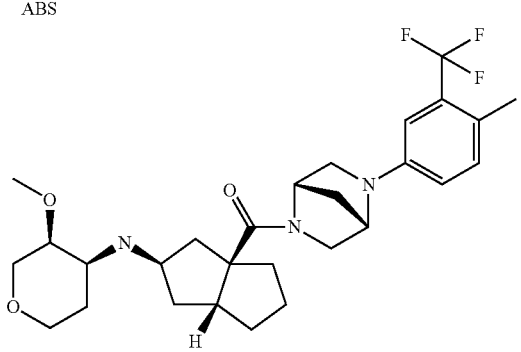 [SMILES: "ABS" ; CO[C@@H]1COCC[C@@H]1N[C@@H]1C[C@H]2CCC[C@@]2(C(=O)N2C[C@@H]3C[C@H]2CN3c2ccc(C)c(C(F)(F)F)c2)C1]

Example 19

1,5-anhydro-2,3-dideoxy-4-O-methyl-3-{[(2R,3aR, 6aR)-3a-({(1S,4S)-5-[4-methyl-3-(trifluoromethyl) phenyl]-2,5-diazabicyclo[2.2.1]hept-2-yl}carbonyl) octahydropentalen-2-yl]amino}-D-erythro-pentitol The trifluoroacetic acid salt of the title compound was prepared and purified using procedure similar to that described in Example 14, substituting 4-bromo-1-methyl-2-(trifluoromethyl)benzene for 2-bromo-1-fluoro-4-(trifluoromethyl)benzene. MS (ESI) m/z 522 (M+H)+.

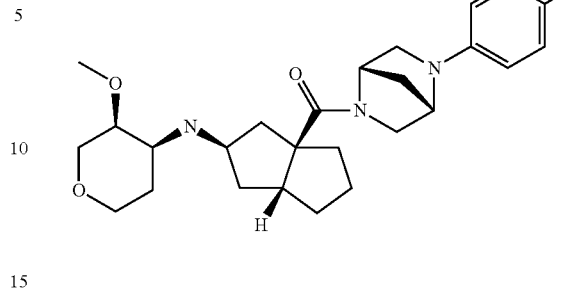

Example 20

1,5-anhydro-3-{[(2R,3aR,6aR)-3a-{[(1S,4S)-5-(3-chloro-4-fluorophenyl)-2,5-diazabicyclo[2.2.1]hept-2-yl]carbonyl}octahydropentalen-2-yl]amino}-2,3-dideoxy-4-O-methyl-D-erythro-pentitol The formic acid salt of the title compound was prepared and purified using procedure similar to that described in Example 14, substituting 4-bromo-2-chloro-1-fluorobenzene for 2-bromo-1-fluoro-4-(trifluoromethyl)benzene, and purified by preparative HPLC (Column: Phenomenex Synergi C18 150 mm*30 mm*4 μm; Mobile phase: from 17% acetonitrile in water (0.225% formic acid) to 37% acetonitrile in water (0.225% formic acid); Wavelength: 220 nm). MS (ESI) m/z 492 (M+H)+.

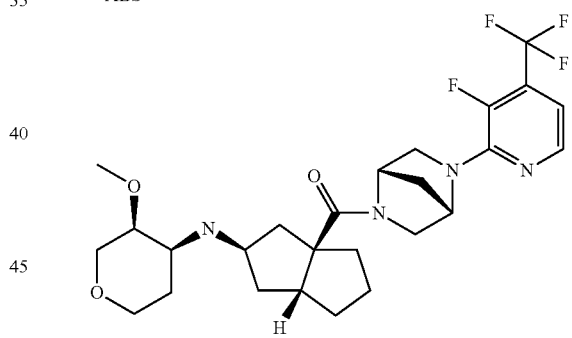

Example 21

1,5-anhydro-2,3-dideoxy-3-{[(2R,3aR,6aR)-3a-({(1S,4S)-5-[3-fluoro-4-(trifluoromethyl)pyridin-2-yl]-2,5-diazabicyclo[2.2.1]hept-2-yl}carbonyl)octahydropentalen-2-yl]amino}-4-O-methyl-D-erythro-pentitol The formic acid salt of the title compound was prepared using procedure similar to that described in Example 1° C., substituting 2-chloro-3-fluoro-4-(trifluoromethyl)pyridine for 2-bromo-1-fluoro-4-(trifluoromethyl)benzene. The crude product was purified by preparative HPLC (Column: Phenomenex Synergi C18 150*30 mm*4 μm; Mobile phase: from 17% acetonitrile in water (0.225% formic acid) to 37% acetonitrile in water (0.225% formic acid); Wavelength: 220 nm). ¹H NMR (400 MHz, CD₃OD) δ (ppm): 8.05 (d, J=5.6

Hz, 1H), 6.85 (m, 1H), 5.03 (m, 2H), 4.22 (m, 1H), 3.25-4.05 (m, 13H), 1.60-2.50 (m, 14H), 1.40 (m, 1H); MS (ESI) m/z 527 (M+H)+.

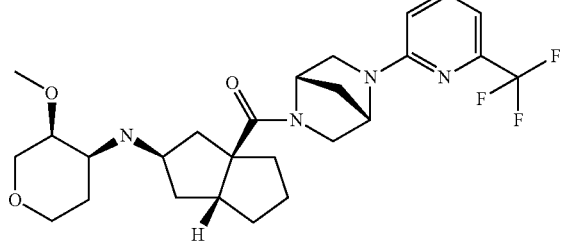

Example 22

1,5-anhydro-2,3-dideoxy-4-O-methyl-3-{[(2R,3aR,6aR)-3a-({(1S,4S)-5-[6-(trifluoromethyl)pyridin-2-yl]-2,5-diazabicyclo[2.2.1]hept-2-yl}carbonyl)octahydropentalen-2-yl]amino}-D-erythro-pentitol The formic acid salt of the title compound was prepared using procedure similar to that described in Example 11C, substituting 2-bromo-6-(trifluoromethyl)pyridine for 2-chloro-6-methyl-4-(trifluoromethyl)pyridine. The crude product was purified by preparative HPLC (Column: Phenomenex Synergi C18 150*30 mm*4 μm; Mobile phase: from 17% acetonitrile in water (0.225% formic acid) to 37% acetonitrile in water (0.225% formic acid); Wavelength: 220 nm). $^1$H NMR (400 MHz, CD$_3$OD) δ (ppm): 7.64 (t, J=8.0 Hz, 1H), 6.95 (d, J=8.0 Hz, 1H), 6.72 (m, 1H), 4.91-5.03 (m, 2H), 4.25 (m, 1H), 3.26-4.01 (m, 13H), 2.20-2.49 (m, 1H), 1.55-2.15 (m, 13H), 1.38 (m, 1H); MS (ESI) m/z 509 (M+H)+.

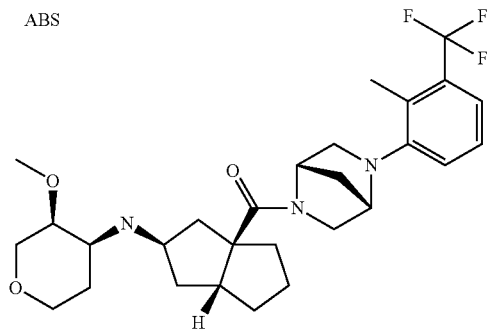 [SMILES: "ABS" ; CO[C@@H]1COCC[C@@H]1N[C@@H]1C[C@H]2CCC[C@@]2(C(=O)N2C[C@@H]3C[C@H]2CN3c2cccc(C(F)(F)F)c2C)C1]

Example 23

1,5-anhydro-2,3-dideoxy-4-O-methyl-3-{[(2R,3aR,6aR)-3a-({(1S,4S)-5-[2-methyl-3-(trifluoromethyl)phenyl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 14, substituting 1-bromo-2-methyl-3-(trifluoromethyl)benzene for 2-bromo-1-fluoro-4-(trifluoromethyl)benzene. MS (ESI) m/z 522 (M+H)+.

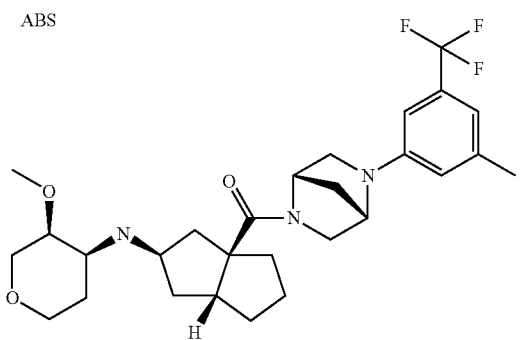 [SMILES: "ABS" ; CO[C@@H]1COCC[C@@H]1N[C@@H]1C[C@H]2CCC[C@@]2(C(=O)N2C[C@@H]3C[C@H]2CN3c2cc(C)cc(C(F)(F)F)c2)C1]

Example 24

1,5-anhydro-2,3-dideoxy-4-O-methyl-3-{[(2R,3aR,6aR)-3a-({(1S,4S)-5-[3-methyl-5-(trifluoromethyl)phenyl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 14, substituting 1-bromo-3-methyl-5-(trifluoromethyl)benzene for 2-bromo-1-fluoro-4-(trifluoromethyl)benzene. MS (ESI) m/z 522 (M+H)+.

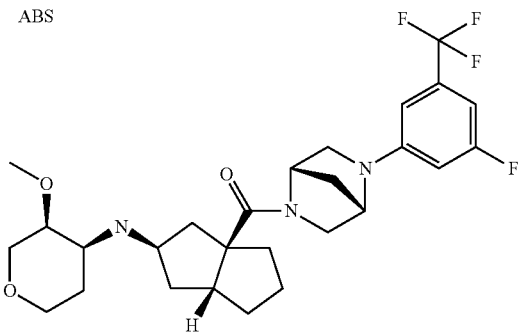 [SMILES: "ABS" ; CO[C@@H]1COCC[C@@H]1N[C@@H]1C[C@H]2CCC[C@@]2(C(=O)N2C[C@@H]3C[C@H]2CN3c2cc(F)cc(C(F)(F)F)c2)C1]

Example 25

1,5-anhydro-2,3-dideoxy-3-{[(2R,3aR,6aR)-3a-({(1S,4S)-5-[3-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol The trifluoroacetic acid salt of the title compound was prepared and purified according to the procedure similar to that described in Example 14, substituting 1-bromo-3-fluoro-5-(trifluoromethyl)benzene for 2-bromo-1-fluoro-4-(trifluoromethyl)benzene. $^1$H NMR (400 MHz, CD$_3$OD) δ (ppm): 6.66 (m, 3H), 5.00 (m, 1H), 4.70 (m, 1H), 4.25 (m, 1H), 3.98 (m, 1H), 3.15-3.85 (m, 12H), 2.20-2.50 (m, 1H), 1.61-2.15 (m, 13H), 1.43 (m, 1H); MS (ESI) m/z 526 (M+H)+.

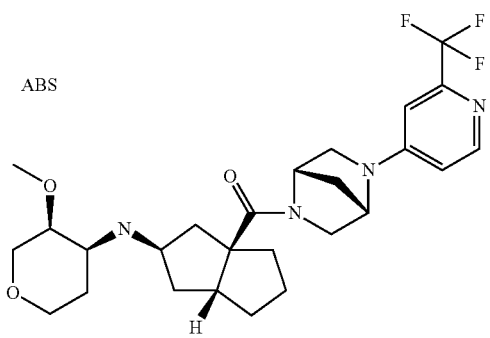 [SMILES: "ABS" ; CO[C@@H]1COCC[C@@H]1N[C@@H]1C[C@H]2CCC[C@@]2(C(=O)N2C[C@@H]3C[C@H]2CN3c2ccnc(C(F)(F)F)c2)C1]

Example 26

1,5-anhydro-2,3-dideoxy-4-O-methyl-3-{[(2R,3aR,6aR)-3a-({(1S,4S)-5-[2-(trifluoromethyl)pyridin-4-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 4-bromo-2-(trifluoromethyl)pyridine for 2-chloro-6-methyl-4-(trifluoromethyl)pyridine. $^1$H NMR (400 MHz, CD$_3$OD) δ (ppm): 8.20 (d, J=7.2 Hz, 1H), 6.85-7.50 (m, 2H), 4.95-5.13 (m, 2H), 4.20 (m, 1H), 3.23-3.95 (m, 13H), 1.60-2.50 (m, 14H), 1.37 (m, 1H); MS (ESI) m/z 509 (M+H)$^+$.

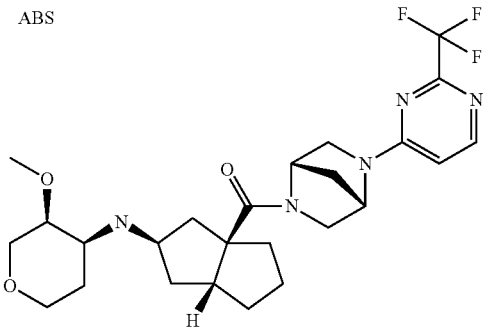 [SMILES: "ABS" ; CO[C@@H]1COCC[C@@H]1N[C@@H]1C[C@H]2CCC[C@@]2(C(=O)N2C[C@@H]3C[C@H]2CN3c2ccnc(C(F)(F)F)n2)C1]

Example 27

1,5-anhydro-2,3-dideoxy-4-O-methyl-3-{[(2R,3aR,6aR)-3a-({(1S,4S)-5-[2-(trifluoromethyl)pyrimidin-4-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 1C, substituting 4-chloro-2-(trifluoromethyl)pyrimidine for 2-chloro-6-methyl-4-(trifluoromethyl)pyridine. $^1$H NMR (400 MHz, CD$_3$OD) δ (ppm): 8.22 (d, J=6.4 Hz, 1H), 6.58-6.95 (m, 1H), 4.98-5.28 (m, 2H), 4.23 (t, J=13.6 Hz, 1H), 3.25-4.00 (m, 13H), 2.25-2.50 (m, 1H), 1.55-2.15 (m, 13H), 1.38 (m, 1H); MS (ESI) m/z 510 (M+H)$^+$.

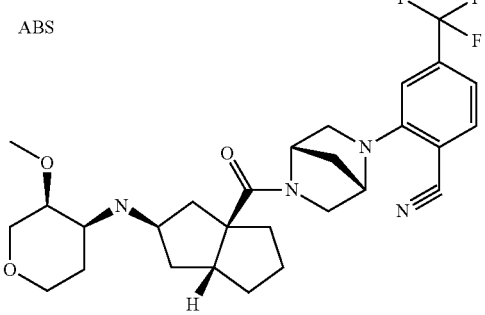

Example 28

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The trifluoroacetic acid salt of the title compound was prepared and purified using procedure similar to that described in Example 1C, substituting 2-fluoro-4-(trifluoromethyl)benzonitrile for 2-chloro-6-methyl-4-(trifluoromethyl)pyridine. MS (ESI) m/z 533 (M+H)$^+$.

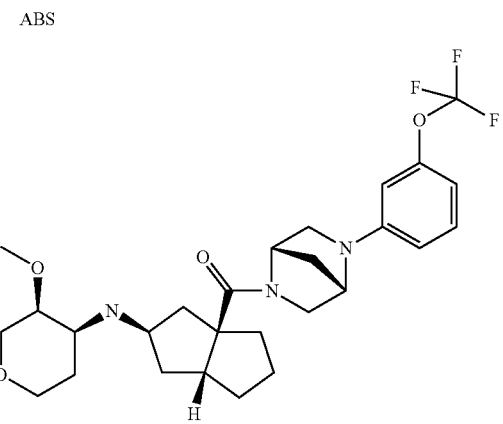

Example 29

1,5-anhydro-2,3-dideoxy-4-O-methyl-3-{[(2R,3aR,6aR)-3a-({(1S,4S)-5-[3-(trifluoromethoxy)phenyl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 1-bromo-3-(trifluoromethoxy)benzene for 2-chloro-6-methyl-4-(trifluoromethyl)pyridine. MS (ESI) m/z 524 (M+H)$^+$.

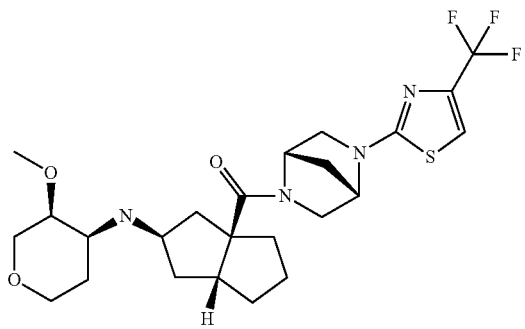

Example 30

1,5-anhydro-2,3-dideoxy-4-O-methyl-3-{[(2R,3aR,6aR)-3a-({(1S,4S)-5-[4-(trifluoromethyl)-1,3-thiazol-2-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 2-bromo-4-(trifluoromethyl)thiazole for 2-chloro-6-methyl-4-(trifluoromethyl)pyridine. $^1$H NMR (400 MHz, CD$_3$OD) δ (ppm): 7.27 (s, 1H), 4.96-4.98 (m, 1H), 4.80-4.86 (m, 2H), 4.28 (m, 1H), 4.02 (m, 1H), 3.26-3.87 (m, 11H), 2.28-2.50 (m, 1H), 1.61-2.20 (m, 13H), 1.42 (m, 1H); MS (ESI) m/z 515 (M+H)$^+$.

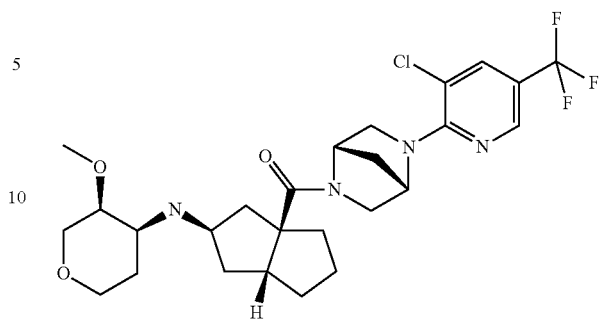

Example 32

1,5-anhydro-3-{[(2R,3aR,6aR)-3a-({(1S,4S)-5-[3-chloro-5-(trifluoromethyl)pyridin-2-yl]-2,5-diazabicyclo[2.2.1]hept-2-yl}carbonyl)octahydropentalen-2-yl]amino}-2,3-dideoxy-4-O-methyl-D-erythro-pentitol The trifluoroacetic acid salt of the title compound was prepared and purified using procedure similar to that described in Example 11C, substituting 2,3-dichloro-5-(trifluoromethyl)pyridine for 2-chloro-6-methyl-4-(trifluoromethyl)pyridine. $^1$H NMR (400 MHz, CD$_3$OD) δ (ppm): 8.32 (s, 1H), 7.85 (s, 1H), 5.15 (m, 1H), 4.10-4.30 (m, 2H), 3.30-4.05 (m, 13H), 2.24-2.50 (m, 1H), 1.60-2.15 (m, 13H), 1.40 (m, 1H); MS (ESI) m/z 543 (M+H)$^+$.

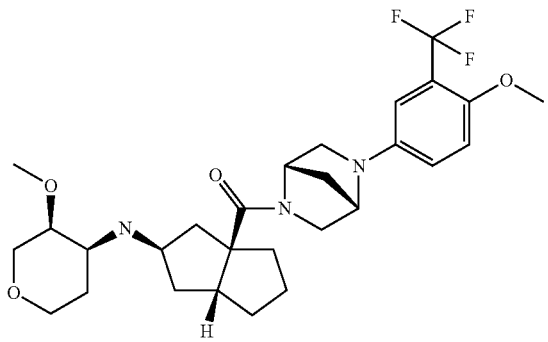

Example 31

1,5-anhydro-2,3-dideoxy-3-{[(2R,3aR,6aR)-3a-({(1S,4S)-5-[4-methoxy-3-(trifluoromethyl)phenyl]-2,5-diazabicyclo[2.2.1]hept-2-yl}carbonyl)octahydropentalen-2-yl]amino}-4-O-methyl-D-erythro-pentitol The trifluoroacetic acid salt of the title compound was prepared and purified using procedure similar to that described in Example 14, substituting 4-bromo-1-methoxy-2-(trifluoromethyl)benzene for 2-bromo-1-fluoro-4-(trifluoromethyl)benzene. MS (ESI) m/z 538 (M+H)$^+$.

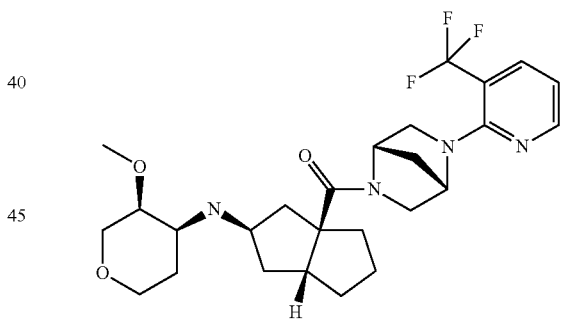

Example 33

1,5-anhydro-2,3-dideoxy-4-O-methyl-3-{[(2R,3aR,6aR)-3a-({(1S,4S)-5-[3-(trifluoromethyl)pyridin-2-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 2-chloro-3-(trifluoromethyl)pyridine for 2-chloro-6-methyl-4-(trifluoromethyl)pyridine. $^1$H NMR (400 MHz, CD$_3$OD) δ (ppm): 8.29 (d, J=4.0 Hz, 1H), 7.89 (d, J=4.0 Hz, 1H), 6.84 (m, 1H), 5.01 (m, 2H), 4.24 (m, 1H), 3.30-4.02 (m, 13H), 2.2-2.50 (m, 1H), 1.60-2.10 (m, 13H), 1.40 (m, 1H); MS (ESI) m/z 509 (M+H)$^+$.

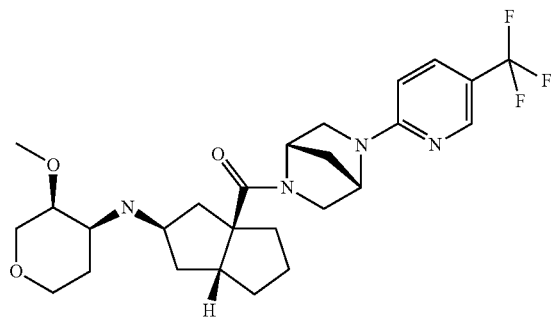

Example 34

1,5-anhydro-2,3-dideoxy-4-O-methyl-3-{[(2R,3aR, 6aR)-3a-({(1S,4S)-5-[5-(trifluoromethyl)pyridin-2-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 2-chloro-5-(trifluoromethyl)pyridine for 2-chloro-6-methyl-4-(trifluoromethyl)pyridine. $^1$H NMR (400 MHz, CD$_3$OD) δ (ppm): 8.29 (s, 1H), 7.85 (m, 1H), 6.84 (m, 1H), 5.05 (m, 2H), 4.18 (m, 1H), 3.30-3.95 (m, 13H), 2.20-2.50 (m, 1H), 1.55-2.10 (m, 13H), 1.35 (m, 1H); MS (ESI) m/z 509 (M+H)$^+$.

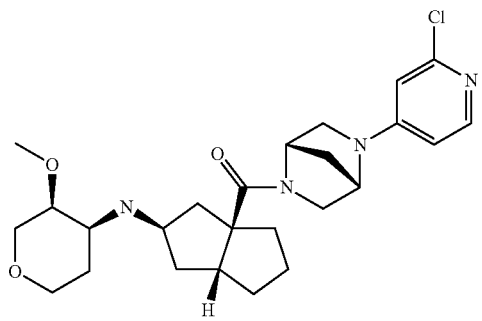

Example 35

1,5-anhydro-3-{[(2R,3aR,6aR)-3a-{[(1S,4S)-5-(2-chloropyridin-4-yl)-2,5-diazabicyclo[2.2.1]hept-2-yl]carbonyl}octahydropentalen-2-yl]amino}-2,3-dideoxy-4-O-methyl-D-erythro-pentitol The trifluoroacetic acid salt of the title compound was prepared and purified using procedure similar to that described in Example 11C, substituting 2-chloro-4-fluoropyridine for 2-chloro-6-methyl-4-(trifluoromethyl)pyridine. MS (ESI) m/z 475 (M+H)$^+$.

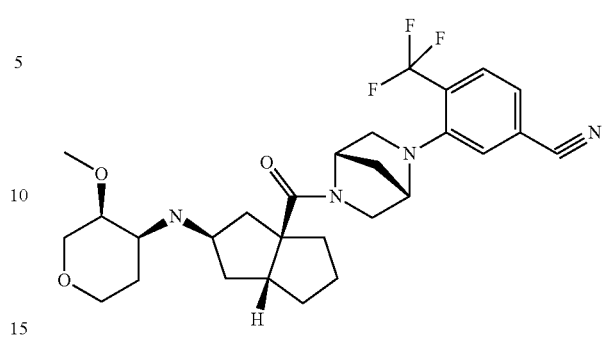

Example 36

1,5-anhydro-3-{[(2R,3aR,6aR)-3a-({(1S,4S)-5-[5-cyano-2-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The trifluoroacetic acid salt of the title compound was prepared and purified using procedure similar to that described in Example 11C, substituting 3-fluoro-4-(trifluoromethyl)benzonitrile for 2-chloro-6-methyl-4-(trifluoromethyl)pyridine. MS (ESI) m/z 533 (M+H)$^+$.

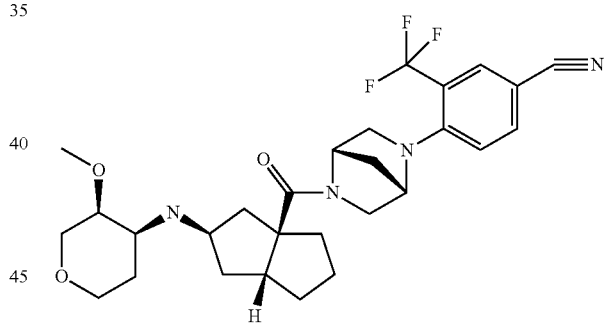

Example 37

1,5-anhydro-3-{[(2R,3aR,6aR)-3a-({(1S,4S)-5-[4-cyano-2-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The trifluoroacetic acid salt of the title compound was prepared and purified using procedure similar to that described in Example 1C, substituting 4-fluoro-3-(trifluoromethyl)benzonitrile for 2-chloro-6-methyl-4-(trifluoromethyl)pyridine. $^1$H NMR (400 MHz, CD$_3$OD) δ (ppm): 7.92 (s, 1H), 7.70 (d, J=8.0 Hz, 1H), 7.16 (d, J=8.0 Hz, 1H), 4.70 (m, 1H), 4.24 (m, 1H), 3.30-4.03 (m, 14H), 2.25-2.53 (m, 1H), 1.60-2.17 (m, 13H), 1.40 (m, 1H); MS (ESI) m/z 533 (M+H)$^+$.

RAC

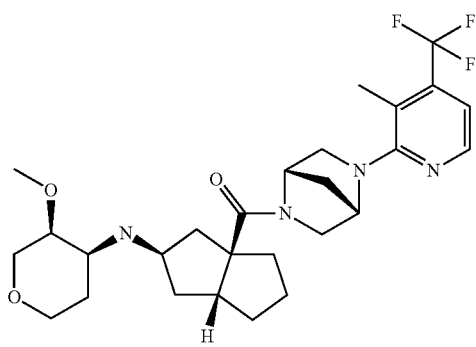

Example 38

1,5-anhydro-2,3-dideoxy-4-O-methyl-3-{[(2R,3aR, 6aR)-3a-({(1S,4S)-5-[3-methyl-4-(trifluoromethyl) pyridin-2-yl]-2,5-diazabicyclo[2.2.1]hept-2-yl}carbonyl)octahydropentalen-2-yl]amino}-D-erythro-pentitol The trifluoroacetic acid salt of the title compound was prepared and purified using procedure similar to that described in Example 11C, substituting 2-chloro-3-methyl-4-(trifluoromethyl)pyridine for 2-chloro-6-methyl-4-(trifluoromethyl)pyridine. MS (ESI) m/z 523 (M+H)$^+$.

RAC

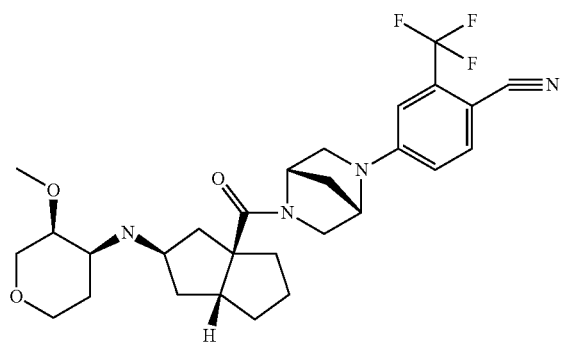

Example 39

1,5-anhydro-3-{[(2R,3aR,6aR)-3a-({(1S,4S)-5-[4-cyano-3-(trifluoromethyl)phenyl]-2,5-diazabicyclo [2.2.1]hept-2-yl}carbonyl)octahydropentalen-2-yl] amino}-2,3-dideoxy-4-O-methyl-D-erythro-pentitol The trifluoroacetic acid salt of the title compound was prepared and purified using the procedure analogous to that described in Example 14, substituting 4-bromo-2-(trifluoromethyl)benzonitrile for 2-bromo-1-fluoro-4-(trifluoromethyl)benzene. $^1$H NMR (400 MHz, CD$_3$OD) δ (ppm): 8.48 (s, 1H), 7.68 (d, 1H), 7.21-7.23 (m, 2H), 7.11 (s, 1H), 4.2-4.96 (m, 2H), 4.21 (t, 1H), 3.81-3.94 (m, 1H), 3.10-3.92 (m, 12H), 2.45-1.58 (m, 14H), 1.32-1.45 (m, 1H); MS (ESI) m/z 533 (M+H)$^+$.

ABS

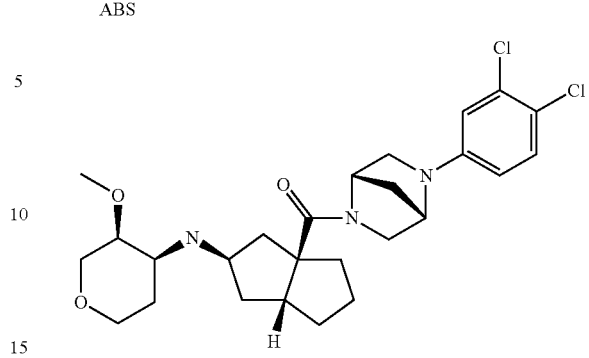

Example 40

1,5-anhydro-2,3-dideoxy-3-{[(2R,3aR,6aR)-3a-{[(1S,4S)-5-(3,4-dichlorophenyl)-2,5-diazabicyclo [2.2.1]hept-2-yl]carbonyl}octahydropentalen-2-yl] amino}-4-O-methyl-D-erythro-pentitol The trifluoroacetic acid salt of the title compound was prepared and purified using procedure similar to that described in Example 14, substituting 4-bromo-1,2-dichlorobenzene for 2-bromo-1-fluoro-4-(trifluoromethyl)benzene. MS (ESI) m/z 508 (M+H)$^+$.

ABS

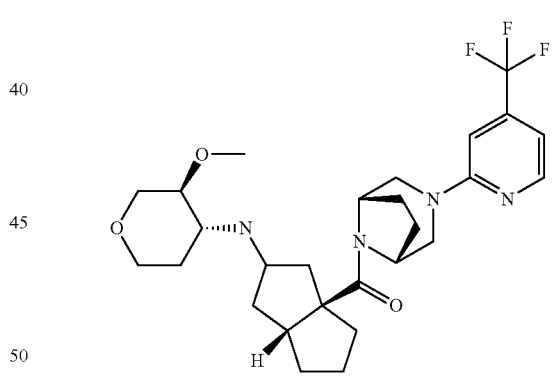

Example 41

1,5-anhydro-2,3-dideoxy-4-O-methyl-3-{[(2R,3aR, 6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-threo-pentitol The title compound was obtained from the chiral SFC purification of the diastereomeric mixture of Example 8D. MS (ESI) m/z 523 (M+H)$^+$.

ABS

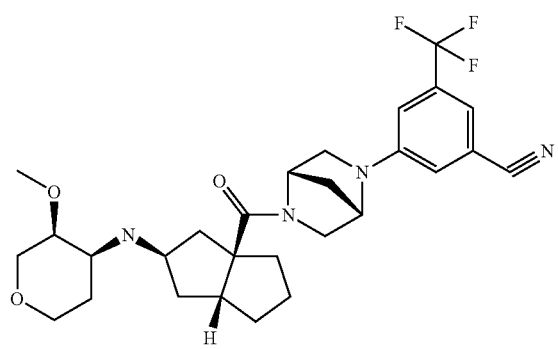

Example 42

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The title compound was prepared using procedure similar to that described in Example 11C, substituting 3-bromo-5-(trifluoromethyl)benzonitrile for 2-chloro-6-methyl-4-(trifluoromethyl)pyridine. The crude product was purified by preparative HPLC (Column: Phenomenex Synergi C18 150 mm*30 mm*4 μm; Mobile phase: from 17% acetonitrile in water (0.225% formic acid) to 37% acetonitrile in water (0.225% formic acid); Wavelength: 220 nm) to provide the formic acid salt of the title compound. $^1$H NMR (400 MHz, CD$_3$OD) δ (ppm): 7.21-7.23 (m, 2H), 7.11 (s, 1H), 4.2-4.96 (m, 2H), 4.21 (t, 1H), 3.81-3.94 (m, 1H), 3.10-3.92 (m, 12H), 2.45-2.53 (m, 0.5H), 1.58-2.15 (m, 13.5H), 1.32-1.45 (m, 1H); MS (ESI) m/z 533 (M+H)$^+$.

ABS

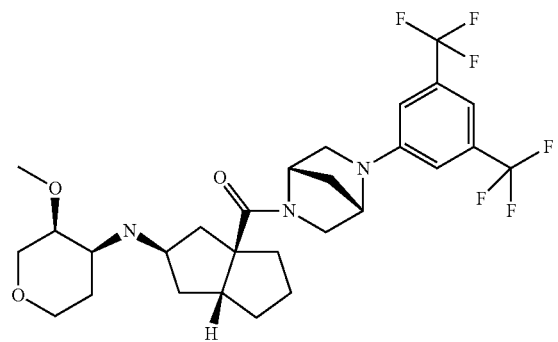

Example 43

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The title compound was prepared using the procedure analogous to that described in Example 14, substituting 1-bromo-3,5-bis(trifluoromethyl)benzene for 2-bromo-1-fluoro-4-(trifluoromethyl)benzene. The crude product was purified by preparative HPLC (Column: Phenomenex Synergi C18 150 mm*30 mm*4 μm; Mobile phase: from 17% acetonitrile in water (0.225% formic acid) to 37% acetonitrile in water (0.225% formic acid); Wavelength: 220 nm) to provide the formic acid salt of the title compound. $^1$H NMR (400 MHz, CD$_3$OD) δ (ppm): 7.11-7.15 (m, 3H), 4.798-5.02 (m, 2H), 4.37 (t, 1H), 3.19-3.98 (m, 13H), 1.62-2.50 (m, 14H), 1.38-1.50 (m, 1H); MS (ESI) m/z 575 (M+H)$^+$.

ABS

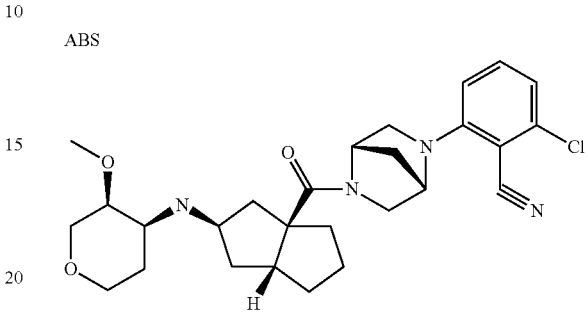

Example 44

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl]amino}-2,3-dideoxy-4-O-methyl-D-erythro-pentitol The trifluoroacetic acid salt of the title compound was prepared and purified using the procedure analogous to that described in Example 11C, substituting 2-chloro-6-fluorobenzonitrile for 2-chloro-6-methyl-4-(trifluoromethyl)pyridine. $^1$H NMR (400 MHz, CD$_3$OD) δ (ppm): 7.49 (m, 1H), 6.85-6.93 (m, 2H). 4.78-4.92 (m, 2H), 4.25 (m, 1H), 3.12-3.48 (m, 13H), 1.62-2.50 (m, 14H), 1.38-1.50 (m, 1H); MS (ESI) m/z 499 (M+H)$^+$.

ABS

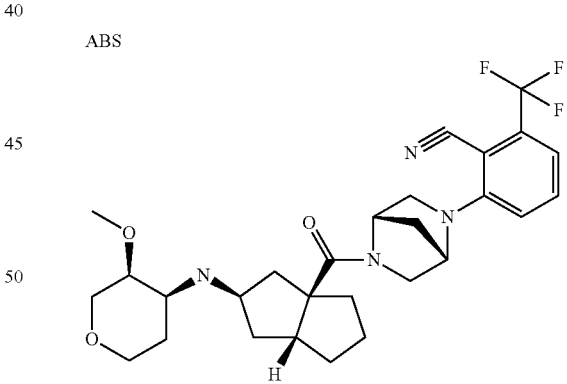

Example 45

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The trifluoroacetic acid salt of the title compound was prepared and purified using procedure similar to that described in Example 11C, substituting 2-fluoro-6-(trifluoromethyl)benzonitrile for 2-chloro-6-methyl-4-(trifluoromethyl)pyridine. $^1$H NMR (400 MHz, CD$_3$OD) δ (ppm): 7.60 (t, 1H), 7.19-7.26 (m, 2H). 4.87-4.97 (m, 2H), 4.39 (t, 1H), 3.90-4.12 (m, 2H), 3.12-3.48 (m, 12H), 1.62-2.50 (m, 14H), 1.38-1.50 (m, 1H); MS (ESI) m/z 533 (M+H)$^+$.

ABS

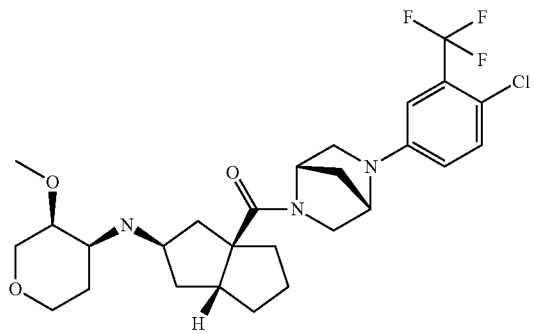

Example 46

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The title compound was prepared and purified as a trifluoroacetic acid salt using the procedure analogous to that described in Example 14, substituting 4-iodo-1-chloro-2-(trifluoromethyl)benzene for 2-bromo-1-fluoro-4-(trifluoromethyl)benzene. $^1$H NMR (400 MHz, CD$_3$OD) δ 7.38 (d, 1H), 6.94 (s, 1H), 6.87 (d, 1H), 4.96 (t, 1H), 4.71 (d, 1H), 4.27 (t, 1H), 3.91-4.05 (m, 1H), 3.10-3.86 (m, 12H), 1.56-2.35 (m, 14H), 1.42-1.50 (m, 1H); MS (ESI) m/z 543 (M+H)$^+$.

ABS

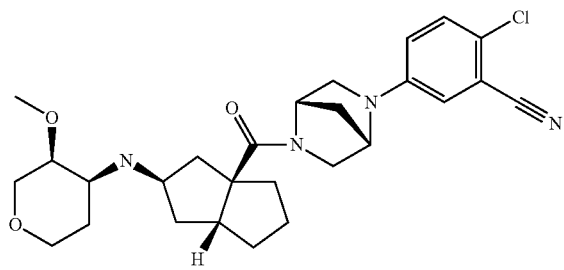

Example 47

1,5-anhydro-3-{[(2R,3aR,6aR)-3a-{[(1S,4S)-5-(4-chloro-3-cyanophenyl)-2,5-diazabicyclo[2.2.1]hept-2-yl]carbonyl}octahydropentalen-2-yl]amino}-2,3-dideoxy-4-O-methyl-D-erythro-pentitol The trifluoroacetic acid salt of the title compound was prepared and purified using the procedure analogous to that described in Example 14, substituting 5-bromo-2-chlorobenzonitrile for 2-bromo-1-fluoro-4-(trifluoromethyl)benzene. MS (ESI) m/z 499 (M+H)$^+$.

ABS

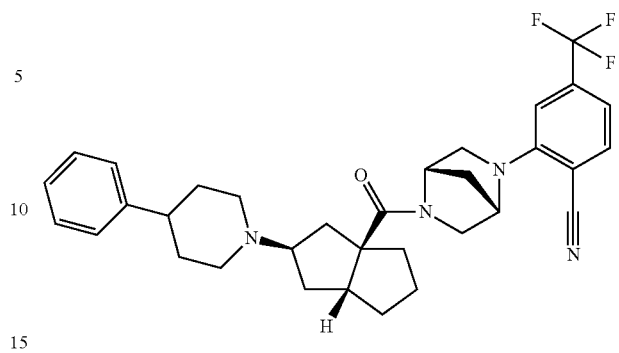

Example 48

2-[(1S,4S)-5-{[(2R,3aR,6aR)-2-(4-phenylpiperidin-1-yl)hexahydropentalen-3a(1H)-yl]carbonyl}-2,5-diazabicyclo[2.2.1]hept-2-yl]-4-(trifluoromethyl)benzonitrile Example 48A (S)-benzyl 4-(2,5-dimethyl-1H-pyrrol-1-yl)cyclopent-2-enecarboxylate A solution of compound in Example 1B (11.04 g, 50.4 mmol), and 40 mL of 2.5 M NaOH in 100 mL of MeOH was stirred at room temperature for 45 minutes, then concentrated under reduced pressure to remove MeOH. The residual aqueous solution was added to a stirred mixture of 20 g of citric acid and 100 mL of dichloromethane. The phases were separated and the aqueous phase was extracted with two additional portions of dichloromethane. The organic phase was dried and concentrated.

To the stirred solution of a mixture of the residue obtained, benzyl alcohol (10 mL, 96 mmol), and DMAP (1.74 g, 14 mmol) in dichloromethane (50 mL) was added EDC (13 g, 69 mmol), in five equal portions over 30 minutes. After 18 hours, the solution was concentrated under reduced pressure, and the residual syrup partitioned between ether and water. The organic phase was washed with water and brine, with one back-extraction of the aqueous phase with ether. The combined organic phase was dried, and concentrated under reduced pressure. The crude product was purified by column chromatography (SiO$_2$, petroleum ether:ethyl acetate from 50:1 to 10:1) to afford the title compound as colorless oil.

Example 48B (1R,4S)-benzyl 1-(3-bromopropyl)-4-(2,5-dimethyl-1H-pyrrol-1-yl)cyclopent-2-enecarboxylate To a solution of Example 48A (21.94 g, 74.4 mmol) in tetrahydrofuran (200 ml) was added dropwise lithium hexamethyl bis(trimethylsilyl)amide (1 M in tetrahydrofuran, 119 mL) at −50° C. The reaction mixture was stirred for 1 hour at the same temperature. 1,3-dibromopropane (150 g, 744 mmol) was added dropwise over 1 hour. The reaction mixture was allowed to warm to −20° C. and stirred at the same temperature for 1 hour. LCMS showed that the reaction was complete. The reaction mixture was quenched with an aqueous ammonium chloride solution (6%, 600 mL), and extracted with ethyl acetate. The organic fraction was washed with aqueous ammonium chloride (6%), brine, dried with sodium sulfate, filtered, and concentrated in vacuo. The residue was purified by silica gel column chromatography (petroleum ether:ethyl acetate=80:1) to give the title compound.

Example 48C (2R,3aR,6aR)-benzyl 2-(2,5-dimethyl-1H-pyrrol-1-yl)octahydropentalene-3a-carboxylate To a solution of compound in Example 48B (19.5 g, 47 mmol) and azobisisobutyronitrile (1.6 g, 10 mmol) in toluene (1.8 L) at 110° C. was added a solution of tributyltinhydride (32 mL, 119 mmol) in toluene (200 mL) over 1 hour. After refluxing for 3 hours, the reaction mixture was quenched with a saturated aqueous potassium fluoride solution (200 mL), and extracted with ethyl acetate. The organic fraction was washed with brine, dried with sodium sulfate, filtered, and concentrated in vacuo. The residue was purified by column chromatography (SiO$_2$, petroleum ether:ethyl acetate=50:1) to give the title compound.

Example 48D (2R,3aR,6aR)-benzyl 2-aminooctahydropentalene-3a-carboxylate

To a aqueous solution of NH$_2$OH.HCl (8.4 g, 121.2 mmol) and NaOH (2.2 g, 19.54 mmol) in H$_2$O (20 mL) was added a solution of Example 48C (2.81 g, 8.36 mmol) in MeOH (70 mL) and the mixture was heated at 65° C. for 8 hours. The mixture was cooled to room temperature, sufficient water was added and MeOH was removed under reduced pressure. The resulting slurry was adjusted to pH=10 with NaOH solution (2.5 N) and extracted with dichloromethane. The combined organic layer was washed with brine, dried over Na$_2$SO$_4$, filtered, and concentrated to give a crude product, which was purified by column chromatography (SiO$_2$, dichloromethane:MeOH from 100:1 to 10:1) to get the title compound.

Example 48E (2R,3aR,6aR)-benzyl 2-(4-phenylpiperidin-1-yl)octahydropentalene-3a-carboxylate The mixture of Example 48D, (3-bromo-1-bromomethyl-propyl)-benzene (1.82 g, 5.9 mmol) and N,N-diisopropyl-ethyl amine (2.1 g, 16.2 mmol) in acetonitrile (10 ml) was stirred at 120° C. in a microwave reactor for 2 hours. Water (15 mL) was added and extracted with ethyl acetate. The combined organics were dried and concentrated. The residue was purified by column chromatography (SiO$_2$, petroleum ether: ethyl acetate from 50:1 to 10:1) to provide the title compound as an oil. $^1$H NMR (400 MHz, CDCl$_3$) δ (ppm): 7.10-7.31 (m, 10H), 5.01-5.08 (s, 2H), 3.17 (d, 2H), 2.76 (q, 1H), 2.52-2.69 (m, 1H), 2.35-2.48 (m, 1H), 2.17-2.22 (m, 1H), 1.82-2.15 (m, 5H), 1.61-1.80 (m, 6H), 1.39-1.60 (m, 5H), 1.17-1.27 (m, 1H).

Example 48F (2R,3aR,6aR)-2-(4-phenylpiperidin-1-yl)octahydropentalene-3a-carboxylic acid The mixture of Example 48F (2.1 g, 5.2 mmol) and Pd—C (0.5 g) in MeOH (15 mL) was stirred under hydrogen at 50 psi for 1 hour at room temperature. The mixture was filtered and cake was washed with MeOH. The filtrate was concentrated to afford the title compound (1.7 g) as a colorless solid. $^1$H NMR (400 MHz, CDCl$_3$) δ (ppm): 11.19 (brs, 1H), 7.10-7.32 (m, 5H), 3.63 (d, 2H), 3.52 (s, 1H), 2.90-2.99 (m, 2H), 2.88 (q, 1H), 2.74 (t, 1H), 2.58-2.65 (m, 1H), 2.34-2.50 (m, 3H), 2.25-2.28 (m, 1H), 2.13-2.17 (m, 1H), 1.88-1.96 (m, 4H), 1.37-1.60 (m, 3H), 1.19-1.27 (m, 1H).

Example 48G (1S,4S)-tert-butyl 5-((2R,3aR,6aR)-2-(4-phenylpiperidin-1-yl)octahydropentalene-3a-carbonyl)-2,5-diazabicyclo[2.2.1]heptane-2-carboxylate To a solution of compound in Example 48F (1.7 g, 5.4 mmol) in dichloromethane (15 mL) was added oxalyl chloride (3.4 g, 27 mmol) followed by a drop of DMF under ice bath. After stirring for 30 minutes at room temperature, the mixture was concentrated to dryness. Dichloromethane (15 ml) was added and solution of (1S,4S)-tert-butyl 2,5-diazabicyclo[2.2.1]heptane-2-carboxylate (1.18 g, 5.94 mmol) and diisopropylethylamine (4.2 g, 32.4 mmol) in dichloromethane (3 ml) was added. The mixture was stirred at room temperature overnight. The mixture was concentrated and purified on silica column to afford the title compound as a solid.

Example 48H (1S,4S)-2,5-diazabicyclo[2.2.1]heptan-2-yl((2R,3aR,6aR)-2-(4-phenylpiperidin-1-yl)octahydropentalen-3a-yl)methanone To a solution of compound in Example 48G (300 mg, 0.61 mmol) in dioxane (5 ml) was added HCl in dioxane (4N, 20 mL) at 0° C. The mixture was stirred at room temperature for 1 hour. The mixture was concentrated and the residue was dissolved in water (10 mL) and NaHCO$_3$ was added to adjust the pH to about 9-10. The mixture was extracted with ethyl acetate. The combined organics were washed with brine, dried and concentration to afford the title compound (250 mg) as a solid.

Example 48I

2-[(1S,4S)-5-{[(2R,3aR,6aR)-2-(4-phenylpiperidin-1-yl)hexahydropentalen-3a(1H)-yl]carbonyl}-2,5-diazabicyclo[2.2.1]hept-2-yl]-4-(trifluoromethyl)benzonitrile To a solution of compound in Example 48H (125 mg, 0.25 mmol) in DMSO (1 ml) was added 2-fluoro-4-trifluoromethyl-benzonitrile (118 mg, 0.63 mmol) and diisopropyethylamine (129 mg, 1.0 mmol). The mixture was heated at 100° C. overnight. After cooling to room temperature, the mixture was diluted with DMSO (2 mL) and purified by preparative HPLC (Column: Phenomenex Gemini C18 250*21.2 mm*8 μm; Mobile phase: from 70% acetonitrile in water (ammonia (pH 10)) to 85% acetonitrile in water (ammonia (pH 10)); Wavelength: 220 nm) to afford the title compound as a white solid. $^1$H NMR (400 MHz, CD$_3$OD) δ (ppm): δ 7.49 (d, 1H), 7.13-7.23 (m, 5H), 6.78-6.87 (m, 2H), 4.96 (d, 1H), 4.69 (s, 1H), 3.0-4.27 (t, 10H), 1.5-4.25 (m, 17H); MS (ESI) m/z 563 (M+H)$^+$.

ABS

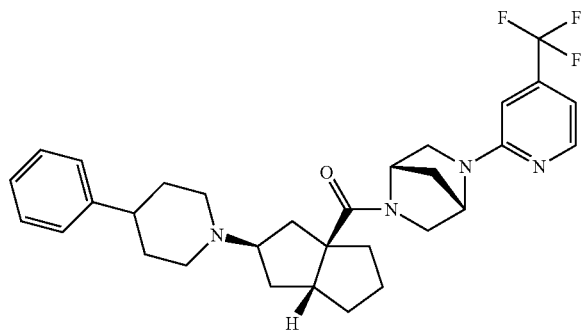

Example 49

[(2R,3aR,6aR)-2-(4-phenylpiperidin-1-yl)hexahydropentalen-3a(1H)-yl]{(1S,4S)-5-[4-(trifluoromethyl)pyridin-2-yl]-2,5-diazabicyclo[2.2.1]hept-2-yl}methanone To a solution of compound in Example 48H (125 mg, 0.25 mmol) in DMSO (1 mL) was added 2-chloro-4-trifluoromethyl-pyridine (114 mg, 0.63 mmol) and diisopropylethylamine (129 mg, 1.0 mmol). The mixture was heated at 100° C. overnight. After cooling to room temperature, the mixture was diluted with DMSO (2 mL) and purified by preparative HPLC (Column: Phenomenex Gemini C18 250*21.2 mm*8 μm; Mobile phase: from 70% acetonitrile in water (Ammonia (pH 10)) to 85% acetonitrile in water (Ammonia (pH 10)); Wavelength: 220 nm) to afford the title compound (35 mg, 26%) as a white solid. $^1$H NMR (400 MHz, CD$_3$OD) δ (ppm): 8.18 (s, 1H), 7.10-7.30 (m, 5H), 6.68 (d, 1H), 6.44 (s, 1H), 4.60-5.10 (m, 2H), 3.20-3.80 (m, 9H), 1.20-2.90 (m, 17H); MS (ESI) m/z 539 (M+H)$^+$.

ABS

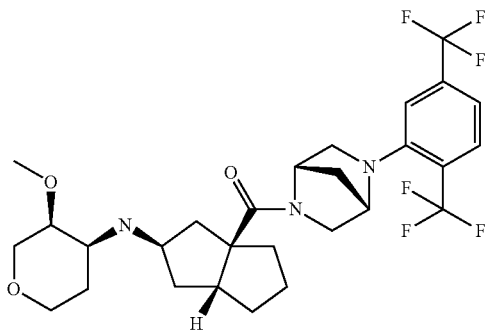

Example 50

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol The title compound was prepared and using the procedure analogous to that described in Example 14, substituting 2-bromo-1,4-bis(trifluoromethyl)benzene for 2-bromo-1-fluoro-4-(trifluoromethyl)benzene. The crude product was purified by preparative HPLC (Column: Phenomenex Synergi C18 150 mm*30 mm*4 μm; Mobile phase: from 17% acetonitrile in water (0.225% formic acid) to 37% acetonitrile in water (0.225% formic acid); Wavelength: 220 nm) to yield the formic acid salt of the title compound. $^1$H NMR (400 MHz, CD$_3$OD) δ (ppm): 8.50 (s, 1H), 7.82 (d, 1H), 7.22-7.36 (m, 2H), 4.96 (m, 1H), 4.60 (d, 1H), 4.27 (t, 1H), 3.65-4.10 (m, 4H), 3.30-3.65 (m, 10H), 1.60-2.52 (m, 13H), 1.39-1.49 (m, 1H); MS (ESI) m/z 576 (M+H)$^+$.

ABS

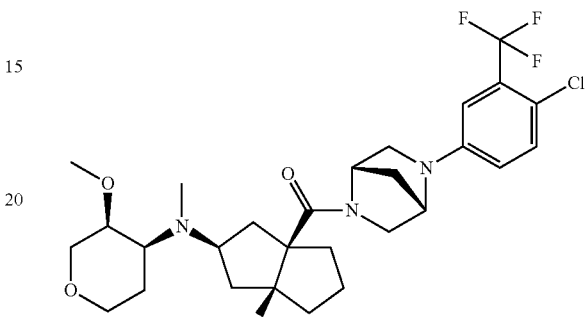

Example 51

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol A solution of compound in Example 46 (20 mg, 0.04 mmol), formic acid (19 mg, 0.4 mmol) and paraformaldehyde (37 mg, 0.4 mmol) in dioxane (0.5 mL) was stirred at 100° C. for 10 hours. TLC showed that starting material was consumed. The solid was filtered and the mixture was concentrated to give a crude product, which was purified by prep-HPLC(HPLC condition: Column: Boston Symmetrix ODS-H 150*30 mm*5 μm; Mobile phase: from 37% acetonitrile in water (0.1% TFA) to 57% acetonitrile in water (0.1% TFA); Wavelength: 220 nm) afforded the title compound as TFA salt. $^1$H NMR (400 MHz, CD$_3$OD) δ (ppm): 7.32-7.39 (m, 1H), 6.71-6.92 (m, 2H), 4.61-4.67 (m, 1H), 3.32-4.35 (m, 14H), 3.10-3.22 (m, 2H), 2.47-2.85 (m, 4H), 1.24-2.39 (m, 13H); MS (ESI) m/z 556 (M+H)$^+$.

ABS

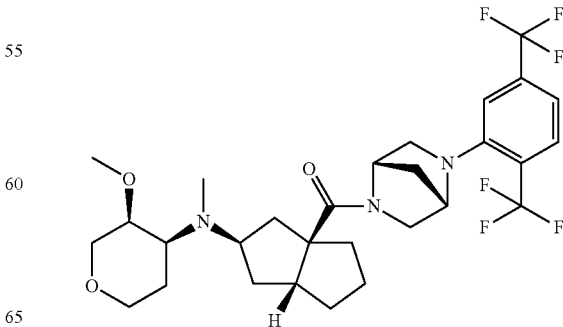

Example 52

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The trifluoroacetic acid salt of the title compound was prepared and purified using procedure similar to that described in Example 51, substituting Example 50 for Example 46. $^1$H NMR (400 MHz, CD$_3$OD) δ (ppm): 7.81-7.83 (d, 1H), 7.21-7.40 (m, 2H), 4.58 (s, 1H), 4.25-4.39 (m, 1H), 3.35-4.10 (m, 15H), 1.36-2.84 (m, 17H).

ABS

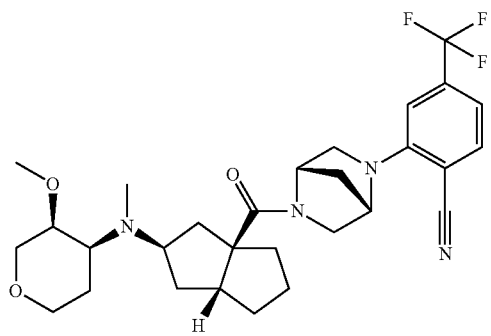

Example 53

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The trifluoroacetic acid salt of the title compound was prepared and purified using procedure similar to that described in Example 51, substituting Example 28 for Example 46. $^1$H NMR (400 MHz, CD$_3$OD) δ (ppm): 7.70-7.72 (d, 1H), 7.04-7.13 (m, 2H), 4.96-5.13 (m, 2H), 3.35-4.39 (m, 15H), 1.33-2.82 (m, 17H).

ABS

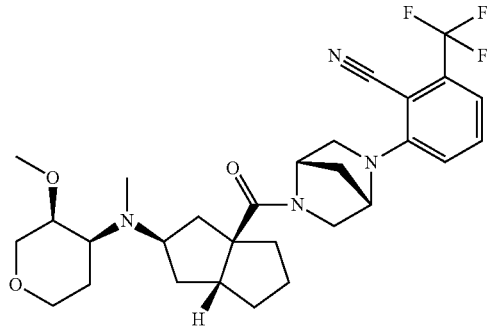

Example 54

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The title compound was prepared and purified using procedure similar to that described in Example 51, substituting Example 45 for Example 46. After HPLC separation the desired fractions needed were combined and evaporated to remove acetonitrile and treated with saturated NaHCO$_3$ solution, extracted with dichloromethane. The combined organic layers were concentrated in vacuum to afford the title compound as free base. $^1$H NMR (400 MHz, CD$_3$OD) δ (ppm): 7.50-7.58 (t, 1H), 7.16-7.23 (m, 2H), 4.92-4.99 (m, 3H), 4.21-4.33 (m, 1.5H), 3.33-4.07 (m, 16.5H), 1.55-2.85 (m, 12H), 1.32-1.42 (m, 1H).

ABS

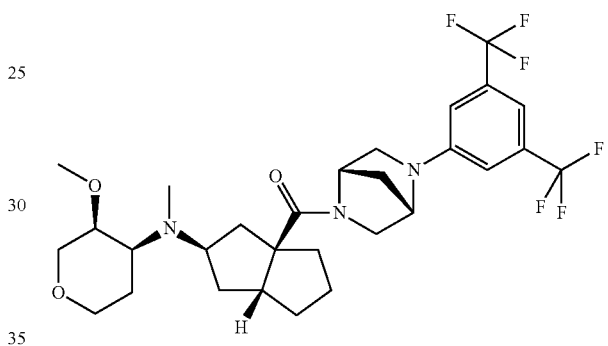

Example 55

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The trifluoroacetic acid salt of the title compound was prepared and purified using procedure similar to that described in Example 51, substituting Example 43 for Example 46. $^1$H NMR (400 MHz, CD$_3$OD) δ (ppm): 7.50-7.58 (t, 1H), 7.16-7.23 (m, 2H), 4.92-4.99 (m, 3H), 3.33-4.33 (m, 18H), 1.55-2.85 (m, 12H), 1.32-1.42 (m, 1H).

ABS

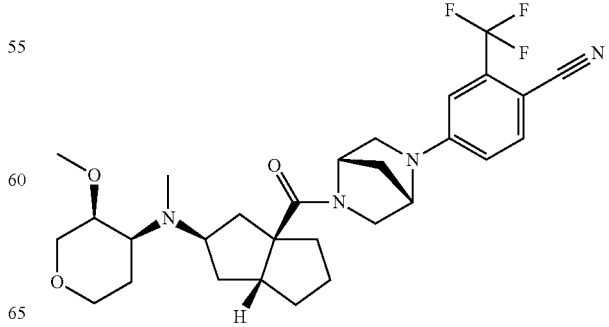

Example 56

1,5-anhydro-3-{[(2R,3aR,6aR)-3a-({(1S,4S)-5-[4-cyano-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The title compound was prepared and purified using procedure similar to that described in Example 51, substituting Example 39 for Example 46. After HPLC separation the desired fractions needed were combined and evaporated to remove acetonitrile and treated with saturated $NaHCO_3$ solution, extracted with dichloromethane. The combined organic layers were concentrated in vacuum to afford the title compound as free base. $^1$H NMR (400 MHz, $CD_3OD$) δ (ppm): 7.67-7.69 (d, 1H), 6.91-7.00 (m, 2H), 4.93-5.00 (m, 2H), 4.01-4.02 (m, 1H), 3.31-4.08 (m, 13H), 2.46-2.71 (m, 4H), 1.52-2.34 (m, 13H), 1.32-1.41 (m, 1H).

ABS

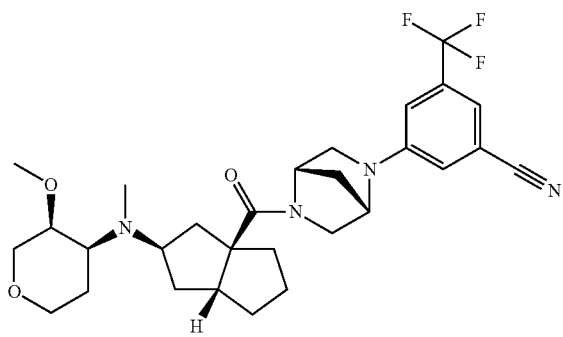

Example 57

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol The title compound was prepared and purified using procedure similar to that described in Example 51, substituting Example 42 for Example 46. After HPLC separation the desired fractions needed were combined and evaporated to remove acetonitrile and treated with saturated $NaHCO_3$ solution, extracted with dichloromethane. The combined organic layers were concentrated in vacuum to afford the title compound as free base. $^1$H NMR (400 MHz, $CD_3OD$) δ (ppm): 8.49 (s, 1H), 7.12-7.23 (m, 3H), 4.93 (s, 1H), 4.74 (s, 1H), 4.60 (s, 1H), 4.16-4.29 (m, 1H), 3.31-4.04 (m, 11H), 3.09-3.23 (m, 1H), 2.70 (s, 1H), 2.51 (s, 2H), 1.52-2.14 (m, 13H), 1.27-1.42 (m, 1H).

ABS

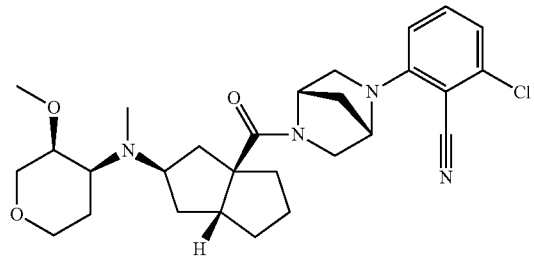

Example 58

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl](methyl)amino}-2,3-dideoxy-4-O-methyl-D-erythro-pentitol The title compound was prepared and purified using procedure similar to that described in Example 51, substituting Example 44 for Example 46. After HPLC separation the desired fractions needed were combined and evaporated to remove acetonitrile and treated with saturated $NaHCO_3$ solution, extracted with dichloromethane. The combined organic layers were concentrated in vacuum to afford the title compound as free base. $^1$H NMR (400 MHz, $CD_3OD$) δ (ppm): 7.35-7.39 (t, 1H), 6.85-6.90 (m, 2H), 4.91 (s, 1H), 3.29-4.30 (m, 15H), 2.66-2.77 (m, 3H), 2.23-2.5442 (m, 1H), 1.52-2.17 (m, 13H), 1.30-1.46 (m, 1H).

ABS

Example 59

[(2R,3aR,6aR)-2-(morpholin-4-yl)hexahydropentalen-3a(1H)-yl]{(1S,4S)-5-[4-(trifluoromethyl)pyridin-2-yl]-2,5-diazabicyclo[2.2.1]hept-2-yl}methanone A solution of Example 1H (100 mg, 0.25 mmol), diisopropylethylamine (115 mg, 0.89 mmol) and 1-bromo-2-(2-bromoethoxy)ethane (89 mg, 0.38 mmol) in acetonitrile (1.5 mL) was stirred at 120° C. under microwave irradiation for 1 hour. The mixture was extracted with ethyl acetate (10 mL×2). The organic layer was washed with brine, dried over sodium sulfate and concentrated to give a crude product, which was purified by prep-HPLC (Column: Phenomenex Gemini C18 250*21.2 mm*8 μm; Mobile phase: from 30% acetonitrile in water (Ammonia (pH 10)) to 50% acetonitrile in water (Ammonia (pH 10)); Wavelength: 220 nm) afforded the title compound. $^1$H NMR (400 MHz, CD$_3$OD) δ (ppm): 6.55-6.57 (d, 1H), 5.58 (s, 1H), 5.35-5.37 (d, 1H), 3.36-3.47 (m, 2H), 1.41-2.47 (m, 17H), 0.95-1.06 (m, 0.5H), 0.66-0.69 (m, 0.5H), 0.32-0.60 (m, 8H).

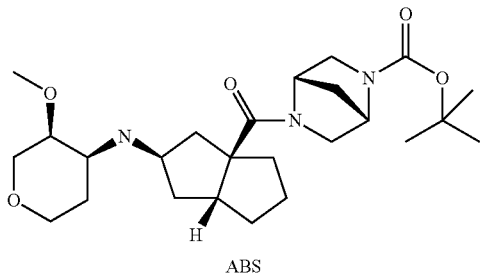

Example 60

1,5-anhydro-3-{[(2R,3aR,6aR)-3a-{[(1S,4S)-5-(tert-butoxycarbonyl)-2,5-diazabicyclo[2.2.1]hept-2-yl]carbonyl}octahydropentalen-2-yl]amino}-2,3-dideoxy-4-O-methyl-D-erythro-pentitol A solution of Example 11B (200 mg, 0.55 mmol), Et$_3$N (84 mg, 0.83 mmol) and (Boc)$_2$O (180 mg, 0.83 mmol) in dichloromethane (1 mL) was stirred at room temperature for 10 h. TLC showed that starting material was consumed. The mixture was extracted with ethyl acetate (20 mL×2). The organic layer was washed with brine, dried over Na$_2$SO$_4$ and concentrated to give a crude product, which was purified by column chromatography (SiO$_2$, 0-100% ethyl acetate in petroleum ether) afforded the title compound. $^1$H NMR (400 MHz, CD$_3$OD) δ (ppm): 4.80 (s, 1H), 4.52 (s, 1H), 4.11-4.25 (d, 1H), 3.87-3.93 (d, 1H), 3.57-3.71 (m, 1H), 3.30-3.43 (m, 10H), 2.88-2.97 (m, 1H), 1.52-2.30 (m, 15H), 1.41-1.49 (d, 9H).

Example 61

[(2R,3aR,6aR)-2-{[(3R,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone Example 61A 3-Methyldihydro-2H-pyran-4(3H)-one To a mixture of tetrahydropyranone (42 g, 0.419 mol) and hexamethylphosphoramide (72 mL) in tetrahydrofuran (400 mL) was added lithium diisopropylamide (262 mL, 0.524 mol) dropwise at −78° C. under N$_2$. After the addition the mixture was stirred for 0.5 hour at −78° C. Iodomethane (250 g, 1.67 mol, 4.0 equivalents) was added to the mixture dropwise. The resulting mixture was stirred for 12 hours at room temperature. TLC (petroleum ether:ethyl acetate=4:1) indicated that the reaction was not complete, the mixture was quenched with aqueous ammonium chloride (100 mL), extracted with ethyl acetate (3×150 mL), the combined organic layers was concentrated in vacuum and the residue was purified by chromatography on silica (0-20% ethyl acetate in petroleum ether) to yield Example 11 (11 g, 22.3%) as a colorless liquid.

Example 61B

[(2R,3aR,6aR)-2-{[(3R,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared and purified using procedure similar to that described in Example 1H substituting Example 61B for Example 1I (SFC condition: Chiral OJ column (250 mm*30 mm, 5 μm) eluting with mobile phase: A, supercritical CO$_2$; B, methanol (0.05% diethylamine), A:B=95:5 with a flow rate of 70 mL/min, peak 1, retention time: 10.11 minutes). $^1$H NMR (400 MHz, CD$_3$OD) δ (ppm): 8.23-8.24 (d, 1H), 6.74-6.82 (m, 2H), 4.96-5.03 (m, 3H), 3.32-4.02 (m, 10H), 2.16-2.87 (m, 1H), 1.57-2.22 (m, 13H), 1.38-1.46 (m, 2H), 0.91-0.98 (m, 3H).

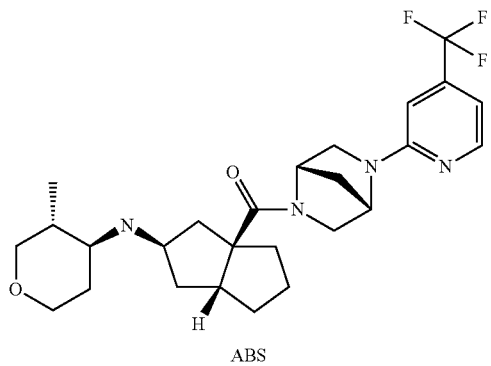

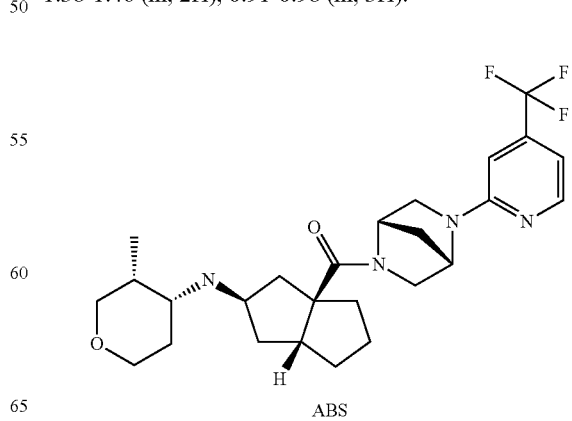

Example 62

[(2R,3aR,6aR)-2-{[(3R,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared according to Example 61 and the isolated by SFC (Chiral OJ column (250 mm*30 mm, 5 μm) eluting with mobile phase: A, supercritical $CO_2$; B, methanol (0.05% diethylamine), A:B=75:25 with a flow rate of 50 mL/min, peak 2, retention time: 10.49 minutes). $^1$H NMR (400 MHz, $CD_3OD$) δ (ppm): 8.24 (s, 1H), 6.80-6.82 (m, 2H), 4.96 (s, 3H), 4.06-4.13 (m, 0.5H), 3.32-3.90 (m, 9H), 2.60-2.85 (m, 1H), 1.23-2.22 (m, 14.5H), 0.90-0.98 (m, 3H).

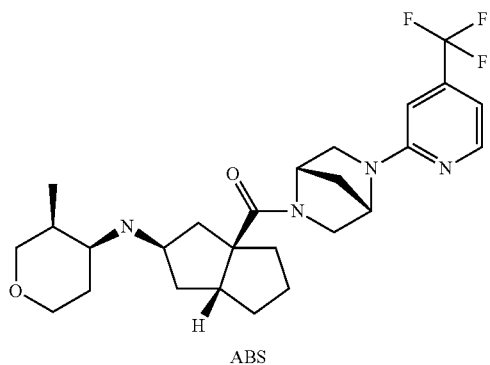

ABS

Example 63

[(2R,3aR,6aR)-2-{[(3S,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared according to Example 61 and purified by SFC conditions (Chiral OJ column (250 mm*30 mm, 5 μm) eluting with mobile phase:A, supercritical $CO_2$; B, ethanol (0.05% diethylamine), A:B=95:5 with a flow rate of 70 mL/min, peak 3, retention time: 11.24 minutes). $^1$H NMR (400 MHz, $CD_3OD$) δ (ppm): 8.24 (s, 1H), 6.80-6.82 (m, 2H), 4.96 (s, 3H), 3.32-3.90 (m, 9H), 2.60-2.85 (m, 1H), 1.23-2.22 (m, 15H), 0.90-0.98 (m, 3H).

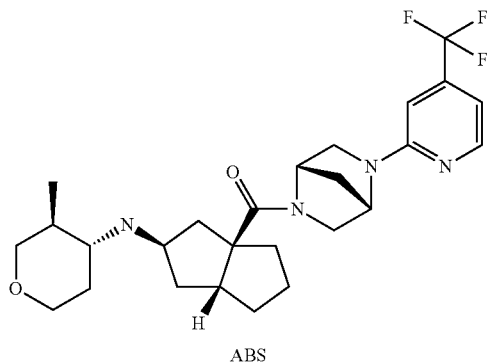

ABS

Example 64

[(2R,3aR,6aR)-2-{[(3S,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared according to Example 61 and purified under SFC conditions (Chiral OJ column (250 mm*30 mm, 5 μm) eluting with mobile phase: A, supercritical $CO_2$; B, ethanol (0.05% diethylamine), A:B=90:10 with a flow rate of 70 mL/min, peak 4, retention time: 12.13 minutes). $^1$H NMR (400 MHz, $CD_3OD$) δ (ppm): 8.24-8.26 (d, 1H), 6.68-6.82 (m, 2H), 4.92-4.98 (m, 3H), 4.61 (s, 1H), 3.36-3.92 (m, 9H), 1.31-2.00 (m, 15H), 0.86-1.01 (m, 3H).

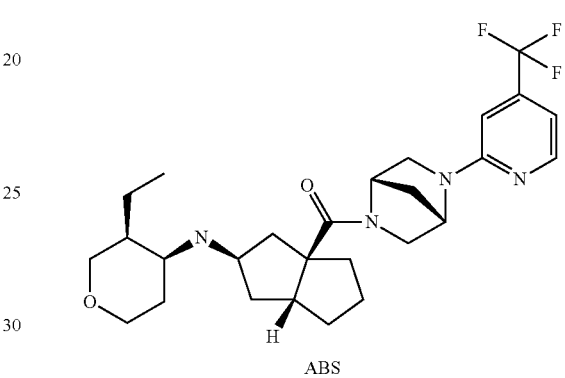

ABS

Example 65

[(2R,3aR,6aR)-2-{[(3S,4S)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone

Example 65A 3-ethyldihydro-2H-pyran-4(3H)-one

To a mixture of tetrahydropyran-4 one (5 g, 0.05 mol) and hexamethylphosphoramide (9 mL) in tetrahydrofuran (100 mL) was added lithium diisopropylamide (34.7 mL, 0.062 mol) dropwise at −78° C. under $N_2$. After the addition the mixture was stirred for 0.5 h at −78° C. Iodoethane (7.78 g, 0.199 mol) was added to the mixture dropwise. The ddresulting mixture was stirred for 12 hours at room temperature. TLC (petroleum ether:ethyl acetate=4:1) indicated the reaction was not complete, the mixture was quenched with aqueous ammonium chloride (100 mL), extracted with ethyl acetate (3×50 mL), the combined organic layers was concentrated in vacuo and the residue was purified by chromatography on silica using petroleum ether: ethyl acetate from 15:1 to 10:1 to yield compound the title compound (2.5 g, 39.1%) as a colorless liquid. $^1$H NMR (400 MHz, $CD_3OD$) δ (ppm): 4.15 (m, 2H), 3.80 (m, 1H), 3.45 (m, 1H), 2.58 (m, 1H), 2.48 (m, 2H), 1.81 (m, 1H), 1.30 (m, 1H), 0.92 (m, 3H).

Example 65B

[(2R,3aR,6aR)-2-{[(3S,4S)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared using procedure similar to that described in Example 1J, substituting Example 65 for Example 1I (SFC condition: Chiral IC column (250 mm*30 mm, 5 μm) eluting with mobile phase: A, supercritical $CO_2$; B, ethanol (0.05% diethylamine), A:B=65:35 with a flow rate of 75 mL/min, peak 2, retention time: 16.09 minutes). $^1$H NMR (400 MHz, $CD_3OD$) δ (ppm): 8.24 (s, 1H), 6.74-6.82 (m, 2H), 4.91-4.98 (m, 2H), 3.34-3.89 (m, 8.5H), 2.74-2.94 (m, 1H), 1.24-2.11 (m, 18.5H), 0.87-0.94 (m, 3H).

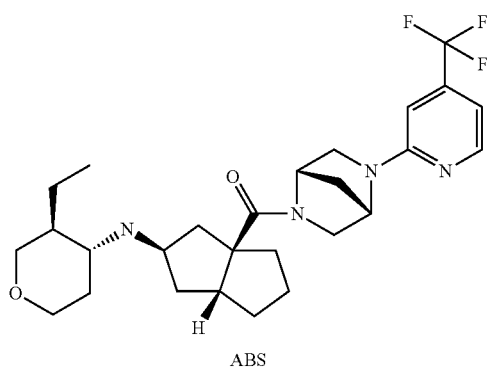

ABS

Example 66

[(2R,3aR,6aR)-2-{[(3S,4R)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone The title compound was prepared using procedure similar to that described in Example 1J, and purified under SFC conditions (Chiral IC column (250 mm*30 mm, 5 μm) eluting with mobile phase: A, supercritical $CO_2$; B, ethanol (0.05% diethylamine), A:B=65:35 with a flow rate of 75 mL/min, peak 3, retention time: 18.08 minutes). $^1$H NMR (400 MHz, $CD_3OD$) δ (ppm): 8.23-8.24 (d, 1H), 6.73-6.82 (m, 2H), 4.92-4.99 (m, 2H), 3.31-3.94 (m, 10H), 2.88-3.03 (m, 1H), 2.25-2.26 (m, 0.5H), 1.22-2.13 (m, 13.5H), 0.85-0.97 (m, 3H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound of formula (I):

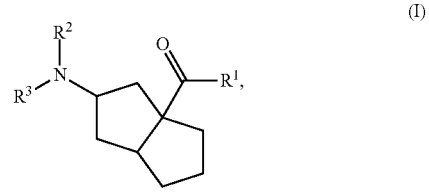

(I)

or a pharmaceutically acceptable salt thereof, wherein:
$R^1$ is formula (a) or (b):

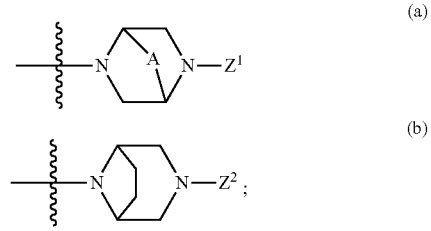

(a)

(b)

A is $CH_2$ or $CH_2CH_2$;
$Z^1$ and $Z^2$, are each independently —C(O)O(alkyl), aryl, or monocyclic heteroaryl, each of which is independently unsubstituted or substituted with 1, 2, 3, or 4 substituents independently selected from the group consisting of $C_1$-$C_6$ alkyl, $C_2$-$C_4$ alkenyl, $C_2$-$C_4$ alkynyl, halogen, $C_1$-$C_6$ haloalkyl, CN, $OR^a$, $NR^bR^c$, —C(O)$NR^bR^c$, and —S(O)$_2NR^bR^c$; wherein $R^a$, $R^b$, and $R^c$, at each occurrence, are each independently hydrogen, $C_1$-$C_6$ alkyl, or $C_1$-$C_6$ haloalkyl;
$R^2$ is hydrogen or $C_1$-$C_6$ alkyl wherein the $C_1$-$C_6$ alkyl is optionally substituted with $C_1$-$C_6$ haloalkyl, alkoxy, or haloalkoxy, and $R^3$ is:

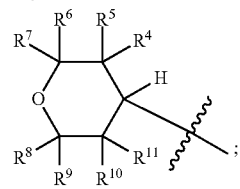

wherein
$R^4$ is $C_1$-$C_6$ alkyl, O($C_1$-$C_6$ alkyl), or O($C_1$-$C_6$ haloalkyl);
$R^5$, $R^6$, $R^7$, $R^8$, $R^9$, $R^{10}$, and $R^{11}$, are each independently hydrogen, $C_1$-$C_6$ alkyl, or halogen;
or $R^2$ and $R^3$, together with the nitrogen atom to which they are attached, form a ring of formula (i), (ii), or (iii):

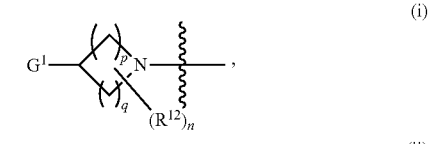

(i)

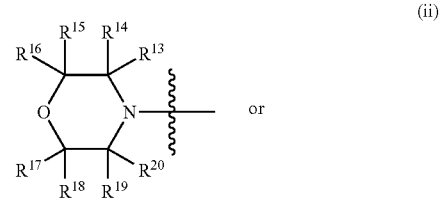

(ii)

or

-continued (iii)

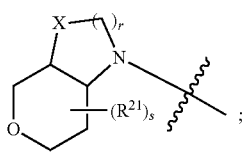

wherein:
R$^{12}$, at each occurrence, represents an optional substituent on any substitutable carbon atom, and is independently C$_1$-C$_6$ alkyl, C$_1$-C$_6$ haloalkyl, CN, OH, or halogen;
n is 0, 1, or 2;
p is 1 or 2;
q is 1 or 2;
G$^1$ is aryl which is optionally substituted with 1, 2, or 3 substituents independently selected from the group consisting of C$_1$-C$_6$ alkyl, halogen, C$_1$-C$_6$ haloalkyl, OH, alkoxy, haloalkoxy, CN, —C(O)OH, —C(O)O(alkyl), —(C$_1$-C$_6$ alkylenyl)-OH, —(C$_1$-C$_6$ alkylenyl)-C(O)OH, or tetrazolyl;
R$^{13}$ is hydrogen, C$_1$-C$_6$ alkyl, or —(C$_1$-C$_6$ alkylenyl)-O(alkyl);
R$^{14}$, R$^{15}$, R$^{16}$, R$^{17}$, R$^{18}$, R$^{19}$, and R$^{20}$, are each independently hydrogen or C$_1$-C$_6$ alkyl;
X is CH$_2$, O, N(R$^w$) wherein R$^w$ is hydrogen, C$_1$-C$_6$ alkyl, or C$_1$-C$_6$ haloalkyl;
r is 1 or 2;
s is 0, 1, 2, 3, or 4; and
R$^{21}$, at each occurrence, represents an optional substituent on any substitutable carbon atom of the bicyclic ring, and is independently halogen, C$_1$-C$_6$ alkyl, or C$_1$-C$_6$ haloalkyl.

2. The compound or salt of formula (I) according to claim 1, wherein R$^1$ is formula (a) and A is CH$_2$.

3. The compound or salt of formula (I) according to claim 1, wherein R$^1$ is formula (a), A is CH$_2$, and Z$^1$ is aryl or monocyclic heteroaryl.

4. The compound or salt of formula (I) according to claim 1, wherein R$^1$ is formula (b) and Z$^2$ is aryl or monocyclic heteroaryl.

5. The compound or salt of formula (I) according to claim 1, wherein:
R$^3$ is

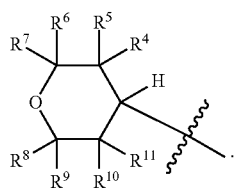

6. The compound or salt of formula (I) according to claim 1, wherein R$^2$ and R$^3$, together with the nitrogen atom to which they are attached, form a ring of formula (i) or (ii).

7. The compound or salt of formula (I) according to claim 1, wherein R$^2$ and R$^3$, together with the nitrogen atom to which they are attached, form a ring of formula (i), p and q are 2, and n is 0.

8. The compound or salt of formula (I) according to claim 1, wherein R$^2$ and R$^3$, together with the nitrogen atom to which they are attached, form a ring of formula (i), p and q are 2, n is 0, and G$^1$ is optionally substituted aryl.

9. The compound or salt of formula (I) according to claim 1, wherein:
R$^1$ is formula (a);
A is CH$_2$; and
R$^3$ is

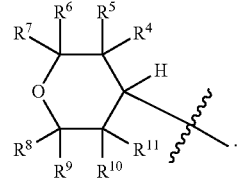

10. The compound or salt of formula (I) according to claim 9, wherein:
R$^4$ is C$_1$-C$_6$ alkyl or O(C$_1$-C$_6$ alkyl); and
R$^5$, R$^6$, R$^7$, R$^8$, R$^9$, R$^{10}$, and R$^{11}$ are hydrogen.

11. The compound or salt of formula (I) according to claim 10, wherein Z$^1$ is aryl or monocyclic heteroaryl, each of which is optionally substituted.

12. The compound or salt of formula (I) according to claim 10, wherein Z$^1$ is optionally substituted pyridinyl.

13. The compound or salt of formula (I) according to claim 1, wherein:
R$^1$ is formula (a);
A is CH$_2$; and
R$^2$ and R$^3$, together with the nitrogen atom to which they are attached, form a ring of formula (i) or (ii).

14. The compound or salt of formula (I) according to claim 13, wherein:
R$^2$ and R$^3$, together with the nitrogen atom to which they are attached, form a ring of formula (i);
p and q are 2;
n is 0; and
G$^1$ is optionally substituted aryl.

15. The compound or salt of formula (I) according to claim 1, wherein:
R$^1$ is formula (b); and
R$^3$ is

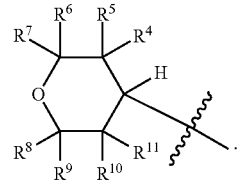

16. The compound or salt of formula (I) according to claim 15, wherein:
R$^4$ is C$_1$-C$_6$ alkyl or O(C$_1$-C$_6$ alkyl); and
R$^5$, R$^6$, R$^7$, R$^8$, R$^9$, R$^{10}$, and R$^{11}$ are hydrogen.

17. The compound or salt of formula (I) according to claim 16, wherein Z$^2$ is aryl or monocyclic heteroaryl, each of which is optionally substituted.

18. The compound or salt of formula (I) according to claim 16, wherein Z$^2$ is optionally substituted pyridinyl.

19. The compound or salt of formula (I) according to claim 1, wherein the compound is selected from the group consisting of:

1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,4R)-5-[4-(trifluoromethyl)pyridin-2-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[5-(trifluoromethyl)pyridazin-3-yl]-2,5-diazabicyclo[2.2.1]hept-2-yl}carbonyl)octahydropentalen-2-yl]amino}-D-threo-pentitol;

1,5-anhydro-2,3-dideoxy-4-O-methyl-3-{methyl[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-erythro-pentitol;

3-{1-[(2S,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid;

3-{1-[(2R,3aR,6aR)-3a-({(1S,4S)-5-[4-(trifluoromethyl)pyridin-2-yl]-2,5-diazabicyclo[2.2.1]hept-2-yl}carbonyl)octahydropentalen-2-yl]piperidin-4-yl}benzoic acid;

1,5-anhydro-2,3-dideoxy-4-O-methyl-3-{[(2R,3aR,6aR)-3a-({(1S,4S)-5-[6-methyl-4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-(trifluoromethyl)pyrimidin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[6-(trifluoromethyl)pyrimidin-4-yl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[2-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-3-{[(2R,3aR,6aR)-3a-({(1S,4S)-5-[4-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[2-methyl-5-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[2-fluoro-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[3-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-methyl-3-(trifluoromethyl)phenyl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-{[(1S,4S)-5-(3-chloro-4-fluorophenyl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-2,3-dideoxy-3-{[(2R,3aR,6aR)-3a-({(1S,4S)-5-[3-fluoro-4-(trifluoromethyl)pyridin-2-yl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[6-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[2-methyl-3-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[3-methyl-5-(trifluoromethyl)phenyl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[3-fluoro-5-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-2,3-dideoxy-4-O-methyl-3-{[(2R,3aR,6aR)-3a-({(1S,4S)-5-[2-(trifluoromethyl)pyridin-4-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[2-(trifluoromethyl)pyrimidin-4-yl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-(trifluoromethoxy)phenyl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[4-(trifluoromethyl)-1,3-thiazol-2-yl]-2,5-diazabicyclo[2.2.1]hept-2-yl}carbonyl)octahydropentalen-2-yl]amino}-D-erythro-pentitol;

1,5-anhydro-2,3-dideoxy-3-{[(2R,3aR,6aR)-3a-({(1S,4S)-5-[4-methoxy-3-(trifluoromethyl)phenyl]-2,5-diazabicyclo[2.2.1]hept-2-yl}carbonyl)octahydropentalen-2-yl]amino}-4-O-methyl-D-erythro-pentitol;

1,5-anhydro-3-{[(2R,3aR,6aR)-3a-({(1S,4S)-5-[3-chloro-5-(trifluoromethyl)pyridin-2-yl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-2,3-dideoxy-4-O-methyl-3-{[(2R,3aR,6aR)-3a-({(1S,4S)-5-[5-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-{[(1S,4S)-5-(2-chloropyridin-4-yl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-3-{[(2R,3aR,6aR)-3a-({(1S,4S)-5-[5-cyano-2-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-cyano-2-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-4-O-methyl-3-{[(2R,3aR,6aR)-3a-({(1S,4S)-5-[3-methyl-4-(trifluoromethyl)pyridin-2-yl]-2,5-diazabicyclo[2.2.1]hept-2-yl}carbonyl)octahydropentalen-2-yl]amino}-D-erythro-pentitol;

1,5-anhydro-3-{[(2R,3aR,6aR)-3a-({(1S,4S)-5-[4-cyano-3-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-2,3-dideoxy-3-{[(2R,3aR,6aR)-3a-{[(1S,4S)-5-(3,4-dichlorophenyl)-2,5-diazabicyclo[2.2.1]hept-2-yl]carbonyl}octahydropentalen-2-yl]amino}-4-O-methyl-D-erythro-pentitol;

1,5-anhydro-2,3-dideoxy-4-O-methyl-3-{[(2R,3aR,6aR)-3a-({(1R,5S)-3-[4-(trifluoromethyl)pyridin-2-yl]-3,8-diazabicyclo[3.2.1]oct-8-yl}carbonyl)octahydropentalen-2-yl]amino}-D-threo-pentitol;

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl]amino}-2,3-dideoxy-4-O-methyl-D-erythro-pentitol;

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-{[(1S,4S)-5-(4-chloro-3-cyanophenyl)-2,5-diazabicyclo[2.2.1]hept-2-yl]carbonyl}octahydropentalen-2-yl]amino}-2,3-dideoxy-4-O-methyl-D-erythro-pentitol;

2-[(1S,4S)-5-{[(2R,3aR,6aR)-2-(4-phenylpiperidin-1-yl)hexahydropentalen-3a(1H)-yl]carbonyl}-2,5-diazabicyclo[2.2.1]hept-2-yl]-4-(trifluoromethyl)benzonitrile;

[(2R,3aR,6aR)-2-(4-phenylpiperidin-1-yl)hexahydropentalen-3a(1H)-yl]{(1S,4S)-5-[4-(trifluoromethyl)pyridin-2-yl]-2,5-diazabicyclo[2.2.1]hept-2-yl}methanone;

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl]amino}-2,3-dideoxy-4-O-methyl-D-erythro-pentitol;

1,5-anhydro-3-{[(2R,3aR,6aR)-3a-({(1S,4S)-5-[4-chloro-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2-cyano-5-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[2-cyano-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[3,5-bis(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[4-cyano-3-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-({(1S,4S)-5-[3-cyano-5-(trifluoromethyl)phenyl]-2,5-diazabicyclo[2.2.1]hept-2-yl}carbonyl)octahydropentalen-2-yl](methyl)amino}-2,3-dideoxy-4-O-methyl-D-erythro-pentitol;

1,5-anhydro-3-{[(2R,3aR,6aR)-3a-{[(1S,4S)-5-(3-chloro-2-cyanophenyl)-2,5-diazabicyclo[2.2.1]hept-2-yl]carbonyl}octahydropentalen-2-yl](methyl)amino}-2,3-dideoxy-4-O-methyl-D-erythro-pentitol;

[(2R,3aR,6aR)-2-(morpholin-4-yl)hexahydropentalen-3a(1H)-yl]{(1S,4S)-5-[4-(trifluoromethyl)pyridin-2-yl]-2,5-diazabicyclo[2.2.1]hept-2-yl}methanone;

1,5-anhydro-3-{[(2R,3aR,6aR)-3a-{[(1S,4S)-5-(tert-butoxycarbonyl)-2,5-diazabicyclo[2.2.1]hept-2-yl]carbonyl}octahydropentalen-2-yl]amino}-2,3-dideoxy-4-O-methyl-D-erythro-pentitol;

[(2R,3aR,6aR)-2-{[(3R,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3R,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4S)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4R)-3-methyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone;

[(2R,3aR,6aR)-2-{[(3S,4S)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone; and

[(2R,3aR,6aR)-2-{[(3S,4R)-3-ethyltetrahydro-2H-pyran-4-yl]amino}hexahydropentalen-3a(1H)-yl]{(1S,4S)-5-[4-(trifluoromethyl)pyridin-2-yl]-2,5-diazabicyclo[2.2.1]hept-2-yl}methanone.

20. A pharmaceutical composition comprising a therapeutically effective amount of a compound of formula (I) according to claim 1, or a pharmaceutically acceptable thereof, in combination with a pharmaceutically acceptable carrier.

21. A method for treating pain in a subject in need of such treatment comprising administering to the subject a therapeutically effective amount of a compound of formula (I) according to claim 1, or a pharmaceutically acceptable salt thereof, alone or in combination with a pharmaceutically acceptable carrier.

* * * * *